US010639350B2

(12) United States Patent
Arber et al.

(10) Patent No.: US 10,639,350 B2
(45) Date of Patent: May 5, 2020

(54) METHODS AND PHARMACEUTICAL COMPOSITIONS FOR IMPROVING WOUND HEALING USING CD24

(71) Applicant: The Medical Research, Infrastructure and Health Services Fund of the Tel Aviv Medical Center, Tel-Aviv (IL)

(72) Inventors: Nadir Arber, Tel-Aviv (IL); Shiran Shapira, Petach-Tikva (IL); Dina Kazanov, Rishon-LeZion (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 0 days.

(21) Appl. No.: 15/751,215

(22) PCT Filed: Aug. 10, 2016

(86) PCT No.: PCT/IL2016/050873
§ 371 (c)(1),
(2) Date: Feb. 8, 2018

(87) PCT Pub. No.: WO2017/025963
PCT Pub. Date: Feb. 16, 2017

(65) Prior Publication Data
US 2018/0221445 A1 Aug. 9, 2018

Related U.S. Application Data

(60) Provisional application No. 62/202,937, filed on Aug. 10, 2015.

(51) Int. Cl.
| *A61K 38/00* | (2006.01) |
| *A61K 38/16* | (2006.01) |
| *A61K 38/17* | (2006.01) |
| *A61L 15/44* | (2006.01) |
| *A61K 9/06* | (2006.01) |
| *A61K 9/00* | (2006.01) |
| *A61K 48/00* | (2006.01) |

(52) U.S. Cl.
CPC ........ *A61K 38/1774* (2013.01); *A61K 9/0014* (2013.01); *A61K 9/0019* (2013.01); *A61K 9/06* (2013.01); *A61K 38/177* (2013.01); *A61L 15/44* (2013.01); *A01K 2217/075* (2013.01); *A01K 2227/105* (2013.01); *A01K 2267/03* (2013.01); *A61K 48/00* (2013.01); *A61L 2300/252* (2013.01); *C12N 2740/15043* (2013.01)

(58) Field of Classification Search
None
See application file for complete search history.

(56) References Cited

U.S. PATENT DOCUMENTS

2003/0106084 A1 6/2003 Liu et al.

FOREIGN PATENT DOCUMENTS

| WO | WO 01/72325 | 10/2001 |
| WO | WO 2012/068299 | 5/2012 |
| WO | WO 2017/025963 | 2/2017 |

OTHER PUBLICATIONS

International Preliminary Report on Patentability dated Feb. 22, 2018 From the International Bureau of WIPO Re. Application No. PCT/IL2016/050873. (9 Pages).
International Search Report and the Written Opinion dated Nov. 14, 2016 From the international Searching Authority Re. Application No. PCT/IL2016/050873. (14 Pages).
Ahmed et al. "CD24 Is Upregulated in Inflammatory Bowel Disease and Stimulates Cell Motility and Colony Formation", Inflammatory Bowel Disease, 16(5): 795-803, Published Online Dec. 8, 2009.
Aigner et al. "CD24 Mediates Rolling of Breast Carcinoma Cells on P-Selectin", The FASEB Journal, 12(12): 1241-1251, Sep. 1998.
Aigner et al. "CD24, A Mucin-Type Glycoprotein, Is a Ligand for P-Selectin on Human Tumor Cells", Blood, 89(9): 3385-3395, May 1, 1997.
Aigner et al. "Heat Stable Antigen (Mouse CD24) Supports Myeloid Cell Binding to Endothelial and Platelet P-Selectin", International Immunology, 7(10): 1557-1565, Oct. 1995.
Devalaraja et al. "Delayed Wound Healing in CXCR2 Knockout Mice", Journal of Investigative Dermatology, 115(2): 234-244, Aug. 2000.
Jaakkola et al. "Wound Reepithelialization Activates a Growth Factor-Responsive Enhancer in Migrating Keratinocytes", The FASEB Journal, 12(11): 959-969, Aug. 1998.
Kadmon et al. "Differential, LFA-1-Sensitive Effects of Antibodies to Nectadrin, the Heat-Stable antigen, on B Lymphoblast Aggregation and Signal Transduction", Biochemical and Biophysical Research Communications, 198(3): 1209-1215, Feb. 15, 1994.
Kristiansen et al. "Tumour Biological Aspects of CD24, A Mucin-Like Adhesion Molecule", Journal of Molecular Histology, 35(3): 255-262, Mar. 2004.
Martin "Wound Healing—Aiming for Perfect Skin Regeneration", Science, 276(5309): 75-81, Published Online Apr. 4, 1997.
Martin et al. "Inflammatory Cells During Wound Repair: The Good, the Bad and the Ugly", Trends in Cell Biology, 15(11): 599-607, Available Online Oct. 3, 2005.

(Continued)

*Primary Examiner* — Christine J Saoud
*Assistant Examiner* — Jon M Lockard

(57) ABSTRACT

Provided are methods of improving wound healing in a subject by administering a therapeutically effective amount of CD24. Also provided are pharmaceutical compositions which comprise CD24 being in a formulation with a surfactant and a pharmaceutically acceptable carrier.

20 Claims, 30 Drawing Sheets
(28 of 30 Drawing Sheet(s) Filed in Color)
Specification includes a Sequence Listing.

(56) References Cited

OTHER PUBLICATIONS

Shapira et al. "Delayed Wound Healing in Heat Antigen (HSA/CD24)-Deficient Mice", PLoS ONE, 10(10): e0139787-1-e0139787-15, Oct. 6, 2015.
Shapira et al. "The CD24 Protein Inducible Expression System Is an Ideal Tool to Explore the Potential of CD24 as an Oncogene and a Target for Immunotherapy in Vitro and in Vivo", The Journal of Biological Chemistry, 286(47): 40548-40555, Nov. 25, 2011.
Shekhawat "Preparation and Evaluation of Clotrimazole Nanostructured Lipid Carrier for Topical Delivery", International Journal of Pharma and Bio Sciences, 4(1): 407-416, Jan. 18, 2013. Abstract.
Singer et al. "Cutaneous Wound Healing", The New England Journal of Medicine, 341(10): 738-746, Sep. 2, 1999.
Suzuki et al. "CD24 Induces Apoptosis in Human B Cells Via the Glycolipid-Enriched Membrane Domains/Rafts-Mediated Signaling System", The Journal of Immunology, 166(9): 5567-5577, May 2001.
Tonnesen et al. "Angiogenesis in Wound Healing", Journal of investigative Dermatology Symposium Proceedings, 5(1): 40-46, Dec. 2000.
Werner et al. "Regulation of Wound Healing by Growth Factors and Cytokines", Physiological Reviews, 83(3): 835-870, Jul. 2003.
Zcharia et al. "Heparanase Acclerates Wound Angiogenesis and Wound Healing in Mouse and Rat Models", The FASEB Journal, 19(2): 211-221, Feb. 2005.
Office Action dated May 7, 2019 From the Israel Patent Office Re. Application No. 257358 and Its Translation Into English. (7 Pages).
Dvorak "Tumors: Wounds That Do Not Heal. Similarities Between Tumor Stroma Generation and Wound Healing", The New England Journal of Medicine, 315(26): 1650-1659, Dec. 25, 1986.
Supplementary European Search Report and the European Search Opinion dated Jan. 21, 2019 From the European Patent Office Re. Application No. 16834770.6. (7 Pages).
Naumov et al. "CD24 Is an Important Oncogene in the Colon", Database Biosis [Online], XP009510296, Database Accession No. PREV201100405303, Digestive Disease Week, Chicago, IL, USA, May 7-10, 2011, Gastroenterology, 140(Suppl.1): S-816, # Tu1708, May 7, 2011.

Fig. 1A
Fig. 1C
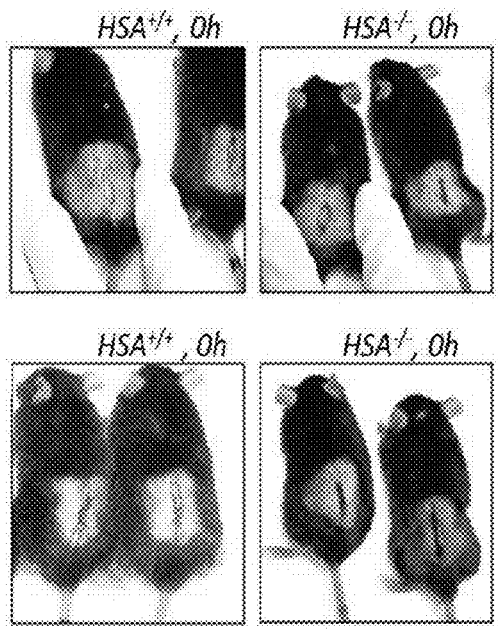
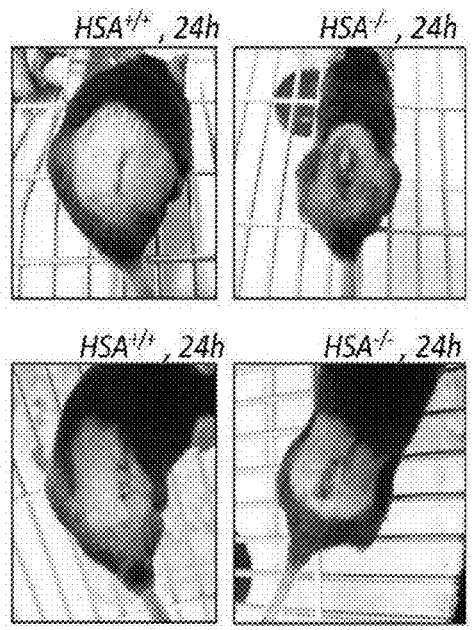
Fig. 1D
Fig. 1B
Fig. 1E
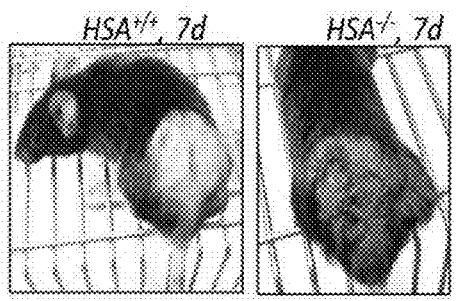
Fig. 1F
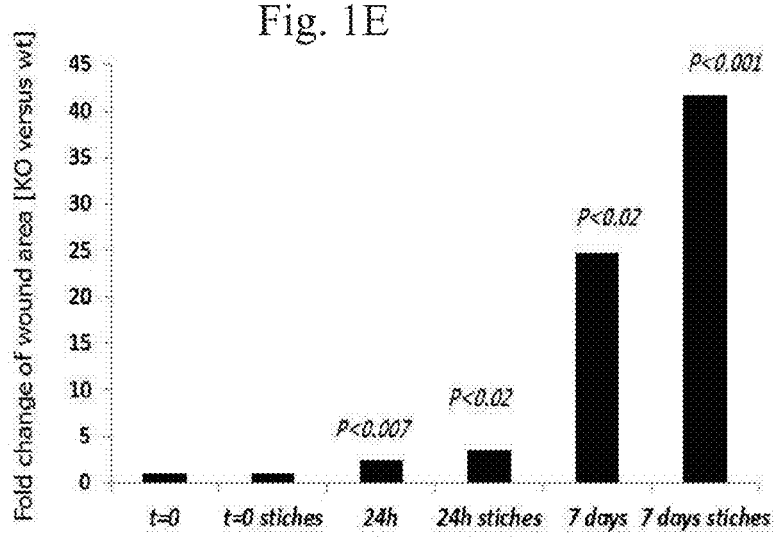
Fig. 1G

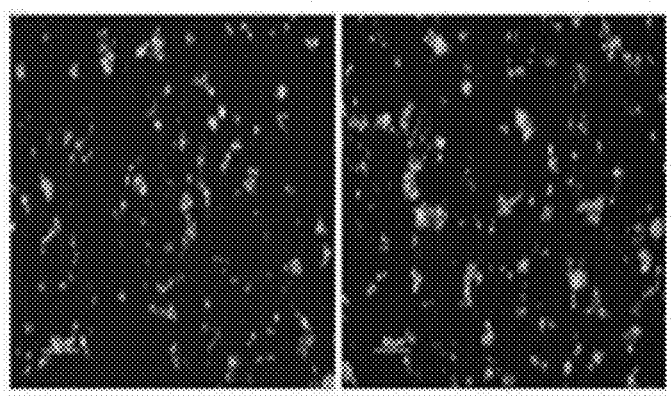
Fig. 5A  HEK293T
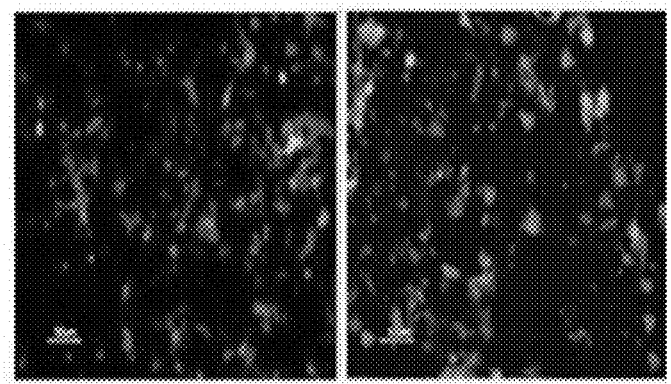
Fig. 5B  NIH-3T3
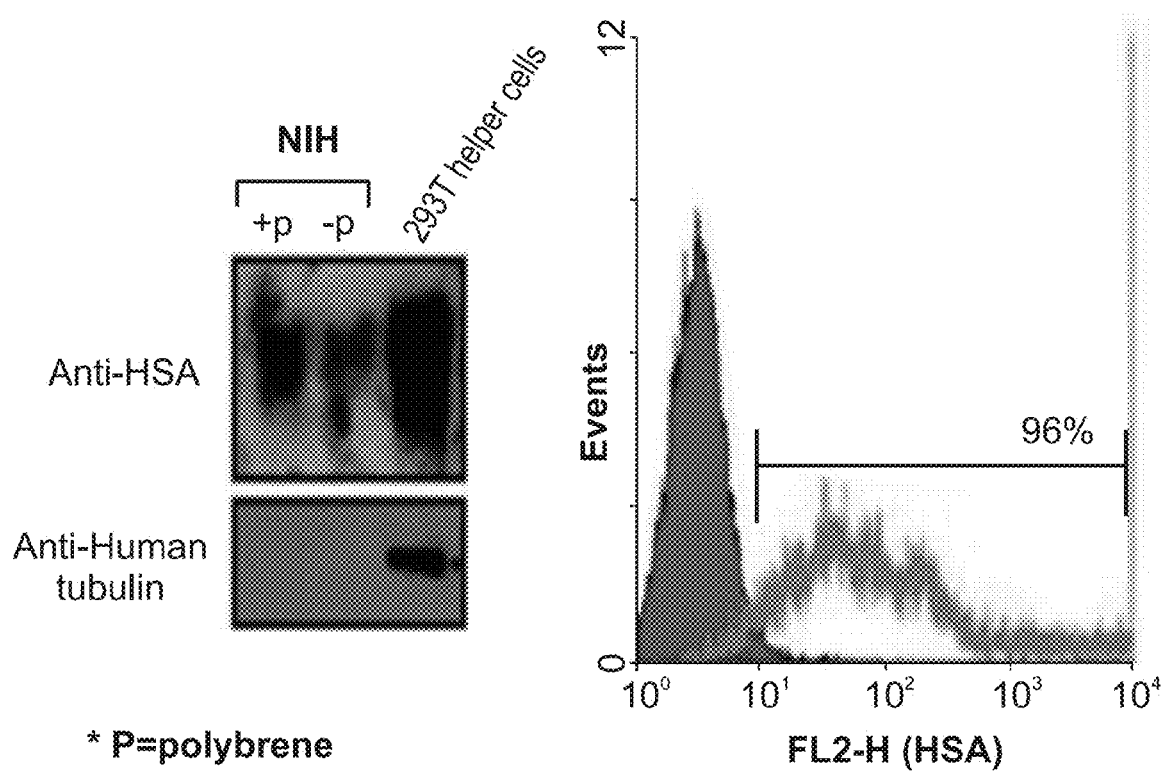
Fig. 5C
* P=polybrene
Fig. 5D

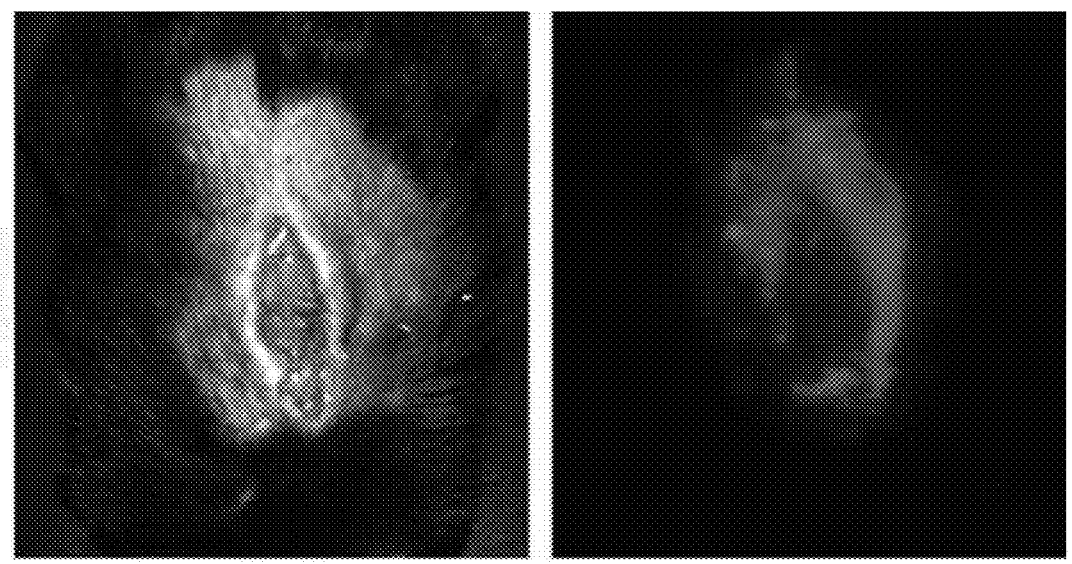
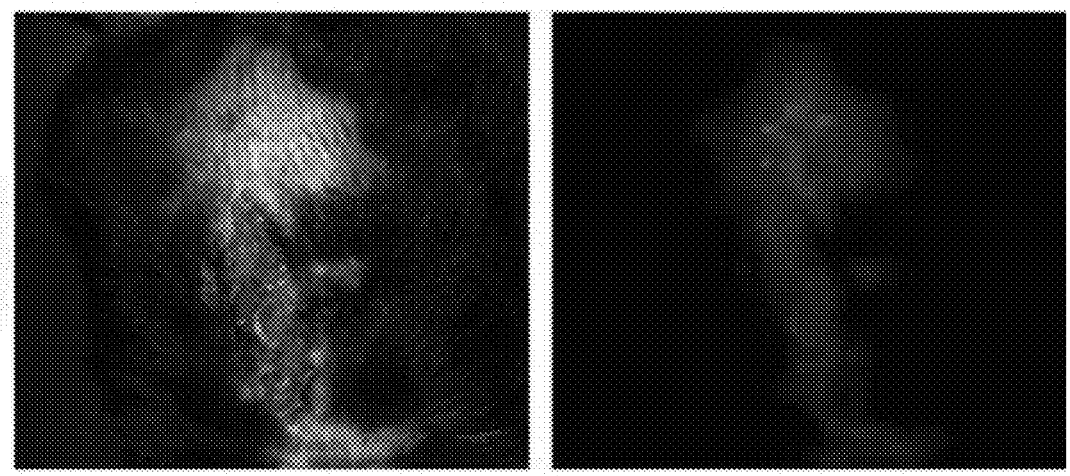
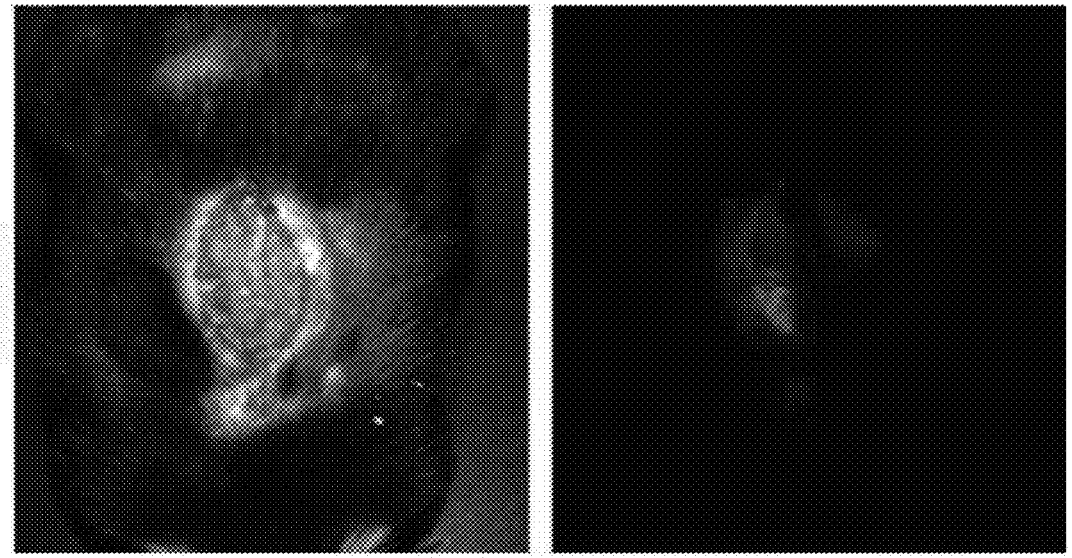
Fig. 6C Mouse 3  Fig. 6B Mouse 2  Fig. 6A Mouse 1

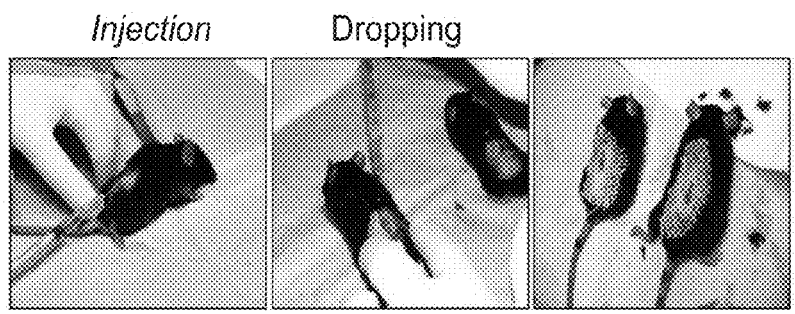
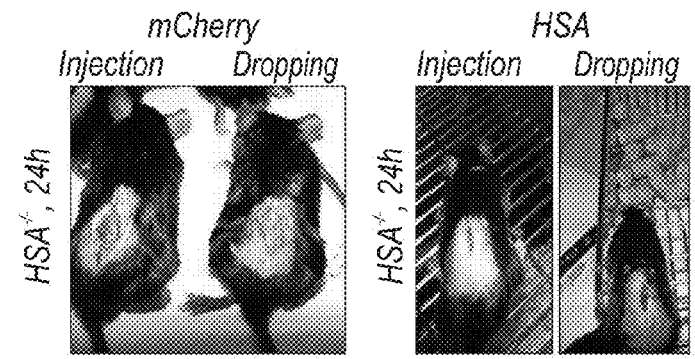
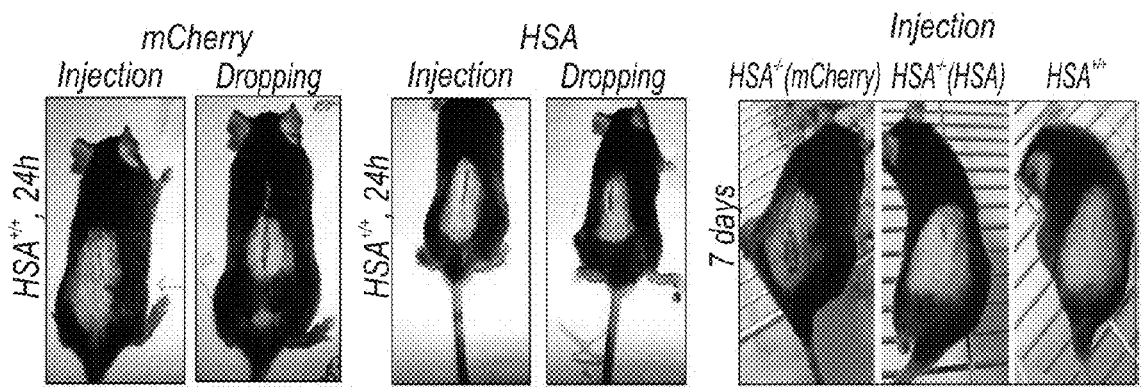
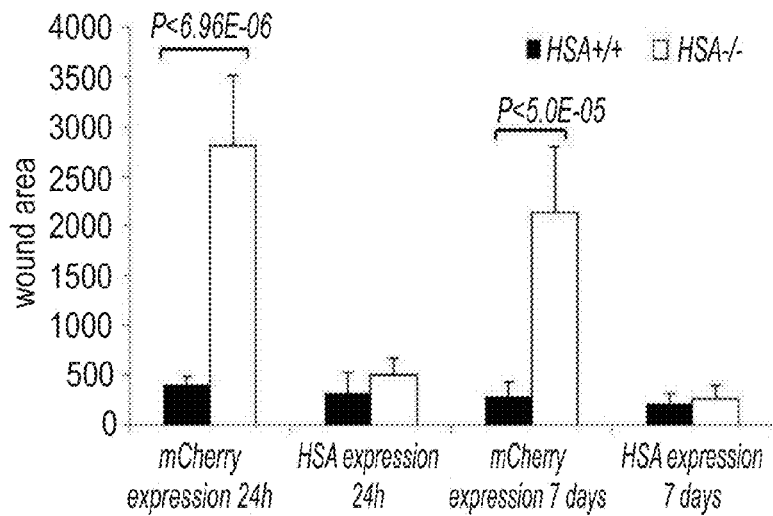
Fig. 7A  Fig. 7B  Fig. 7C  Fig. 7D  Fig. 7E  Fig. 7F  Fig. 7G Fig. 9A
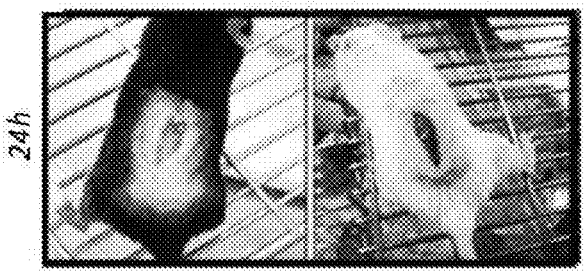
Fig. 9B
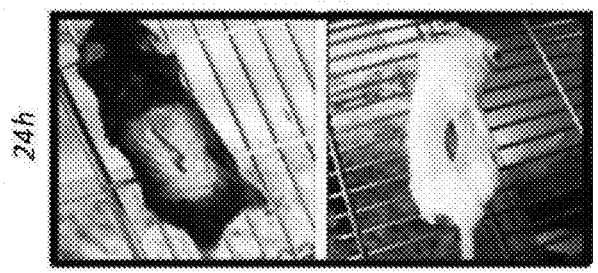
Fig. 9C
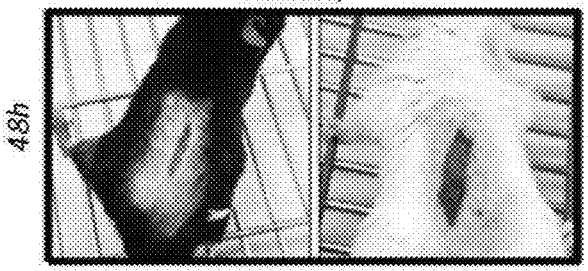
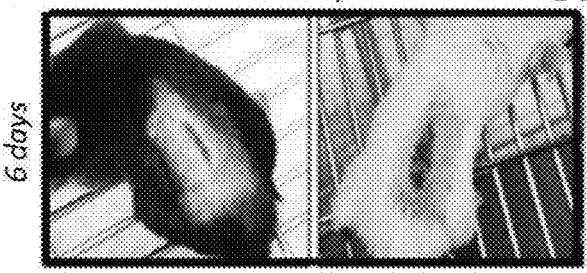
Fig. 9D
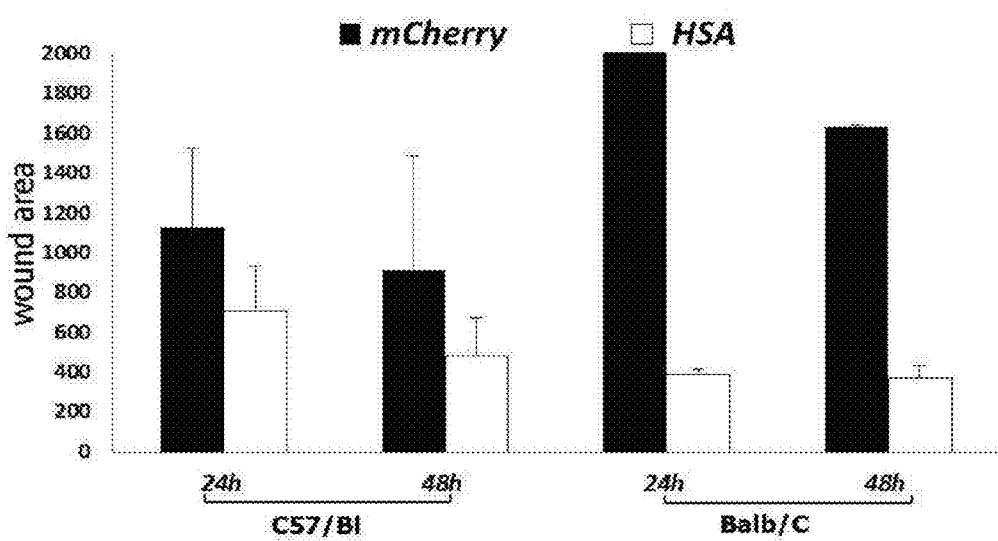
Fig. 9E

Fig. 10A

DNA encoding the full length human CD24 protein

▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒
▒▒▒▒▒▒▒▒▒▒▒▒▒▒▒▒▒▒▒▒▒AGTGAAACAACAACTGGAACTTCAAGTAACT
CCTCCCAGAGTACTTCCAACTCTGGGTTGGCCCCAAATCCAACTAATGCCACCAC
CAAGGCG▒▒▒▒▒▒▒▒▒▒▒▒▒▒▒▒▒▒▒▒▒▒▒▒▒▒▒▒▒▒▒▒▒▒▒▒▒▒▒▒▒▒▒▒▒
▒▒▒▒▒▒▒▒▒▒▒▒▒▒▒▒TAA (SEQ ID NO: 1)

Fig. 10B

DNA encoding soluble human CD24 protein

▒▒▒▒▒▒▒▒▒▒▒▒▒▒▒▒▒▒▒▒▒▒▒▒▒▒▒▒▒▒▒▒▒▒▒▒▒▒▒▒▒▒GGTAAGGGGTTAACA
GTAGCAGGCTTGAGGTCTGGACATATATATGGGTGACAATGACATCCACTTTGCC
TTTCTCTCCACA▒▒▒▒▒▒▒▒▒▒▒▒▒▒▒ACCGGTGGCTCGGTACCGGGCAGTGGCGGAT
CAGAGAATCTTTATTTTCAGGGTAGTGAAACAACAACTGGAACTTCAAGTAACTC
CTCCAGAGTACTTCCAACTCTGGGTTGGCTCCAAATCCAACTAATGCCACCACC
AAGGCGGGATCCATCATCATCATCATCATTGA (SEQ ID NO:7)

Fig. 12A

CD24 Core Amino Acid sequence

SETTTGTSSNSSQSTSNSGLAPNPTNATTKA
(SEQ ID NO: 28)

Fig. 12B

CD24 Full length Amino Acid sequence

MGRAMVARLGLGLLLLALLLPTQIYSSETTTGTSSNSSQS
TSNSGLAPNPTNATTKAAGGALQSTASLFVVSLSLLHLYS
(SEQ ID NO: 29)

Fig. 12C

CD24 Soluble Amino Acid sequence

MGWSCIILFLVATATGAHSTGGSVPGSGGSENLYFQGSETTT
GTSSNSSQSTSNSGLAPNPTNATTKAGSHHHHHH
(SEQ ID NO: 30)

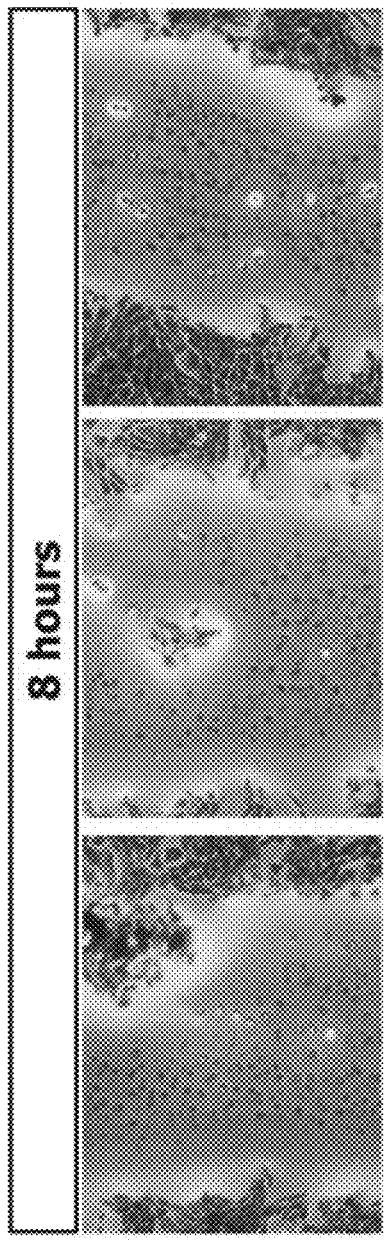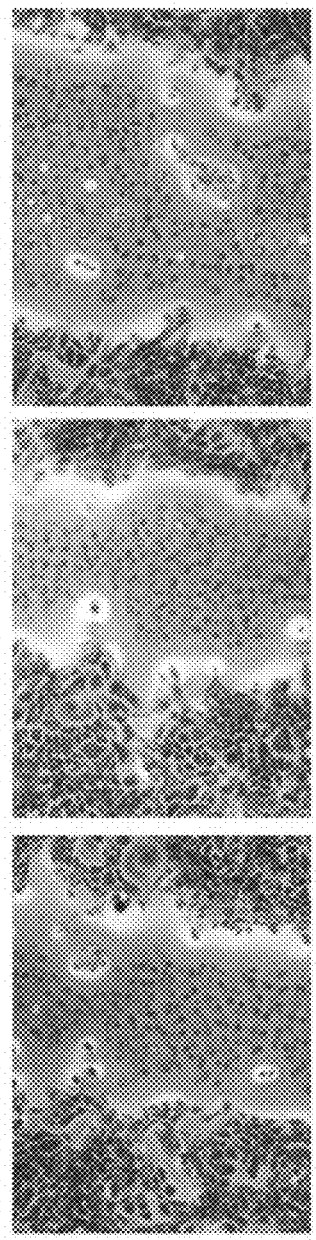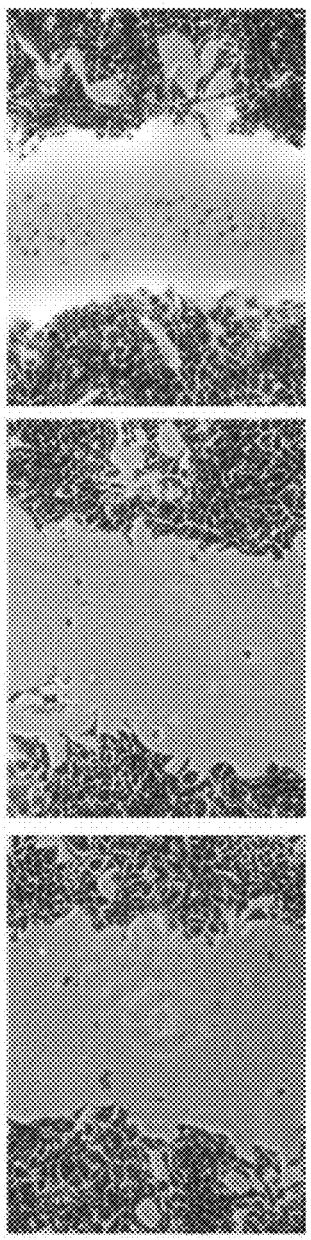

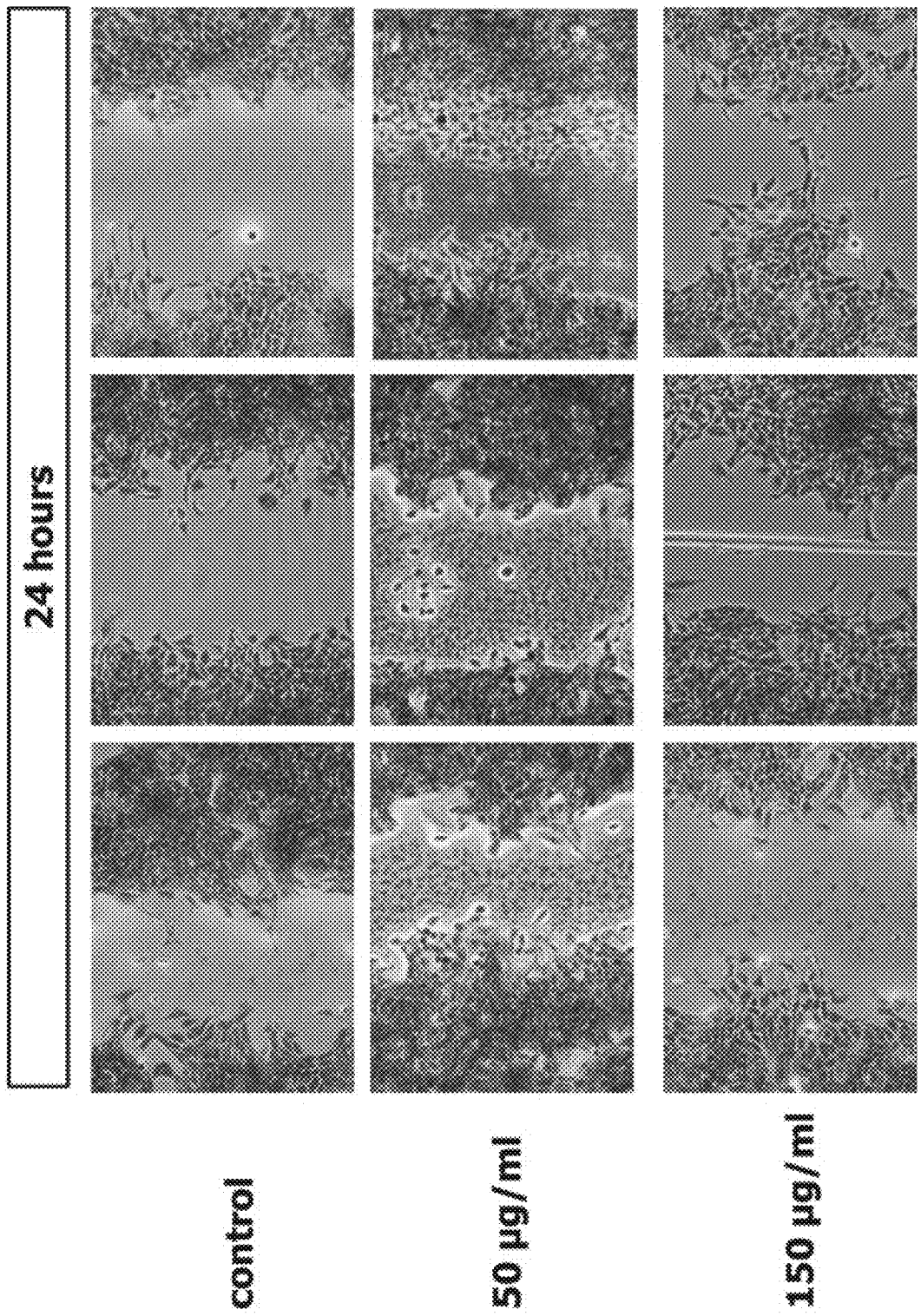

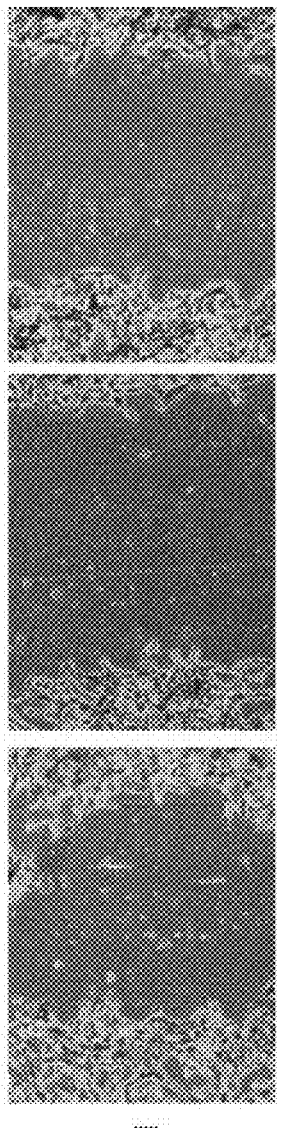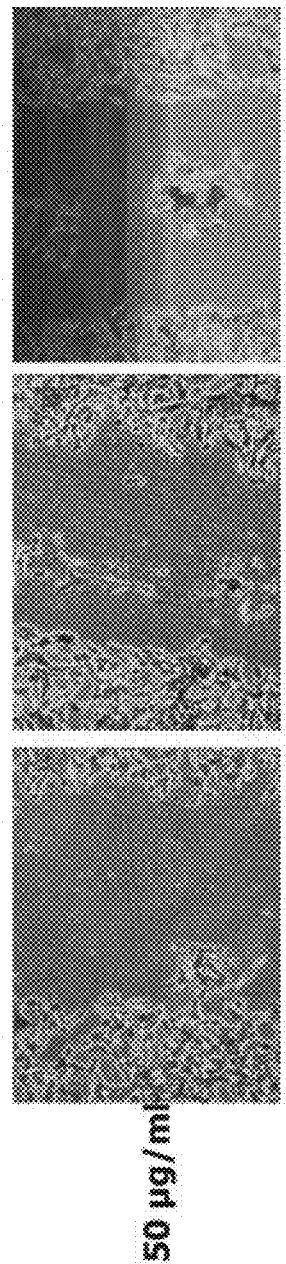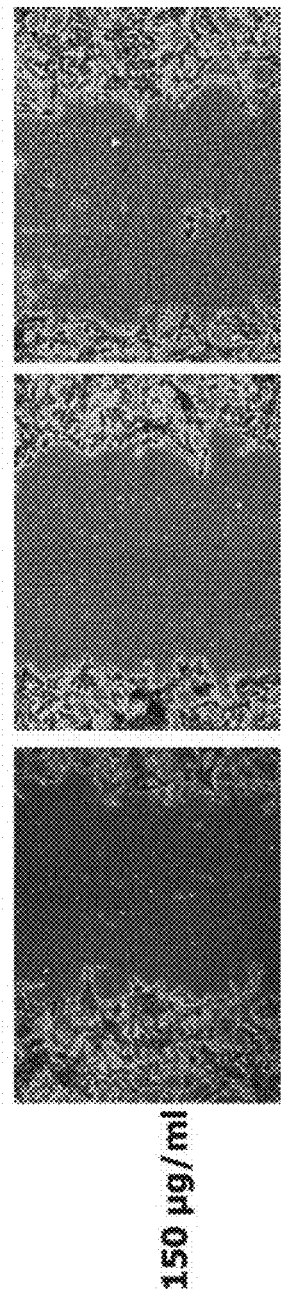

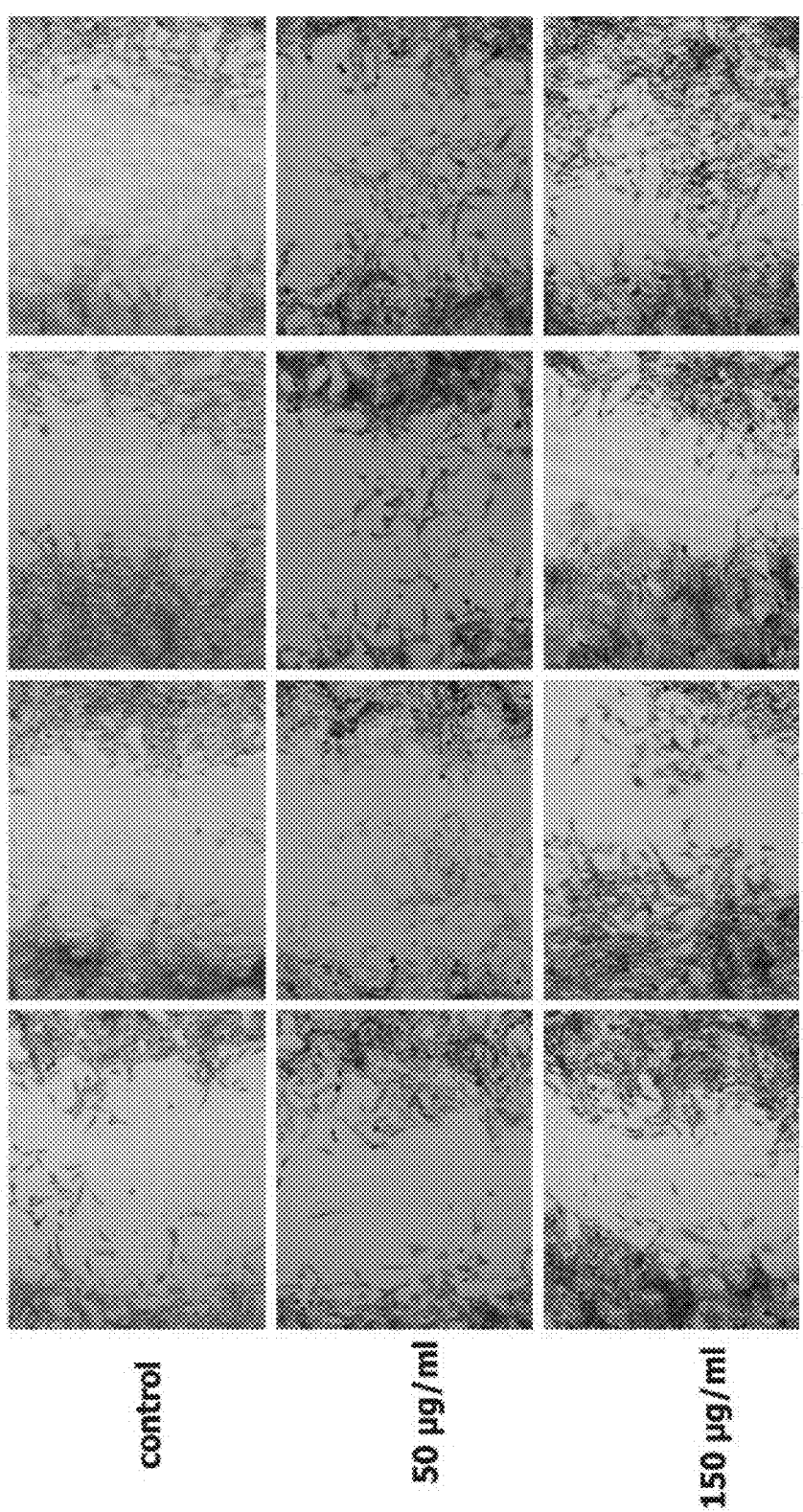

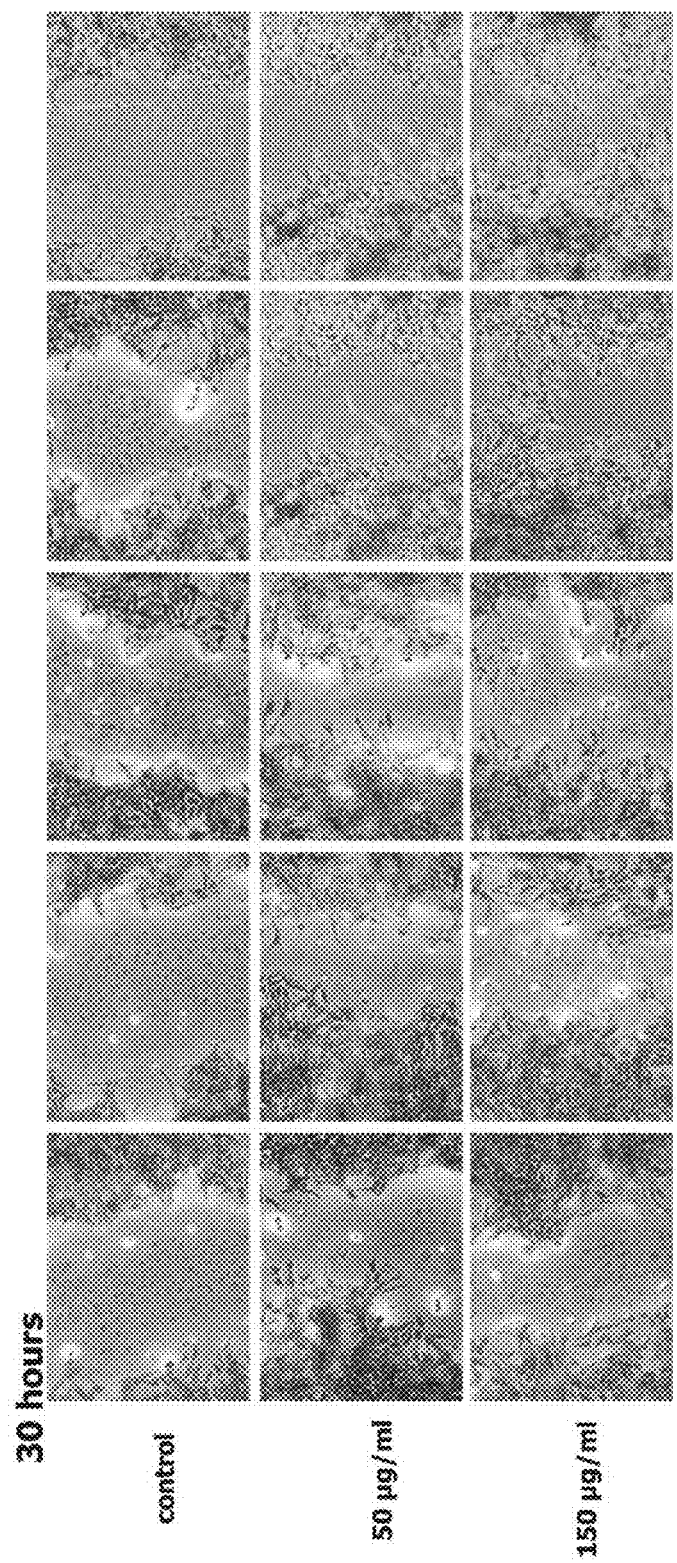

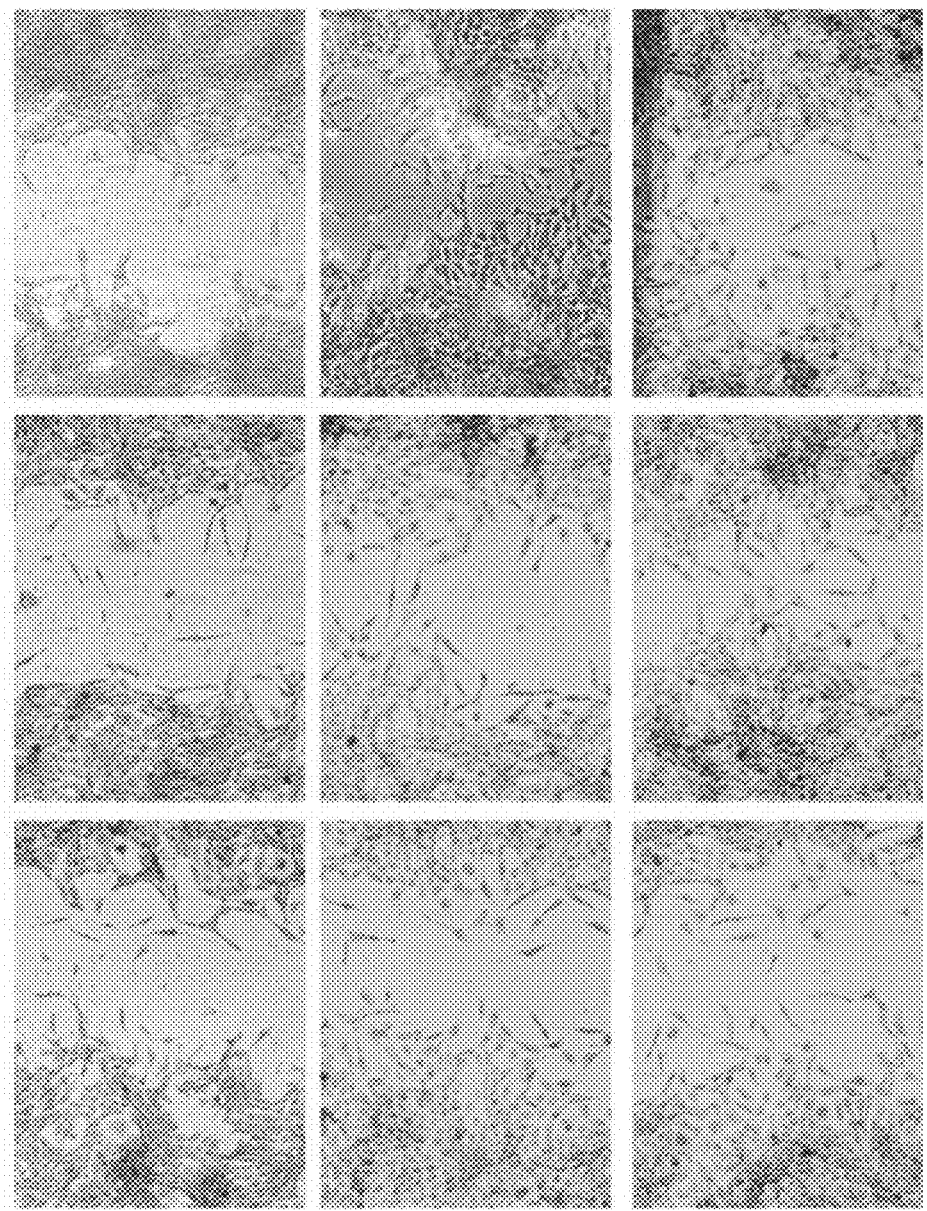

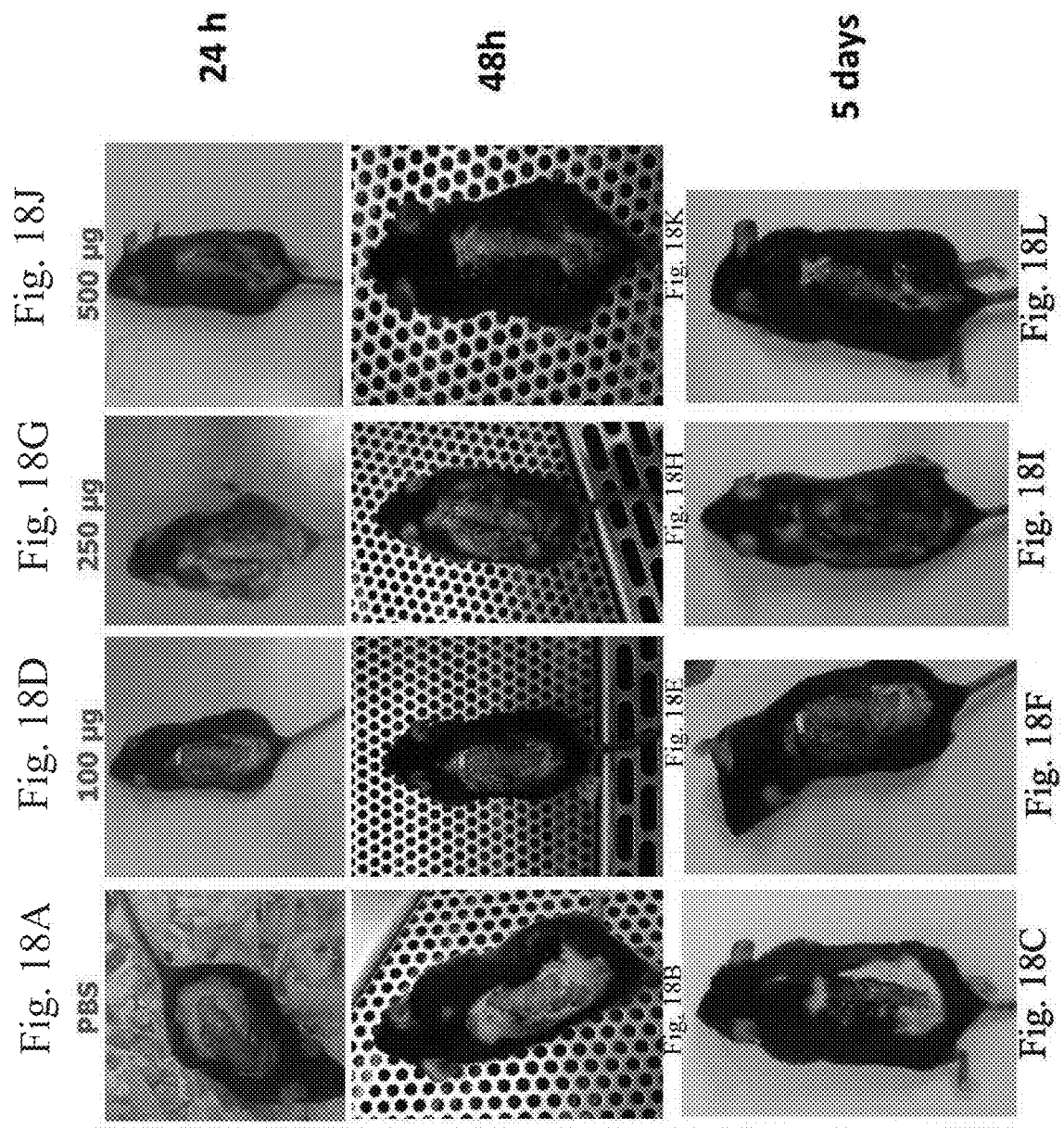

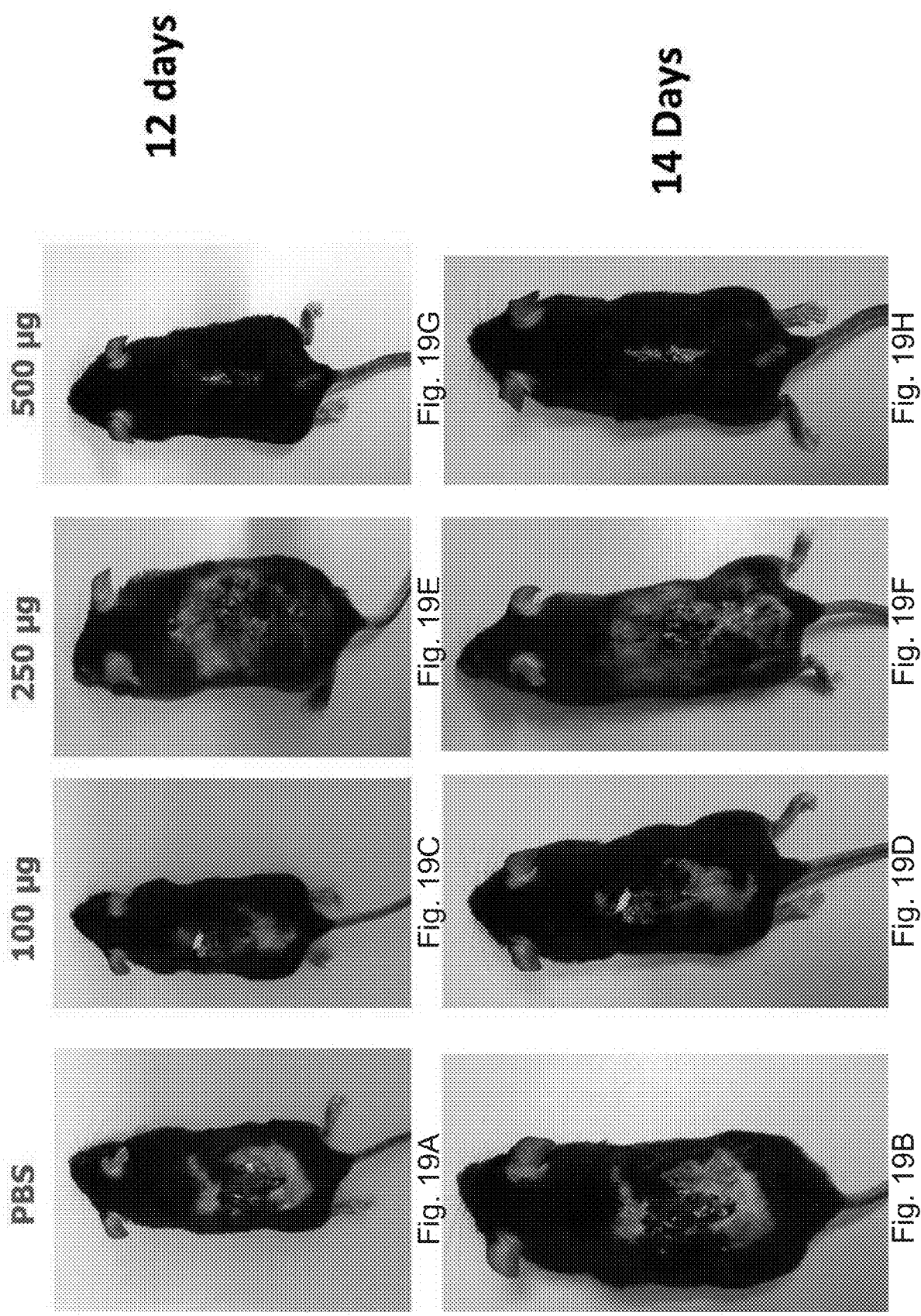

METHODS AND PHARMACEUTICAL COMPOSITIONS FOR IMPROVING WOUND HEALING USING CD24

RELATED APPLICATIONS

This application is a National Phase of PCT Patent Application No. PCT/IL2016/050873 having International filing date of Aug. 10, 2016, which claims the benefit of priority under 35 USC § 119(e) of U.S. Provisional Patent Application No. 62/202,937 filed on Aug. 10, 2015. The contents of the above applications are all incorporated by reference as if fully set forth herein in their entirety.

SEQUENCE LISTING STATEMENT

The ASCII file, entitled 72565SequenceListing.txt, created on Feb. 8, 2018, comprising 55,045 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods and pharmaceutical compositions for improving wound healing in a subject by administering to the subject a therapeutically effective amount of CD24, and more particularly, but not exclusively, to methods of improving wound healing by topical administration of CD24.

Healthy individuals rarely have problems with wound healing. Most skin lesions heal rapidly and efficiently within one to two weeks (1). However, many medical and surgical complications can be attributed to deficiencies in wound repair. Thus, in many cases, although the wounds are healed, the outcome is neither esthetically nor functionally perfect (2). In the U.S. alone, 35 million cutaneous wounds require major intervention annually (2). Open wounds have lost the barrier that protects tissues from bacterial invasion and allows the escape of vital fluids. Without expeditious healing, infections become more frequent.

Normal wound healing is a complex, dynamic and fragile process that is impacted by many factors and is divided into three phases, inflammatory, proliferative and maturation or remodeling (3, 4). After an initial wound, a fibrin clot is formed. In the inflammatory phase, debris and bacteria undergo phagocytosis and removal. Cytokines are released to initiate the proliferative phase. This process manifests with chemotaxis, phagocytosis, angiogenesis, epithelization, collagen degradation and remodeling, production of new glycosaminoglycans and wound contraction. Wound healing is a highly regulated interplay between systematic expressed cell types (i.e., neutrophils, macrophages, fibroblasts, keratinocytes, and endothelial cells), extracellular matrix insoluble components and a group of soluble mediators (i.e., growth factors, cytokines, and chemokines) (2, 3, 5).

The healing process begins with an accumulation of neutrophils and monocytes in the damaged tissue to form a first line of defense. Thereafter, macrophages and mast cells emigrate from nearby tissues and the circulation and accumulate in order to initiate the specific immune response. These inflammatory cells are recruited to the wound site by specific chemotactic factors or chemokines (6, 7). Re-epithelialization and granulation tissue formation include migration of cells from the wound edge to fill the wound site. It involves the migration of keratinocytes over the impermanent matrix in order to rebuild a protective layer (8).

Rapid changes in the extracellular matrix (ECM) occur during the healing process. The fibrin clot is replaced by fibronectin and hyaluronan and subsequently by type I and III collagen (1). The contribution of each component to the wound repair process is difficult to assess due to the complexity of cells involved in the healing.

CD24 plays an important role in the adaptive immune response and controls an important genetic checkpoint for homeostasis and autoimmune diseases in both mice and humans. The CD24 gene encodes a heavily glycosylated cell surface protein anchored to the membrane by phosphatidylinositol (6). Human CD24 consists of 31 amino acids with 16 potential O-glycosylation and N-glycosylation sites. Owing to this extensive glycosylation, CD24 has mucin-like characteristics (9). It plays a crucial role in cell selection and maturation during hematopoiesis and is expressed mainly on premature lymphocytes and certain epithelial and neural cells (10, 11). CD24 can function as an alternative ligand for P-selectin, an adhesion receptor on activated endothelial cells and platelets (12-14).

CD24 has been previously shown to play an important role in the inflammation (15) process. Previous studies by the present inventors also showed that overexpression of CD24 increased proliferation, and migration rates in vitro (16-18).

SUMMARY OF THE INVENTION

According to an aspect of some embodiments of the present invention there is provided a method of improving wound healing in a subject in need thereof, the method comprising administering to the subject a therapeutically effective amount of CD24, thereby improving wound healing in the subject.

According to an aspect of some embodiments of the present invention there is provided a method of improving wound healing in a subject in need thereof, the method comprising topically administering to a wounded area of the subject a therapeutically effective amount of CD24, thereby improving the wound healing in the subject.

According to an aspect of some embodiments of the present invention there is provided a pharmaceutical composition suitable for topical administration, comprising CD24 being in a formulation with a surfactant and a pharmaceutically acceptable carrier.

According to an aspect of some embodiments of the present invention there is provided a therapeutically effective amount of CD24 for use in a method of improving wound healing in a subject in need thereof.

According to an aspect of some embodiments of the present invention there is provided a use of a therapeutically effective amount of CD24 for the manufacture of a medicament identified for improving wound healing.

According to an aspect of some embodiments of the present invention there is provided a cosmetic method of improving wound healing in a subject in need thereof, the method comprising administering to the subject a therapeutically effective amount of CD24, thereby improving wound healing in the subject.

According to an aspect of some embodiments of the present invention there is provided a cosmetic method of improving wound healing in a subject in need thereof, the method comprising topically administering to a wounded area of the subject a therapeutically effective amount of CD24, thereby improving the wound healing in the subject.

According to some embodiments of the invention, the CD24 is injected to the subject.

According to some embodiments of the invention, the CD24 is applied directly on a wounded area of the subject.

According to some embodiments of the invention, the CD24 is applied by dropping a composition comprising the CD24 on the wounded area of the subject.

According to some embodiments of the invention, the CD24 is comprised in a medical dressing (e.g., a bandage).

According to some embodiments of the invention, the CD24 is soaked or impregnated in the medical dressing.

According to some embodiments of the invention, the administering the CD24 is by in vivo gene therapy.

According to some embodiments of the invention, the CD24 is comprised in a pharmaceutical composition.

According to some embodiments of the invention, the CD24 is formulated with a surfactant in the pharmaceutical composition.

According to some embodiments of the invention, the surfactant is an ionic surfactant.

According to some embodiments of the invention, the surfactant is a non-ionic surfactant.

According to some embodiments of the invention, the CD24 is comprised in a lentiviral construct.

According to some embodiments of the invention, the CD24 is comprised in the lentiviral pHR'CMV-HSA vector, wherein the mouse HSA coding sequence is replaced with the human CD24 coding sequence.

According to some embodiments of the invention, wherein a concentration of the CD24 in the pharmaceutical composition is between about 1% to about 10% (volume/volume) of a purified CD24 solution.

According to some embodiments of the invention, wherein a concentration of the CD24 in the pharmaceutical composition is about 10% (volume/volume) of a purified CD24 solution.

According to some embodiments of the invention, the CD24 is glycosylated.

According to some embodiments of the invention, the CD24 comprises a native glycosylation pattern.

According to some embodiments of the invention, the CD24 is non-glycosylated.

According to some embodiments of the invention, the CD24 is soluble.

According to some embodiments of the invention, the CD24 is non-soluble.

According to some embodiments of the invention, the CD24 is conjugated to a lipid moiety.

According to some embodiments of the invention, the CD24 is conjugated to a GPI (Glycosylphosphatidylinositol) moiety.

According to some embodiments of the invention, the pharmaceutical composition is suitable for topical application.

According to some embodiments of the invention, the pharmaceutical composition is comprised in an emulsion carrier, a cream, an ointment, an aqueous solution, a lotion or an aerosol.

According to some embodiments of the invention, the pharmaceutical composition is comprised in an emulsion carrier.

According to some embodiments of the invention, the pharmaceutical composition is comprised in a cream.

According to some embodiments of the invention, the pharmaceutical composition is comprised in an ointment.

According to some embodiments of the invention, the pharmaceutical composition is comprised in an aerosol.

According to some embodiments of the invention, the pharmaceutical composition is comprised in an aqueous solution.

According to some embodiments of the invention, the pharmaceutical composition is comprised in a lotion.

According to some embodiments of the invention, the emulsion carrier is an oil-in-water, water-in-oil, water-in-oil-in-water, and/or oil-in-water-in-silicone emulsion.

According to some embodiments of the invention, the wound is a cutaneous wound.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A-G show that wound closure of full-thickness wounds is delayed in HSA$^{-/-}$ mice as compared to WT mice. Wounds were introduced to the mice as described in the Examples section and the wounds were either stitched or remained unstitched. The left picture in each panel represents the HSA$^{+/+}$ mouse while the right is for the HSA$^{-/-}$. FIG. 1A: t=0 hours; FIG. 1B: t=0 hours; the wounds were stitched; FIG. 1C: t=24 hours; FIG. 1D: t=24 hours, with stitches; FIG. 1E: t=7 days; FIG. 1F: t=7 days, with stitches; FIG. 1G: Histogram depicting fold change of wound area [KO (knockout of HSA) versus WT (wild type of HSA)].

Figure 2A:
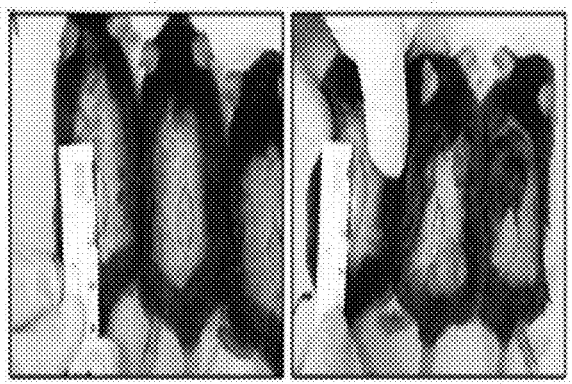
Figure 2C:
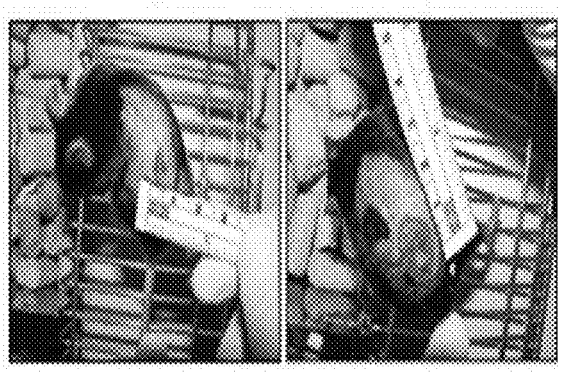
Figure 2B:
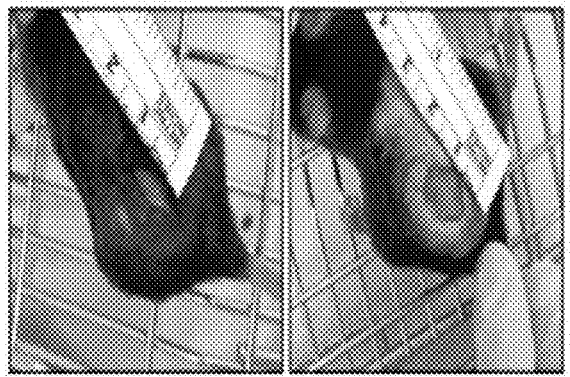
Figure 2D:
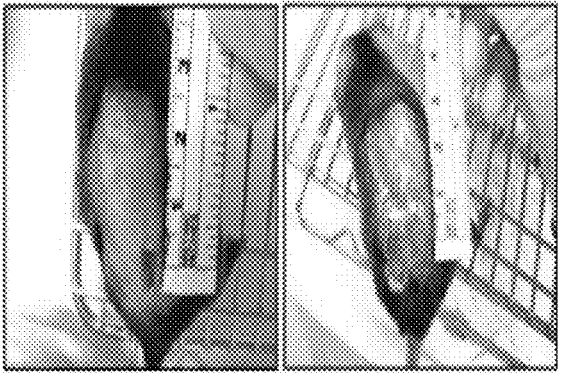
Figure 2E:
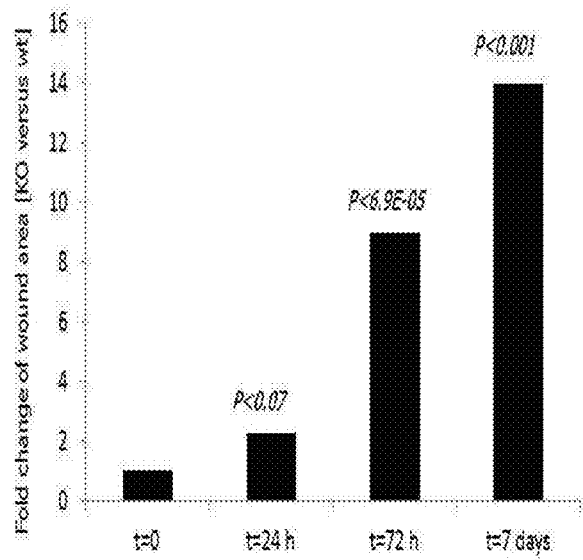

FIG. 2A-E show that wound closure of bigger full-thickness wounds is faster in HSA+/+ mice as compared to HSA$^{-/-}$ mice. Wounds were introduced to the mice as described in the Examples section. The left picture in each panel represents the HSA$^{+/+}$ mouse while the right is for the HSA$^{-/-}$. FIG. 2A: t=0 hours; FIG. 2B: t=24 hours. FIG. 2C: t=72 hours; FIG. 2D: t=7 days; FIG. 2E: depicting fold change of wound area (KO versus WT).

Figure 3A:
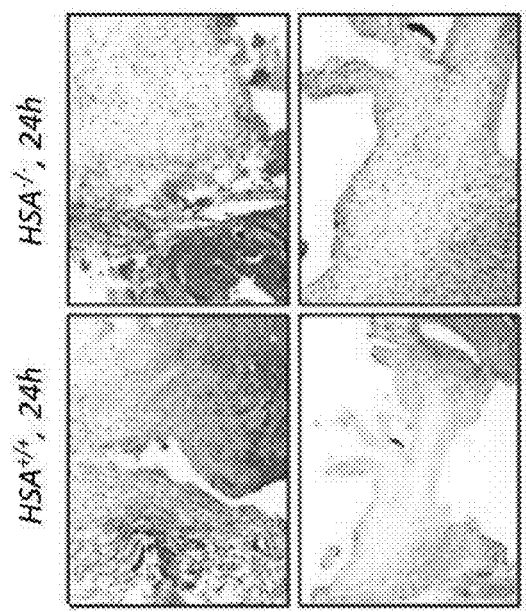
Figure 3B:
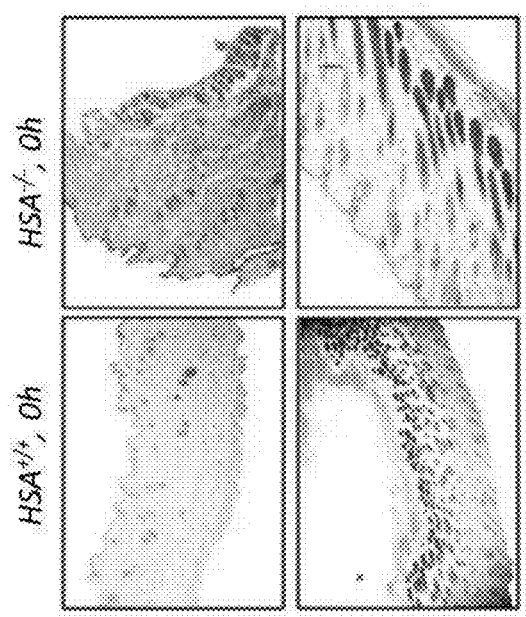
Figure 3C:
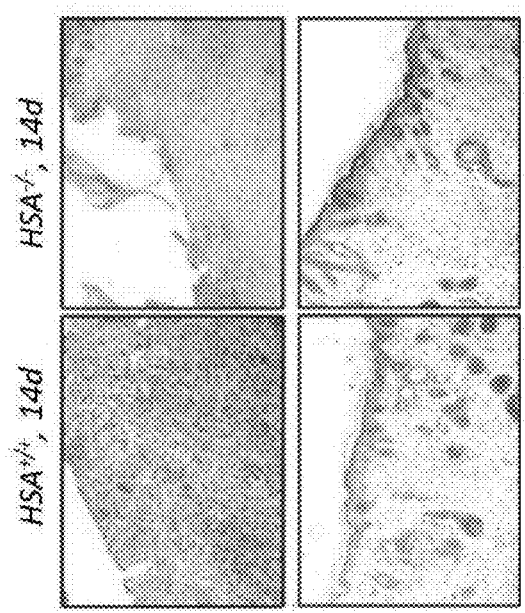

FIG. 3A-C depict histological stains. The left images in each panel represents the HSA$^{+/+}$ mice while the right images represent the HSA$^{-/-}$. FIG. 3A: T=0 hours; FIG. 3B: T=72 hours; FIG. 3C: T=2 weeks. Tissue sections were stained with Hematoxylin and Eosin (H&E) and visualized on an Olympus AH light microscope at 400× magnification.

Figure 4A:
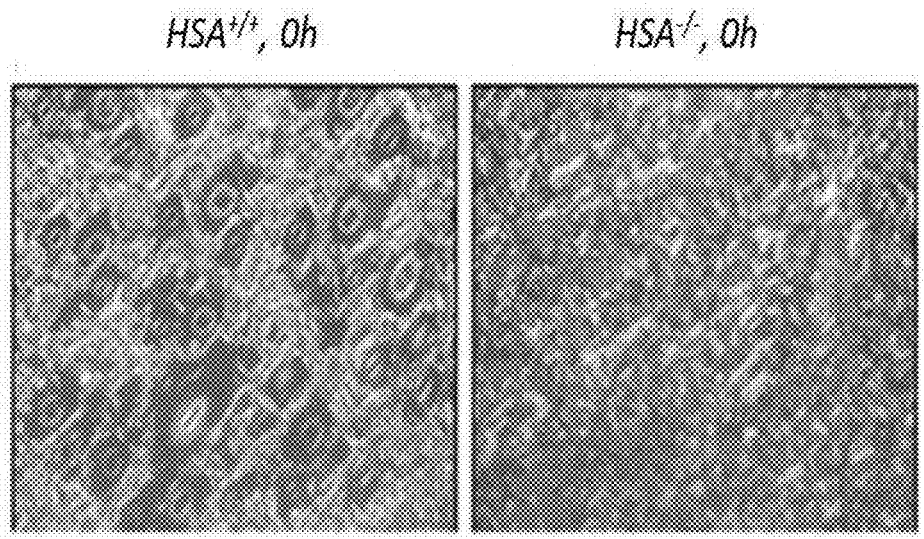
Figure 4B:
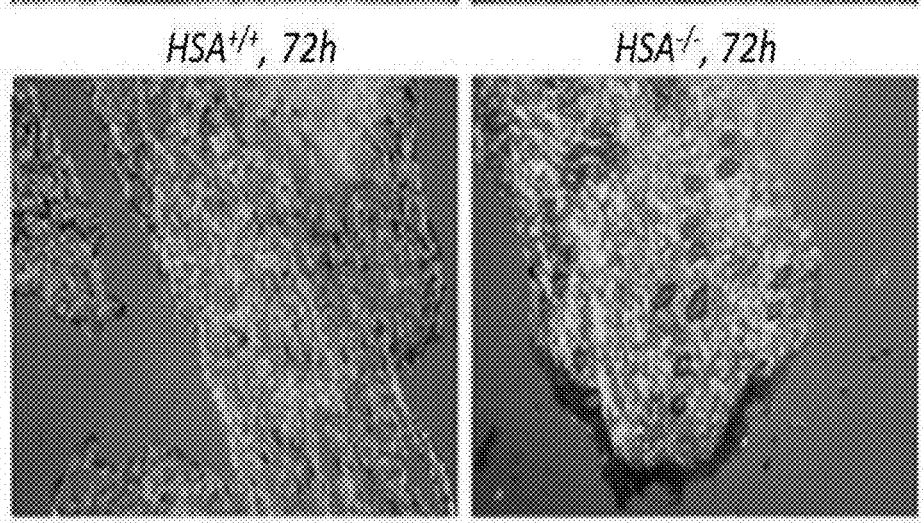
Figure 4C:
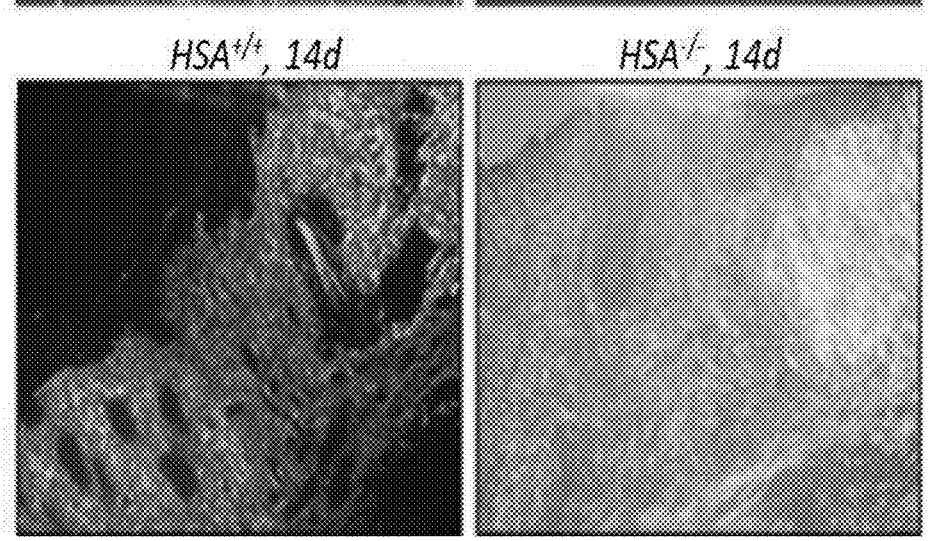

FIG. 4A-C depict collagen stains. The left image in each panel represents the HSA$^{+/+}$ mouse while the right image is for the HSA$^{-/-}$. FIG. 4A: t=0 hours; FIG. 4B: t=72 hours; FIG. 4C: t=14 days. Tissue sections were stained with NovaUltra™ Picro-Sirius Red stain and visualized on an Olympus AH light microscope at 400× magnification.

Figure 22:
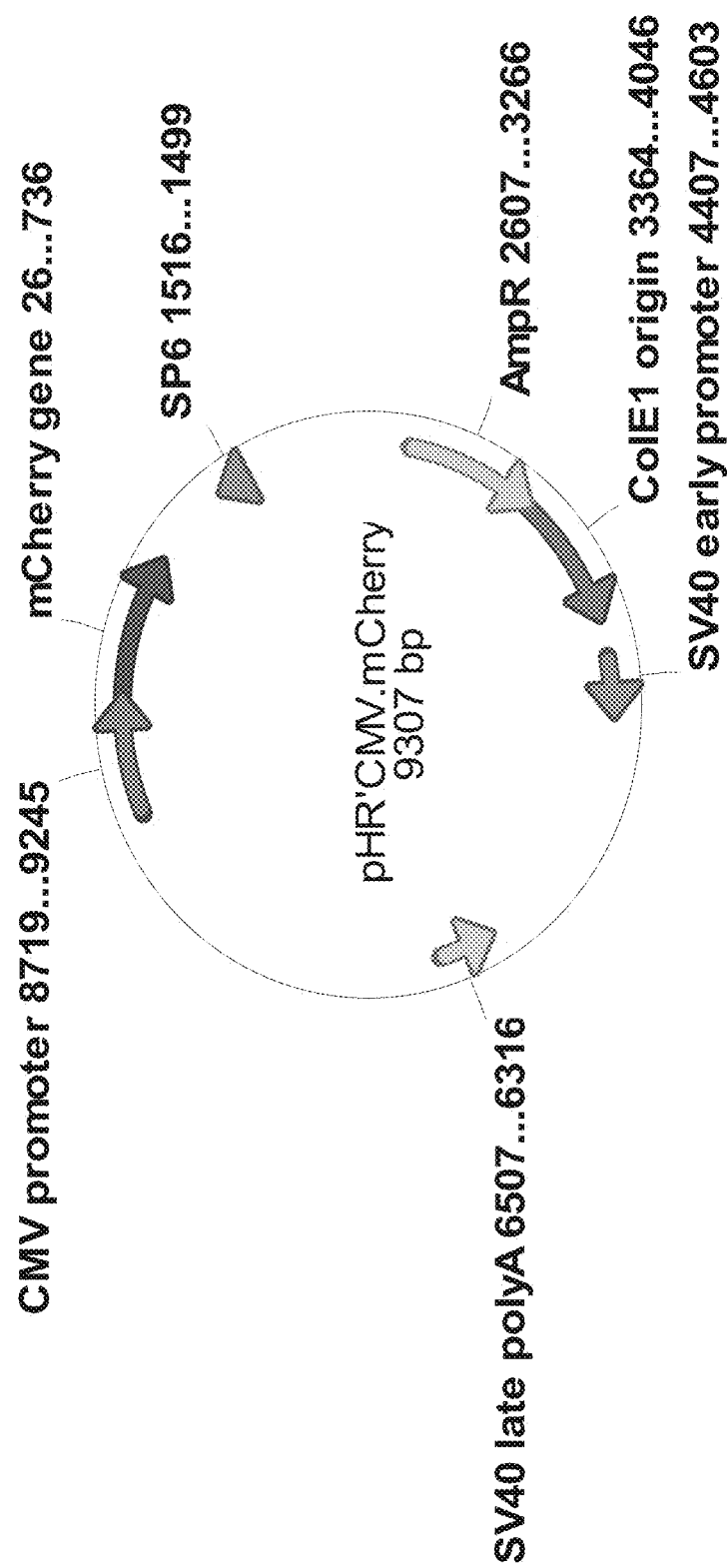

FIG. 5A-D depict the production of HIV-based viruses for gene delivery. FIG. 5A—HEK 293T cells were co-transfected with the mentioned plasmids (mCherry-encoded viruses as depicted in FIG. 22) and after 48 hours the expression of the transgene was evaluated by the mCherry marker. FIG. 5B—The infectivity of the virions, which were produced by the HEK293T helper cells, was tested on NIH-3T3 in vitro by fluorescence microscope (mCherry expression). FIG. 5C—72 hours after the infection, cell lysates were prepared and 20 µg of total proteins was loaded. HSA was detected with the anti-HSA mAb, M1.69, and then the membrane was reprobed with anti-human tubulin. FIG. 5D depicts results of a flow cytometry analysis. $1 \times 10^6$ infected cells were incubated with 10 µg/ml of M1.69 for 30 minutes at room temperature (RT). FITC-labeled goat anti-rat antibody was used for the detection of bound antibody. The red curve represents the negative control (secondary antibody alone) and the green curve represents the binding of M1.69.

FIG. 6A-C depict imaging of the living organism. The viruses were injected or dropped into the wounded cells on T=0 hours. 96 hours after injection (FIG. 6A)/dropping (FIG. 6B-C) of the mCherry-encoded viruses (n=3), mice were taken to in vivo imaging to detect the mCherry expression in the wounded cells using the Cri Maestro device, which enables multiplexed in vivo fluorescence imaging of small animals with high sensitivity. Light images are shown on the upper panels and fluorescent images are shown on the lower panels.

FIG. 7A-G depict re-expression of HSA. FIG. 7A—The viruses were injected or dropped into the wounded cells on T=0 ours; FIG. 7B—$HSA^{-/-}$ mice 24 hours after mCherry-encoded viruses injection (left panel) or dropping (right panel); FIG. 7C—$HSA^{-/-}$ mice 24 hours after HSA encoded viruses injection (left panel) or dropping (right panel); FIG. 7D—$HSA^{+/+}$ mice 24 hours after mCherry-encoded viruses injection (left panel) or dropping (right panel); FIG. 7E—$HSA^{+/+}$ mice 24 hours after mCherry-encoded viruses injection (left panel) or dropping (right panel); FIG. 7F—7 days after viruses injection. FIG. 7G—a histogram depicting the wounded area in several time points.

Figure 8A:
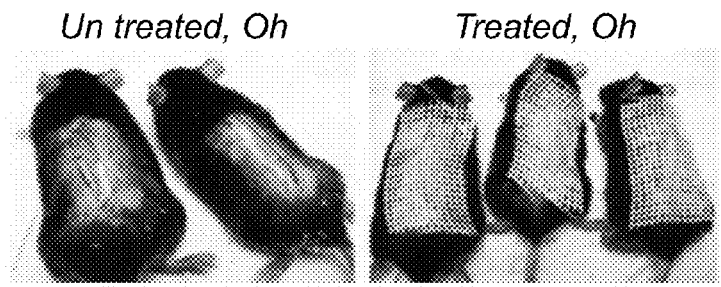
Figure 8B:
Figure 8C:
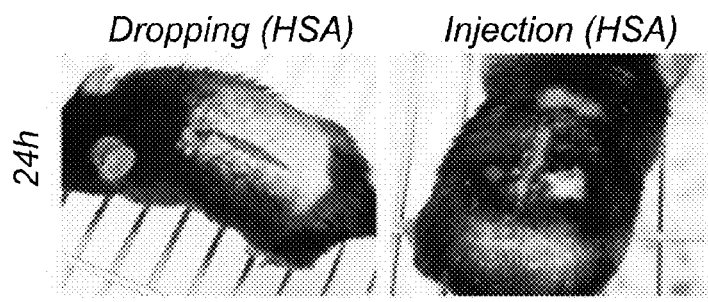
Figure 8D:
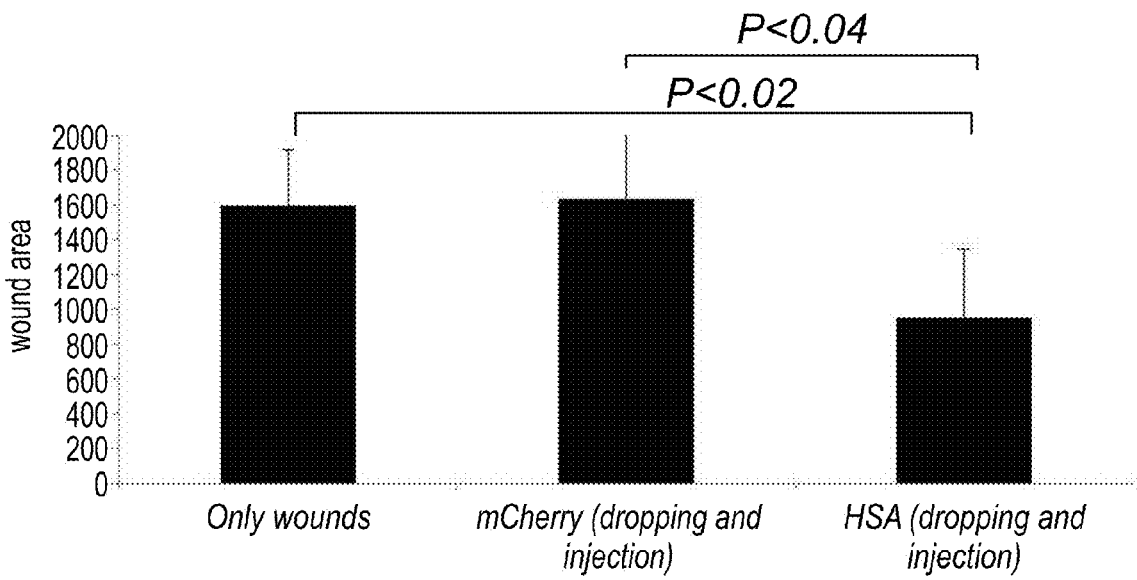

FIG. 8A-D depict acceleration of wound healing upon over expression of HSA. FIG. 8A—The wounds were infected with the viruses (right panel) or left un-treated (left panel) on T=0 hours; FIG. 8B—$HSA^{+/+}$ mice 24 hours after the injury (left panel), 24 hours after infection, by dropping, with the mCherry-encoded viruses (middle panel), 24 hours after mCherry-encoded viruses injection (right panel); FIG. 8C—$HSA^{+/+}$ mice 24 hours after infection, by dropping (left panel) or injection (right panel), with the HSA-encoded viruses; FIG. 8D—a histogram depicting wounded area in mice after several treatments.

FIG. 9A-E depict that the rapid healing does not depend on mice strain. Four groups of four mice were used in this study. Two of them were of C57/Bl while the other two were of Balb/c. The mice in one group from each strain were injected with the HSA-encoded viruses while the other group with the mCherry-encoded viruses. FIG. 9A—$HSA^{+/+}$ mice 24 hours after mCherry-encoded viruses injection; FIG. 9B—$HSA^{+/+}$ mice 24 hours after HSA-encoded viruses injection; FIG. 9C—$HSA^{+/+}$ mice 48 hours after mCherry-encoded viruses (the two pictures on the left) and HSA-encoded viruses injection (the two pictures on the right); FIG. 9D—$HSA^{+/+}$ mice 6 days after mCherry-encoded viruses (the two pictures on the left) and HSA-encoded viruses injection (the two pictures on the right). FIG. 9E—a histogram depicting the wounded area after several treatments.

FIG. 10A-B depict human CD24 constructs according to some embodiments of the invention. FIG. 10A depicts the sequence encoding the full length human CD24. Color index: purple highlight—DNA encoding signal peptide; yellow highlight—DNA encoding core protein; green highlight—DNA encoding C-terminus. "TAA"—stop codon. FIG. 10B depicts the sequence encoding the soluble human CD24. Index (colors and underlines): purple highlight—DNA encoding signal peptide; Red letters—intron sequence; underlined sequences—sites for restriction enzymes; Green letters—DNA encoding a flexible linker; Purple letters—DNA encoding Tev protease cleavage site; Yellow highlight—DNA encoding core protein; Blue letters—DNA encoding a 6×HIS tag. "TGA"—stop codon.

Figure 11A:
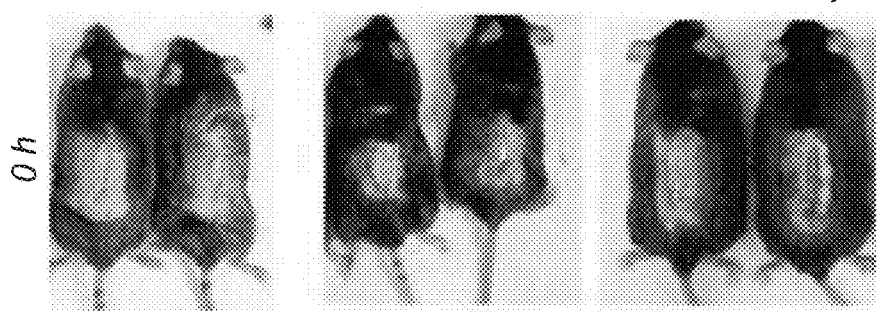
Figure 11B:
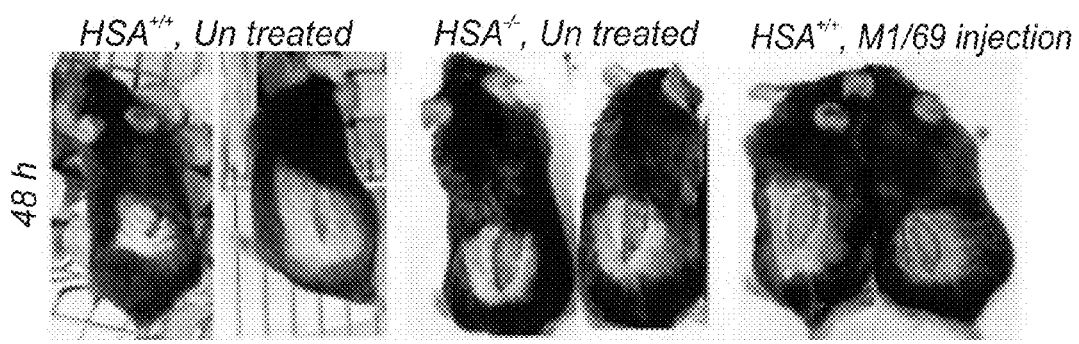
Figure 11C:
Figure 11D:
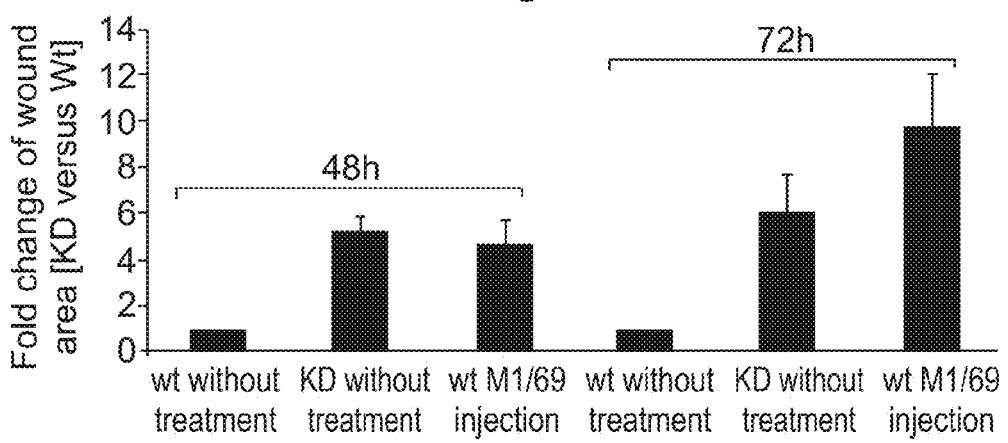

FIG. 11A-D depict delayed wound healing upon down regulation of HSA expression. FIG. 11A—The wounds were treated by topical administration (by injection into the wound border) of an anti-HSA antibody ("M1/69"; right panel) or were left un-treated (left and middle panel) on T=0 hours; FIG. 11B—$HSA^{+/+}$ (left panel) and $HSA^{-/-}$ (middle panel) mice 48 hours after the injury and $HSA^{+/+}$ mice 48 hour after antibody injection (right panel); FIG. 11C—$HSA^{+/+}$ (left panel) and $HSA^{-/-}$ (middle panel) mice 72 hours after the injury and $HSA^{+/+}$ mice 72 hours after antibody injection (right panel); FIG. 11D—A representative plot of the statistical differences, in size of wound area, between the groups.

FIG. 12A-C depict the amino acid sequences of the CD24 core protein (FIG. 12A, SEQ ID NO: 28), the CD24 full length (FIG. 12B, SEQ ID NO:29), and the CD24 soluble protein (FIG. 12C, SEQ ID NO: 30) of some embodiments of the invention. Color index: FIG. 12A—Color index: red letters=CD24 core protein amino acid sequence; FIG. 12B—Color index: Red letters=CD24 core protein amino acid sequence; Light Blue letters=Signal peptide; Green letters=C-terminus; FIG. 12C—Color index: Light Blue letters=Signal peptide; Brown letters=Linker; Red letters=CD24 core protein amino acid sequence; Dark Blue letters=Histidine tag (6×HIS).

Figure 13A:
Figure 13B:
Figure 13C:
Figure 13D:
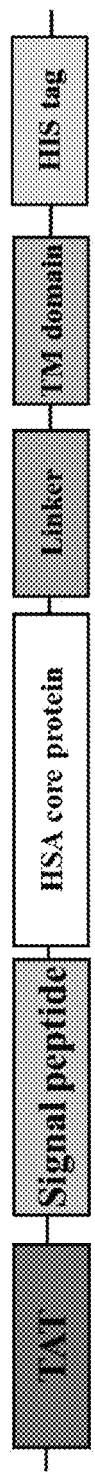
Figure 13E:
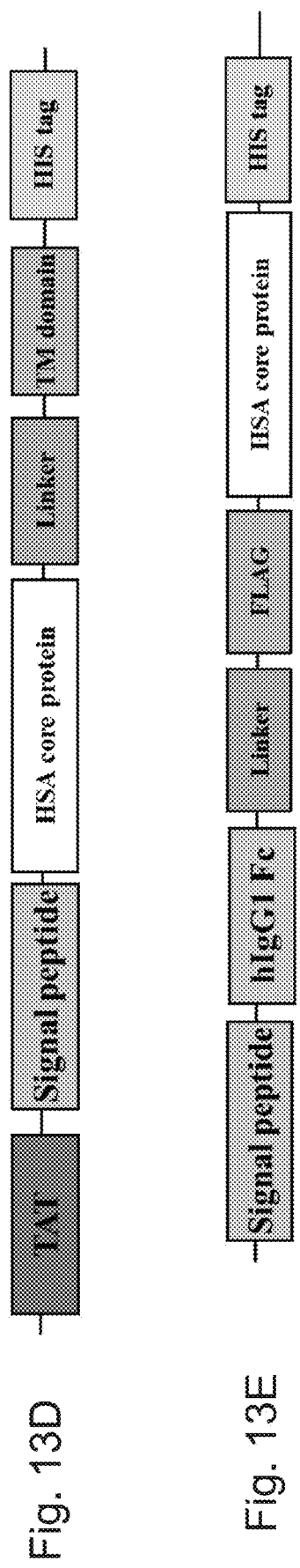

FIG. 13A-E schematically depict nucleic acid constructs which are translatable into different derivatives of the HSA (murine CD24 ("mCD24")) recombinant protein; the core protein fused to Histidine tag (FIG. 13A); the full length mCD24 fused to the Histidine tag and TAT signal (FIG. 13B); the core protein fused to Histidine tag and TAT signal (FIG. 13C); the signal peptide and the core protein of the mCD24 fused to the TAT signal and to a transmembrane domain of the EGFR (FIG. 13D); and the signal peptide and the core protein of the mCD24 fused to a Fc region (FIG. 13E).

Figure 14:
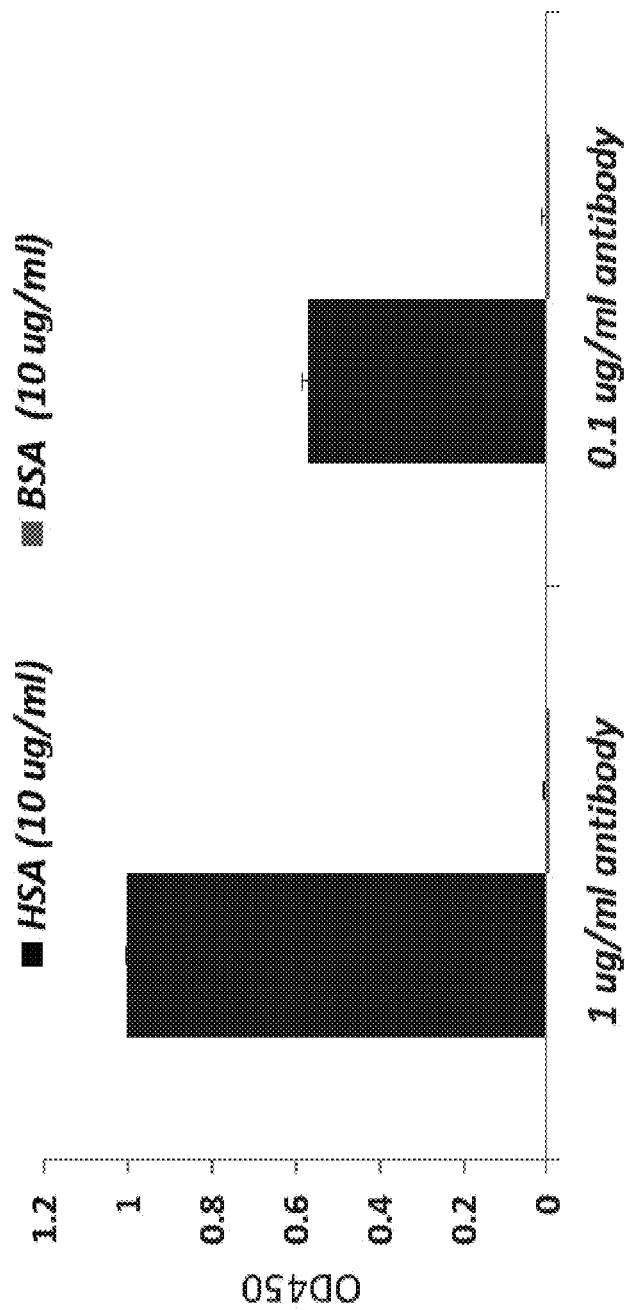

FIG. 14 depicts binding of the recombinant mCD24 protein, which was translated from the construct described in FIG. 13E to the anti-CD24 antibody using an ELISA assay. The results validate recombinant expression of the correct protein.

Figures 15A, 15B:
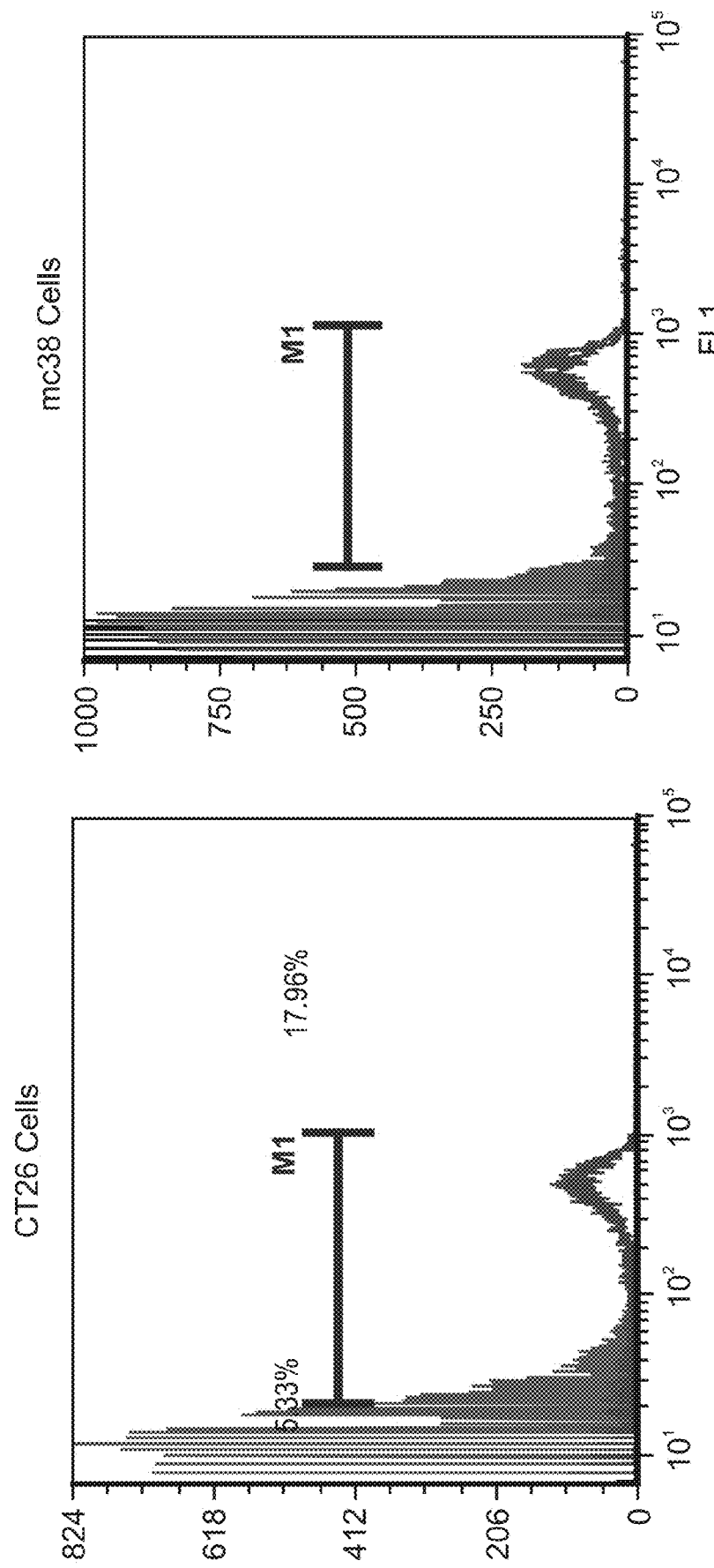
Figure 15C:
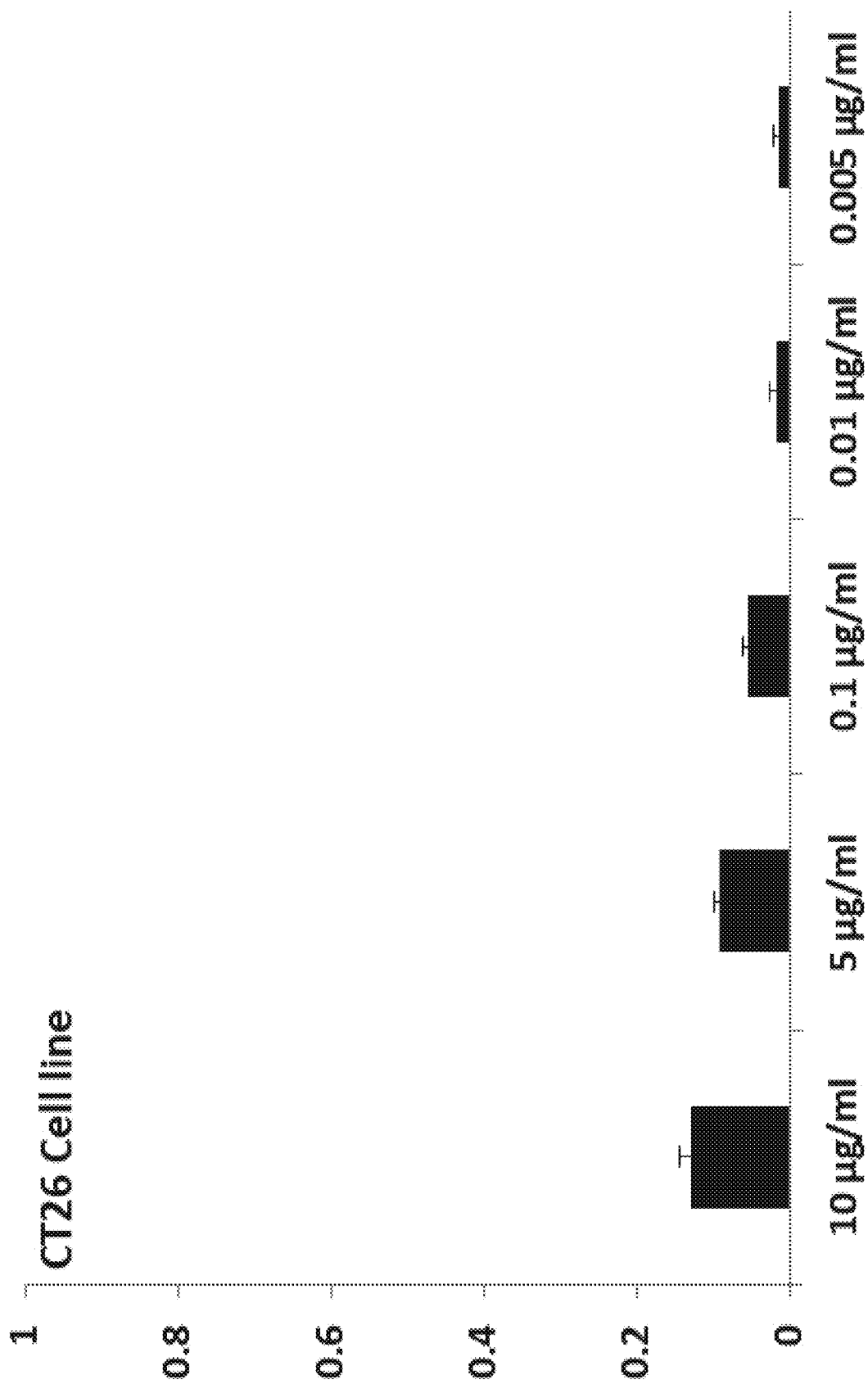
Figure 15D:
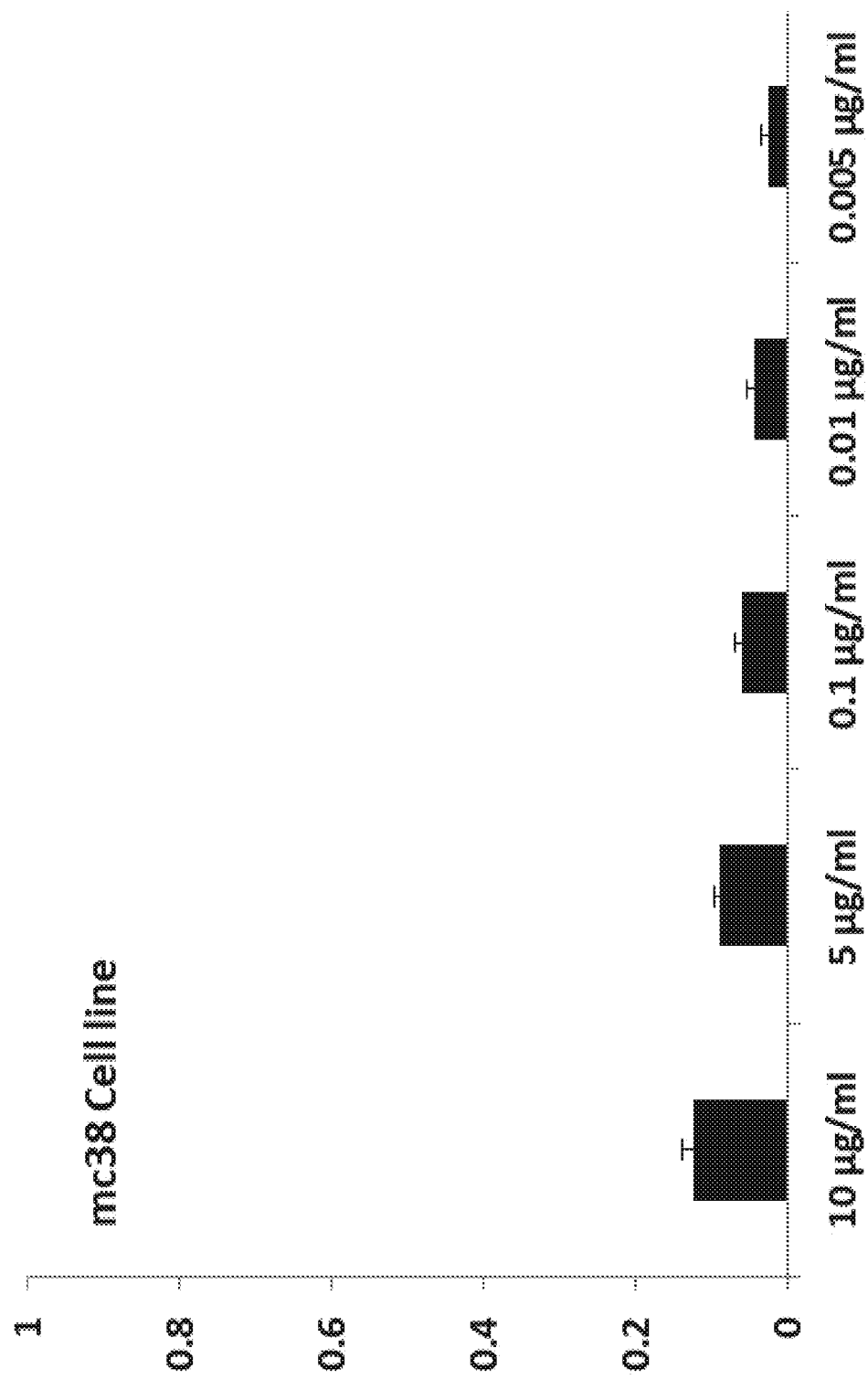

FIG. 15A-D depict an evaluation of mCD24 expression in CT26 and mc38 cell lines by FACS analysis (FIG. 15A-B) and whole-cell ELISA (FIG. 15C-D). FIG. 15A—FACS analysis of CT26 cells with anti-mCD24 antibody and controls; FIG. 15B—FACS analysis of mc38 cells with anti-mCD24 antibody and controls; Color index for FIG. 15A-B: Black lines=Only cells; Red lines=cells incubated only with a secondary antibody; Blue and purple lines=cells incubated with Anti-HSA. FIG. 15C—A histogram depicting whole cell ELISA of the CT26 cell lines with anti-mCD24 antibody; FIG. 15D—A histogram depicting whole cell ELISA of the mc38 cell lines with anti-mCD24 antibody. Note that the levels of HSA in the CT26 and mc38 are low.

Figure 16A:
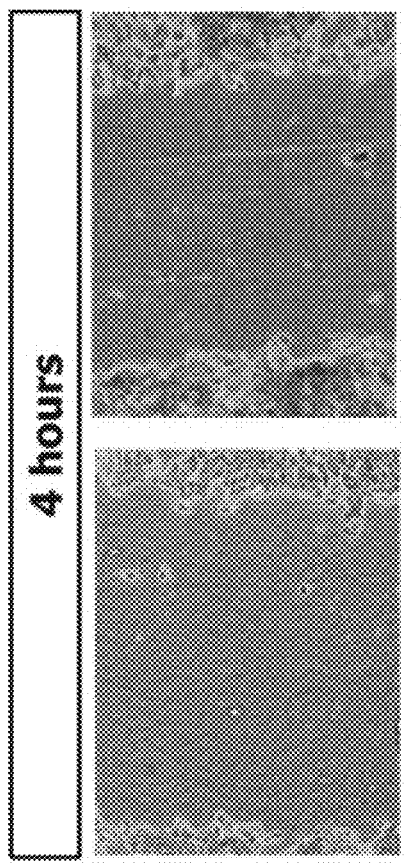
Figure 16B:
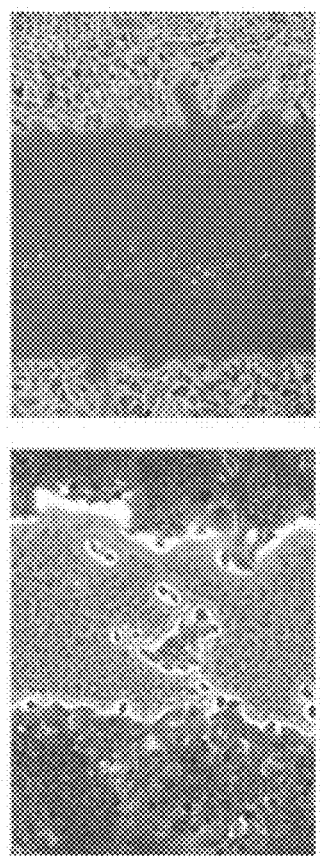
Figure 16C:
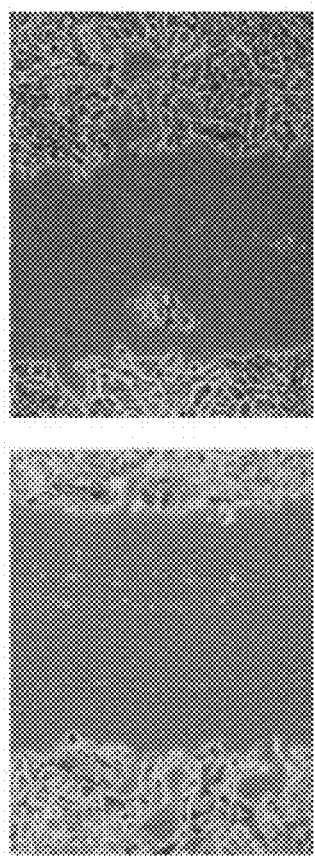

FIG. 16A-I demonstrate the wound healing in vitro bioassay for screening the potential and efficacy of the recombinant CD24 protein which was translated from the construct described in FIG. 13E. Cell monolayer was scraped with a sterile micropipette tip to create a denuded zone (gap) of constant width. 0 µg/ml ("control"), 50 µg/ml and 150 µg/ml of the recombinant proteins were added and cell migration into the cell-free area was evaluated using inverted microscope and gap closure was monitored and photographed at 4 hours (FIG. 16A-C), 8 hours (FIG. 16D-F) and 24 hours (FIG. 16G-I). Shown are representative images at each concentration and time point. Note that upon addition of HSA the gap between the two edges of the cell monolayer (after scraping) is closing faster as compared untreated cells, due to faster cell migration of the cells.

FIG. 17A-L depict the same experiment as described in FIG. 16A-I yet with the following time points: 6 hours (FIG. 17A-C), 24 hours (FIG. 17D-F), 30 hours (FIG. 17G-I) and 48 hours (FIG. 17J-L).

FIGS. 18A-L are images demonstrating the wound healing in vivo assay to evaluate the potential efficacy of the recombinant protein which was translated from the construct described in FIG. 13E (Construct number 5). 4-cm longitudinal full-thickness incisions wounds, including the striated muscle layer, were made on the back of HSA$^{-/-}$ knockout mice. The excised wounds were left open (i.e., without stitches) and were either treated with 100 µg (FIGS. 18D-F), 250 µg (FIGS. 18G-I) and 500 µg (FIGS. 18J-L) of purified HSA protein which was applied once post-wounding (injected into the cells on the wound border), or were subjected to PBS treatment (negative control; FIGS. 18A-C). 24 hours and 48 hours later, the protein at the indicated amounts was further dripped into the wounded area. Shown are the wounds at various time points: 24 hours (FIGS. 18A, D, G and J), 48 hours (FIGS. 18B, E, H and K) and 5 days (FIGS. 18C, F, I and L) from generating the incision wounds. Note the improvement of wound healing in the animals subjected to HSA treatment as compared to control animals (which were not treated with HSA), with faster closure of the wound area and a more esthetically wound closure. It is also noted that higher concentrations of HSA revealed faster closure of wounds, indicating a dose dependent healing process.

FIG. 19A-H—images of mice treated as described in FIG. 18A-L above following 12 days (FIGS. 19A, C, E and G) and 14 days (FIGS. 19B, D, F and H) from generating the incision wounds.

Figure 20:
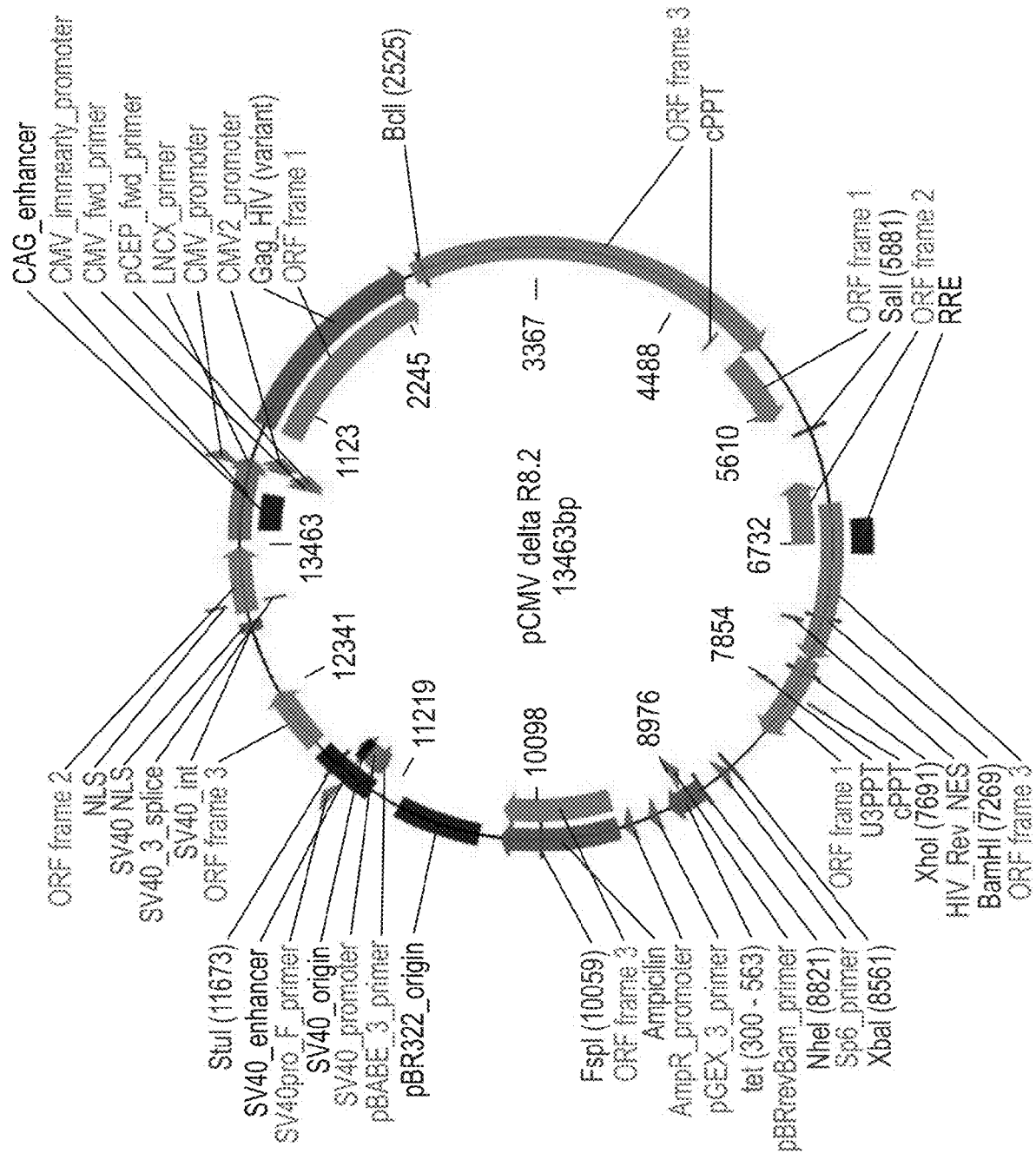

FIG. 20 is a schematic illustration of the pCMV ΔR8.2 nucleic acid construct designed for generation of Gag HIV I and Pol HIV I.

Figure 21:
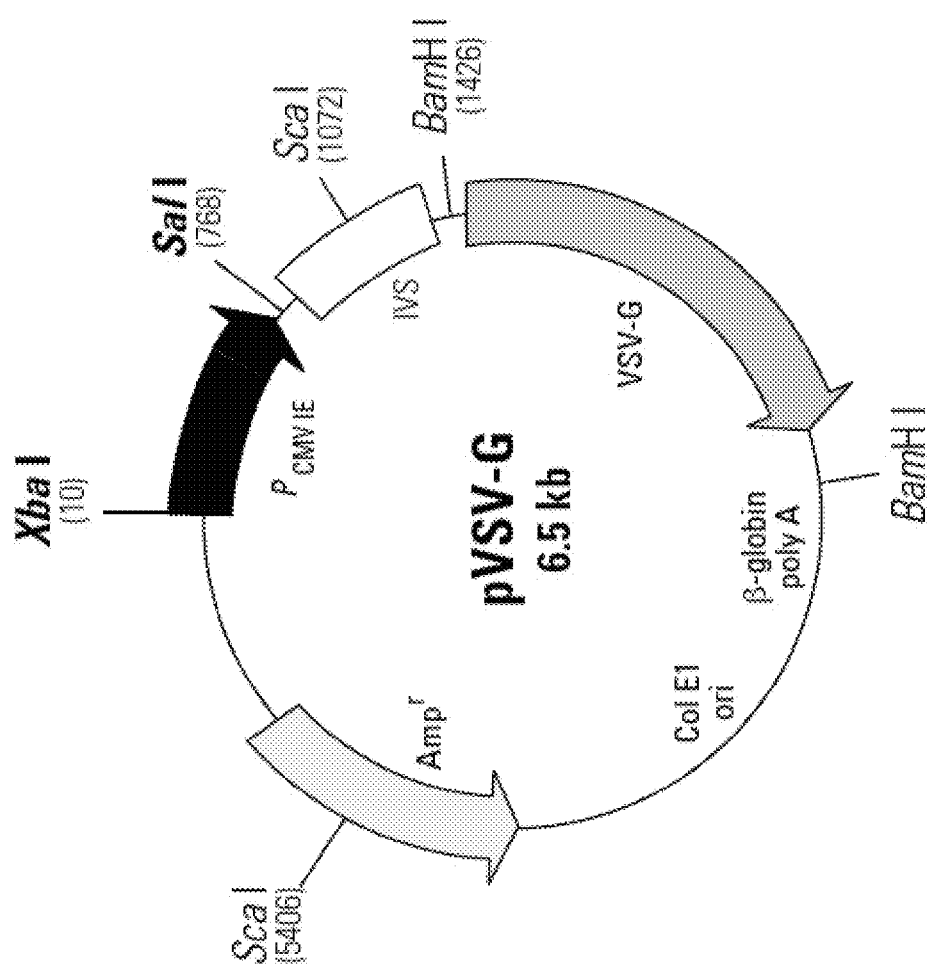

FIG. 21 is a schematic illustration of the pVSV-G nucleic acid construct designed for generation of the virus envelope.

FIG. 22 is a schematic illustration of the pHR'CMV mCherry nucleic acid construct designed for generation of the mCherry control protein under the regulation of the CMV promoter.

Figure 23:
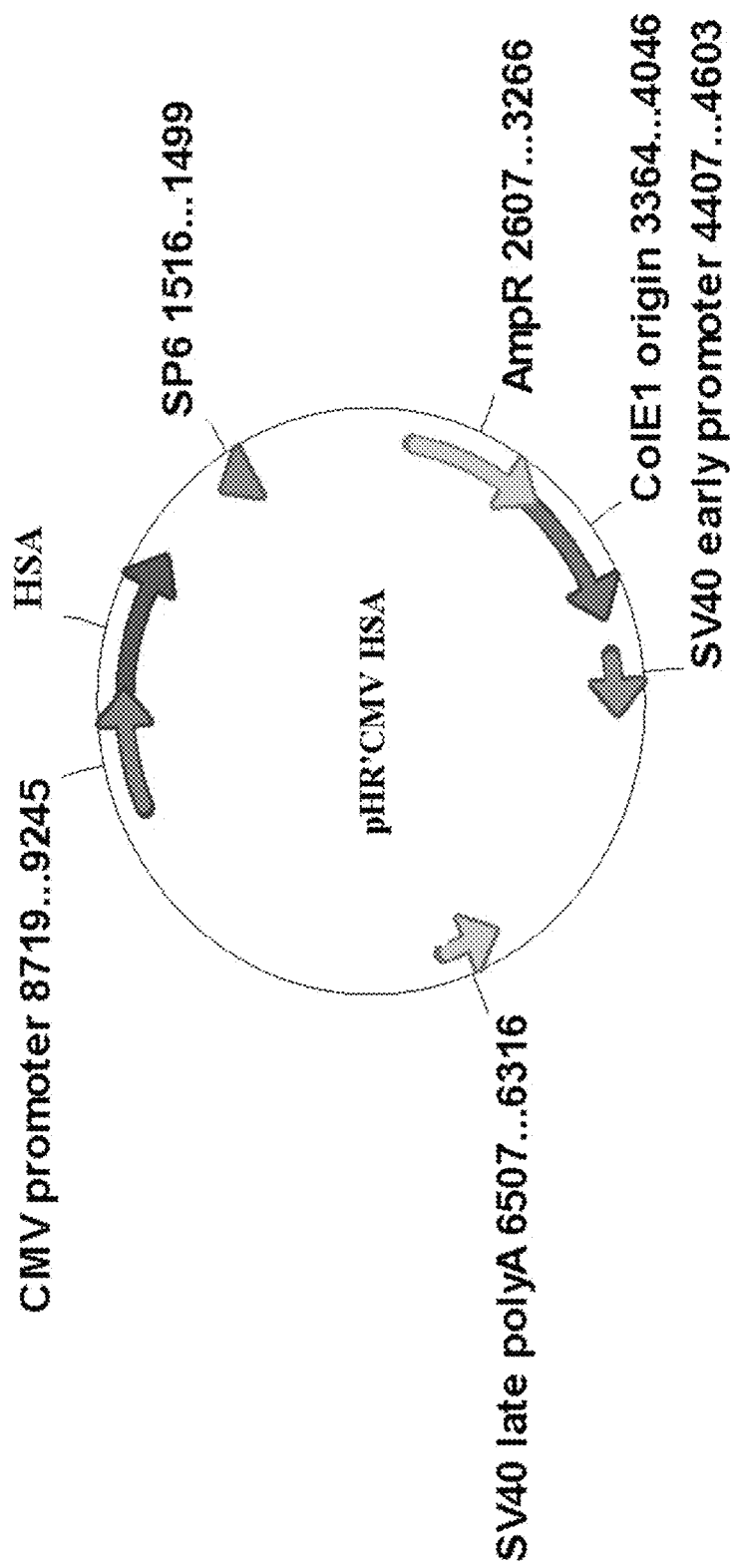

FIG. 23 is a schematic illustration of the pHR'CMV HSA nucleic acid construct designed for generation of the HSA protein under the regulation of the CMV promoter.

DESCRIPTION OF SPECIFIC EMBODIMENTS OF THE INVENTION

The present invention, in some embodiments thereof, relates to methods and pharmaceutical compositions for improving wound healing in a subject by administering to the subject a therapeutically effective amount of CD24, and more particularly, but not exclusively, to methods of improving wound healing by topical administration of CD24.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have uncovered that CD24 has a role in the wound healing process. An excisional model of wound healing was used to study the effect of CD24 on wound healing in genetically modified heat stable antigen (HSA/CD24)-deficient mice (HSA$^{-/-}$) as compared to wild-type (WT) mice. As shown in Tables 1-2, FIGS. 1A-G, 2A-E, 3A-D, and 4A-C and described in Example 1 of the Examples section which follows, large full-thickness skin wounds, excised on the back of HSA$^{-/-}$ mice exhibited a significant delay in the formation of granulation tissue, and in wound closure when compared to their WT HSA$^{+/+}$ littermates. Wounds were histologically analyzed and scored, based on the degree of cellular invasion, granulation tissue formation, vascularity, and re-epithelialization. Additionally, in stitched wounds, the HSA$^{-/-}$ mice failed to maintain their stitches; they did not hold and fell already 24 hours, revealing erythematous wound fields. Re-expression of HSA, delivered by lentivirus, restored the normal healing phenotype within 24 hours post-injury (Example 3 of the Examples section which follows, Table 3, and FIGS. 6A-C and 7A-G), and even improved the healing in WT C57Bl/6 and in BalbC mice, regardless of the mice strain (Example 4, Table 4, FIG. 8A-D and FIG. 9A-E). These results show that CD24 plays an important role in the process of wound healing. Thus, delayed wound-healing is shown in the absence of HSA/CD24, and on the other hand, increased expression of CD24, even in the normal state, may be used to enhance wound repair. The effect of CD24 on wound healing was evaluated confirmed by immunohistochemistry (IHC) and collagen staining, and most importantly by re-expression of the HSA gene. On the other hand, as described in Example 8 and FIG. 11A-D, downregulation of CD24 using anti-HSA antibody ("M1/69") resulted in slower and non-homogenous healing in HSA-expressing mice. These results suggest using CD24 for improving and accelerating the wound healing process.

In addition, the present inventors describe the preparation of pharmaceutical compositions for topical application comprising CD24 for wound healing, which comprise ionic or a non-ionic surfactant (Example 5 of the Examples section which follows); the preparation of full length CD24 protein which can be used for gene therapy by viral infection or for transfection of mammalian cells (Example 6 of the Examples section which follows) to thereby obtain a GPI-anchored CD24 protein with or without a glycosylation modification, such as the polypeptides described in FIG. 10A (SEQ ID NO: 1) and FIG. 12B (SEQ ID NO:29); and the preparation of a construct encoding a soluble CD24 polypeptide (Example 7, FIG. 10B, SEQ ID NO:7), which when produced within a cell (e.g., a bacterial or mammalian cell) includes only the core protein and the HIS tag as depicted in SEQ ID NO: 30, and illustrated in FIG. 12C. In addition, Example 9 of the Examples section which follows and FIGS. 13A-E describe the generation of several DNA constructs of HSA (SEQ ID NOs: 58-67) and of CD24 (SEQ ID NOs: 68-77) which can be used for improving wound healing. Furthermore, as described in Examples 10 and 11 of the Examples section which follows, the present inventors have devised an in vitro bio assay for determining the efficacy of the CD24 polypeptides on wound healing using cell lines which express relatively low levels of endogenous CD24 (e.g., the colon cancer mouse cell line mc38 and the mouse colon carcinoma cell line CT26; FIG. 15A-D) which are cultured on a plate as cell monolayer. Thus, for mimicking wounds, the cell monolayers are scraped to create a denuded zone (gap) of constant width, and the migration of the cells towards closing the gap is evaluated over time. Indeed, as shown in FIGS. 16A-I and 17A-L and described in Example 11 of the Examples section which follows, the cell migration into the cell-free area (the gap) in plates which included the HSA protein (produced from construct number 5) was faster than in the control plates devoid of HSA (CD24). In addition, as described in Example 12 of the Examples section which follows, the present inventors have confirmed the in vitro results in an in vivo assay, when the CD24 which was produced from construct number 5 improved wound healing by a faster, and in a more aesthetic manner, closure of the wounds as compared to in the absence of CD24 (FIGS. 18A-L and 19A-H).

According to an aspect of some embodiments of the invention there is provided a method of improving wound healing in a subject in need thereof, the method comprising administering to the subject a therapeutically effective amount of CD24, thereby improving wound healing in the subject.

According to an aspect of some embodiments of the invention there is provided a method of improving wound healing in a subject in need thereof, the method comprising topically administering to a wounded area of the subject a therapeutically effective amount of CD24, thereby improving the wound healing in the subject.

The term "wound" as used herein refers cutaneous break(s) and/or mucosal membrane break(s).

The wound according to some embodiments of the invention includes open wounds that have been sutured or otherwise mechanically closed but have not healed or repaired the cutaneous or mucosal breaks.

According to some embodiments of the invention, the wound is a cutaneous break(s).

The term "cutaneous break" as used herein refers to any lesion or open wound that can expose underlying epidermal, dermal, muscular and/or adipoidal tissue to the air. Examples include, but are not limited to, a puncture wound, an incision, a laceration, a penetrating wound, a perforating wound, a tunnel wound, burn, and the like.

The cutaneous break according to some embodiments of the invention, with the proviso that the cutaneous break does not include a break of hair.

According to some embodiments of the invention, the wound is a mucosal membrane break(s).

Mucosal membrane breaks include, but are not limited to, ulcer(s); break(s) in nasal mucous membrane; break(s) in the eye mucosal membrane (e.g., breaks in the surface layers of the eye including the conjunctiva and cornea); break(s) in the ear mucosal membrane; break(s) in oropharynx (e.g., mouth, larynx and pharynx) mucosal membrane such as those caused by aphta, tooth extraction, and the like.

Examples of aphta which involves mucosal break include, but are not limited to, an oral ulcer (an open sore in the mouth), and aphthous ulcer (or "canker"; an open sore in the mucous membrane of the mouth).

Examples of ulcers which involve mucosal break include ulcers in the digestive system (including e.g., in the esophagus, stomach, small intestine, colon, rectum and anus), and ulcers in the genitalia (e.g., genital ulcers caused by a sexually transmitted disease such as genital herpes, syphilis, chancroid, or *Chlamydia trachomatis*; genital ulcers in patients with Behcet's syndrome, lupus, and some forms of rheumatoid arthritis; genital ulcers associated with genital tuberculosis).

The term "wound healing" refers to a process involving tissue growth that partially or totally closes a wound, e.g., repairs a breach in the dermis or epidermis and partially or totally restores the barrier properties of the skin, or repairs of the surface layers of a mucosal membrane.

For example, wound healing of an eye mucosa refers to the repair of the surface layers of the eye including the conjunctiva and cornea.

The process of wound healing consists of three phases during which the injured tissue is repaired, regenerated, and new tissue is reorganized into a scar. These three phases are classified as: a) an inflammation phase which begins from day 0 e.g., to about 3 days, b) a cellular proliferation phase from about day 3 to about day 12, and c) a remodeling phase from about say 3 to about 6 months. Sometimes wound repair is hampered resulting in the formation of keloid.

In the inflammation phase, inflammatory cells, mostly neutrophils, enter the site of the wound followed by lymphocytes, monocytes, and later macrophages. The neutrophils that are stimulated begin to release proteases and reactive oxygen species into the surrounding medium with potential adverse effects on both the adjacent tissues and the invading microorganisms. The oxygen species known to be released by the neutrophils are superoxide ($O_2^-$) through the action of a plasma membrane-bound NADPH oxidase, hydrogen peroxide ($H_2O_2$) formed by action of dismutation of $O_2^-$ and HOCl produced by the action of myeloperoxidase with $H_2O_2$.

The proliferative phase consists of laying down new granulation tissue, and the formation of new blood vessels in the injured area. The fibroblasts, endothelial cells, and epithelial cells migrate in the wound site. These fibroblasts produce the collagen that is necessary for wound repair. Ascorbic acid is crucial in the formation of collagen.

Several studies have demonstrated that ascorbic acid was capable of overcoming the reduced proliferative capacity of elderly dermal fibroblasts, as well as increasing collagen synthesis in elderly cells by similar degrees as in newborn cells even though the basal levels of collagen synthesis are age dependent.

In re-epithelialization, epithelial cells migrate from the free edges of the tissue across the wound. This event is succeeded by the proliferation of epithelial cells at the periphery of the wound. Research has also shown that re-epithelialization is enhanced by the presence of occlusive wound dressings which maintain a moisture barrier.

The final phase of wound healing, which is remodeling, is effected by both the replacement of granulation tissue with collagen and elastin fibers and the devascularization of the granulation tissue.

It should be noted that improving wound healing can include decreasing or shortening the time period required for the wound to heal, as well as improving quality of the healing process of a wound.

As mentioned, a delayed or impaired wound healing can result in a disorganized healing process, similar to the formation of a keloid.

According to some embodiments of the invention, the wound healing refers to prevention or at least decreasing the formation of a keloid.

According to some embodiments of the invention improving wound healing comprises shortening the time period required for the wound to heal by at least 2%, at least 3%, at least 4%, at least 5%, at least 6%, at least 7%, at least 8%, at least 9%, at least 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, e.g., at least about 100% as compared to the time period required for the same (e.g., identical) wound to heal in the absence of administration of the CD24 to the subject under identical conditions.

According to some embodiments of the invention improving wound healing comprises the quality of the healing process of the wound as compared to the quality of the healing process of the same (e.g., identical) wound in the absence of administration of the CD24 to the subject under identical conditions.

Parameters which can be used to assess the wound healing include, but are not limited to the time required to close the wound, the appearance of the wounded area, and the aesthetic shape of the closed wound.

According to some embodiments of the invention, wound healing is scored by histological evaluation of tissue sections obtained from a tissue biopsy of the wound.

For example, a scoring of "1-3" refers to none to minimal cell accumulation. No granulation tissue or epithelial travel; a scoring of "4-6" refers to thin, immature granulation that is dominated by inflammatory cells but has few fibroblasts, capillaries or collagen deposition. Minimal epithelial migration; a scoring of "7-9" refers to moderately thick granulation tissue, can range from being dominated by inflammatory cells to more fibroblasts and collagen deposition. Extensive neovascularization. Epithelium can range from minimal to moderate migration; a scoring of "10-12" refers to thick, vascular granulation tissue dominated by fibroblasts and extensive collagen deposition. Epithelium partially to completely covering the wound.

It should be noted that a higher score in the histological evaluation indicates a better and/or improved wound healing.

According to some embodiments of the invention, wound healing is scored by evaluation of the collagen. Collagen scoring is described in Movin and Bonar Scores Assess the Same Characteristics of Tendon Histology, Clin Orthop Relat Res (2008) 466:1605-1611, which is fully incorporated herein by reference in its entirety.

For example, when the collagen is arranged in tightly cohesive well demarcated bundles with a smooth dense bright homogeneous polarization pattern with normal crimping the collagen scoring is "grade 0"; when there is diminished fiber polarization: separation of individual fibers with maintenance of demarcated bundles the collagen scoring is "grade 1"; when there are bundle changes: separation of fibers with loss of demarcation of bundles giving rise to expansion of the tissue overall and clear loss of normal polarization pattern the collagen scoring is "grade 2"; and when there is marked separation of fibers with complete loss of architecture the collagen scoring is "grade 3".

It should be noted that a higher collagen score (higher grade number) indicates a worse wound healing.

As used herein the phrase "therapeutically effective amount of CD24" refers to the amount of CD24 which is sufficient to improve wound healing.

As used herein the term "CD24" refers to a sialoglycoprotein that is expressed on mature granulocytes and B cells and modulates growth and differentiation signals to these cells. The precursor protein is cleaved to a shorter mature peptide which is anchored via a glycosyl phosphatidylinositol (GPI) link to the cell surface.

CD24 (also known as CD24A) has been cloned from human, rat and mouse sources. Thus, coding sequences information for CD24 is available from several databases including the GenBank database available through ncbi (dot) nlm (dot) nih (dot) gov/. Several variants of human CD24 are known in the art. Variants 1, 2, and 3 encode isoform "a" and variant (4) encodes isoform "b", which has a distinct N-terminus and is longer than isoform "a". CD24 variant (1) [GenBank Accession No. NP_037362.1 (SEQ ID NO:21), encoded by GenBank Accession No. NM_013230.3 (SEQ ID NO:25)], which represents the longest transcript; CD24 variant (2) [GenBank Accession No. NP_001278666.1 (SEQ ID NO:18), encoded by GenBank Accession No. NM_001291737.1 (SEQ ID NO:22)] which differs in the 5' UTR compared to variant (1); CD24 variant (3) [GenBank Accession No. NP_001278667.1 (SEQ ID NO:19) encoded by GenBank Accession No. NM_001291738.1 (SEQ ID NO:23)], which differs in the 5' UTR (untranslated region) compared to variant (1); and CD24 variant (4) [GenBank Accession No. NP_001278668.1 (SEQ ID NO:20) encoded by GenBank Accession No. NM_001291739.1 (SEQ ID NO:24)] which differs in the 5' UTR, lacks a portion of the 5' coding region, and initiates translation at an alternate start codon, compared to variant 1. The encoded isoform "b" has a distinct N-terminus and is longer than isoform "a".

To express CD24 [e.g., GenBank Accession Nos. NP_001278666.1 (SEQ ID NO:18), NP_001278667.1 (SEQ ID NO:19), NP_001278668.1 (SEQ ID NO:20), NP_037362.1 (SEQ ID NO:21) or any of the CD24 sequences described herein, e.g., SEQ ID NOs: 28, 29, 30, 69, 71, 73, 75 and/or 77] in a cell, a polynucleotide sequence encoding a CD24 [e.g., GenBank Accession numbers NM_001291737.1 (SEQ ID NO:22), NM_001291738.1 (SEQ ID NO:23), NM_001291739.1 (SEQ ID NO:24), NM_013230.3 (SEQ ID NO:25), SEQ ID NOs: 1, 3, 7, 11, 68, 70, 72, 74 and/or 76] is preferably ligated into a nucleic acid construct suitable for cell expression. Such a nucleic acid construct includes a promoter sequence for directing transcription of the polynucleotide sequence in the cell in a constitutive or inducible manner.

For example, for gene therapy in vivo, the CD24 coding sequence is preferably ligated into a nucleic acid construct suitable for mammalian cell expression.

According to some embodiments of the invention, the CD24 polynucleotide sequence is operably linked to the promoter sequence.

A coding nucleic acid sequence is "operably linked" to a regulatory sequence (e.g., promoter) if the regulatory sequence is capable of exerting a regulatory effect on the coding sequence linked thereto.

According to some embodiments of the invention, the promoter is heterologous to the CD24 polynucleotide and/or to the host cell.

As used herein the phrase "heterologous promoter" refers to a promoter from a different species or from the same species but from a different gene locus as of the CD24 polynucleotide sequence.

According to some embodiments of the invention, the CD24 which is administered to the subject includes at least the active fragment of CD24, e.g., at least the amino acid sequence SETTTGTSSNSSQSTSNSGLAPNPTNATTKA as set forth by SEQ ID NO:28.

It will be appreciated that the nucleic acid construct of some embodiments of the invention can also utilize CD24 homologues which exhibit the desired activity (i.e., improving wound healing). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the sequences depicted by SEQ ID NOs: 1, 3, 7, 11, 22, 23, 24, 25, 68, 70, 72, 74 and/or 76, or to the polynucleotide encoding the CD24 polypeptide depicted by SEQ ID NOs: 28, 29, 30, 18, 19, 20, 21, 69, 71, 73, 75 and/or 77, as determined using the BestFit software of the Wisconsin sequence analysis package, utilizing the Smith and Waterman algorithm, where gap weight equals 50, length weight equals 3, average match equals 10 and average mismatch equals −9.

According to some embodiments of the invention, the identity is a global identity, i.e., an identity over the entire amino acid or nucleic acid sequences of the invention and not over portions thereof.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example the tetracycline-inducible promoter (Zabala M, et al., Cancer Res. 2004, 64(8): 2799-804).

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of CD24 mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding a CD24 can be arranged in a "head-to-tail" configuration, may be present as an inverted complement, or in a complementary configuration, as an anti-parallel strand.

While such variety of configuration is more likely to occur with non-coding elements of the expression vector, alternative configurations of the coding sequence within the expression vector are also envisioned.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of CD24 since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Non-limiting examples of viral vectors which can be used to produce CD24 in human cells include a VSV-G vector [an Empty Backbone vector with an envelope protein for producing lentiviral and MuLV retroviral particles; e.g., pCMV-VSV-G from the addgene (the nonprofit plasmid repository), plasmid catalogue number 8454], a gag and pol-containing vector such as the pCMV-Gag-Pol Vector [Catalog number: RV-111 available from CELL BIOLABS, INC San Diego, Calif., USA] and a CD24 containing vector such as pcDNA4 containing the full length CD24 coding sequence (e.g., SEQ ID NO:1) as described in the Example 6 of the Examples section which follows.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the CD24 protein of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the CD24 protein and the heterologous protein, the CD24 protein can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of E. coli expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art and are further described hereinbelow can also be used by some embodiments of the invention.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Recovery of the recombinant polypeptide is effected following an appropriate time in culture. The phrase "recovering the recombinant polypeptide" refers to collecting the whole fermentation medium containing the polypeptide and need not imply additional steps of separation or purification. Not withstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

According to some embodiments of the invention the CD24 is injected to the subject.

Modes of injecting into a subject are well known in the art and include, for example, transmucosal, especially transnasal, intestinal or parenteral delivery, including intramuscular, subcutaneous, intradermal injection and intramedullary injections as well as intrathecal, direct intraventricular, intracardiac, e.g., into the right or left ventricular cavity, into the common coronary artery, intravenous, intraperitoneal, intranasal, or intraocular injections.

According to some embodiments of the invention the CD24 is applied directly on a wounded area of the subject.

According to some embodiments of the invention the CD24 is applied by dropping a pharmaceutical composition comprising the CD24 on the wounded area of the subject.

According to some embodiments of the invention the CD24 is comprised in a medical dressing.

Medical dressings suitable for use in the methods of some embodiments of the invention for contacting a wound with the CD24 can be any material that is biologically acceptable and suitable for placing over any wound such as a burn, or a surface lesion of the skin or the oral mucosa or teeth of the mouth. In exemplary embodiments, the medical dressing may be a woven or non-woven fabric of synthetic or non-synthetic fibers, or any combination thereof. The medical dressing may also comprise a support, such as a polymer foam, a natural or man-made sponge, a gel or a membrane that may absorb or have disposed thereon the CD24 of a therapeutic composition comprising same. A gel suitable for use as a support for the CD24 composition of some embodiments of the invention is KY™ [sodium carboxymethylcellulose 7H 4F (Hercules, Inc., Wilmington, Del.)].

A film, a natural or synthetic polymer, or a rigid or malleable material that is known to one of ordinary skill in the art as being acceptable for insertion in the mouth of a human or animal can place the CD24 according to some embodiments of the invention in contact with a tooth or a lesion of the oral mucosa.

In some embodiments of the invention the support of the medical dressing is a gauze. The gauze may be absorbent and can be wetted with the CD24 before applying the gauze to an infected wound or other site.

According to some embodiments of the invention, the CD24 is soaked or impregnated in the medical dressing.

For example, when using a medical dressing with a gauze, the gauze may be impregnated with the therapeutic composition and then dried. This allows the impregnated dressing to be stored for later use, or to avoid excessively dampening an injured area.

According to some embodiments of the invention, the CD24 is absorbed on the surface of the medical dressing.

For example, CD24 or a therapeutic composition comprising same can be absorbed on the surface of the support material of the medical dressing. The CD24 or a therapeutic composition comprising same may be applied to the surface by wetting the surface with a solution of the CD24 or the therapeutic composition comprising same and drying the support to deposit the CD24 and/or the therapeutic composition comprising same thereon.

It is noted that a concentration of CD24 or the composition comprising same that is effective for promoting wound healing and/or repair may be attained when the dressing is wetted by the patient's body.

According to some embodiments of the invention, administering the CD24 is by in vivo gene therapy.

Methods of administering a polypeptide by gene therapy are well known in the art and described for Examples 3, 4 and 9 of the Examples section which follows. Such methods can utilize viral vectors encoding CD24 are is described hereinabove.

The CD24 of some embodiments of the invention can be administered to an organism per se, or in a pharmaceutical composition where it is mixed with suitable carriers or excipients.

According to some embodiments of the invention, the CD24 is comprised in a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

According to some embodiments of the invention the term "pharmaceutical composition" also encompasses a cosmetic composition.

Herein the term "active ingredient" refers to the CD24 accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous, intradermal injection and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the blood brain barrier (BBB)) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

The pharmaceutical composition can be applied directly to the skin. Alternatively, it can be delivered via normal skin application by various transdermal drug delivery systems which are known in the art, such as transdermal patches that release the composition into the skin in a time released manner. Other drug delivery systems known in the arts include pressurized aerosol bottle, iontophoresis or sonophoresis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically mediated transport of therapeutic agents across the skin. Alternatively, or in addition, liposomes or micelles may also be employed as a delivery vehicle.

The pharmaceutical composition can be administered by spreading the pharmaceutical composition on a place to be treated of the object. Spreading can be achieved by hand or a tool (preferably, a sterile tool). It is favorable to make the pharmaceutical composition of the present invention in a formulation of a solution, a suspension, an emulsion, an ointment because those types of formulations would be convenient for spreading.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (CD24) effective to prevent, alleviate or ameliorate symptoms of a disorder (e.g., wound healing) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide tissue levels (e.g., within the wound or on the surface of the wound) of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

According to some embodiments of the invention, the CD24 is formulated with a surfactant in the pharmaceutical composition.

The term "surfactant" as used herein refers to a compound that lowers surface tension of an aqueous solution. Surfactants may act as detergents, wetting agents, emulsifiers, foaming agents, and/or dispersants.

Surfactants are usually organic compounds that are amphiphilic, meaning they contain both hydrophobic groups ("tails") and hydrophilic groups ("heads"). Therefore, a surfactant contains both a water-insoluble (or oil-soluble) component and a water-soluble component. Surfactants will diffuse in water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase.

The "tail" of most surfactants is fairly similar, consisting of a hydrocarbon chain, which can be branched, linear, or aromatic. Fluorosurfactants have fluorocarbon chains. Siloxane surfactants have siloxane chains.

A non-ionic surfactant has no charged groups in its head. The head of an ionic surfactant carries a net positive, or negative charge. If the charge is negative, the surfactant is more specifically called anionic; if the charge is positive, it is called cationic. If a surfactant contains a head with two oppositely charged groups, it is termed zwitterionic.

Many important surfactants include a polyether chain terminating in a highly polar anionic group. The polyether groups often comprise ethoxylated (polyethylene oxide-like) sequences inserted to increase the hydrophilic character of a surfactant. Polypropylene oxides conversely, may be inserted to increase the lipophilic character of a surfactant.

Surfactant molecules have either one tail or two; those with two tails are referred to as being double-chained.

Commonly encountered surfactants of each type include: Anionic surfactants, cationic surfactants, zwitterionic surfactants and nonionic surfactants.

According to some embodiments of the invention the surfactant is an ionic surfactant.

Examples of anionic surfactants include, but are not limited to, sulfate, sulfonate, phosphate esters and carboxylates. Prominent alkyl sulfates include ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), and sodium myreth sulfate. Others anionic surfactants include Docusate (dioctyl sodium sulfosuccinate), Perfluorooctanesulfonate (PFOS), Perfluorobutanesulfonate, Alkyl-aryl ether phosphates, Alkyl ether phosphates and Carboxylates. The most common surfactants which comprise the alkyl carboxylates (soaps), include, sodium stearate, sodium lauroyl sarcosinate and carboxylate-based fluorosurfactants such as perfluorononanoate, perfluorooctanoate (PFOA or PFO).

Examples of cationic surfactants include, but are not limited to, Octenidine dihydrochloride, Cetrimonium bromide (CTAB), Cetylpyridinium chloride (CPC), Benzalkonium chloride (BAC), Benzethonium chloride (BZT), Dimethyldioctadecylammonium chloride, and Dioctadecyldimethylammonium bromide (DODAB).

Zwitterionic (amphoteric) surfactants have both cationic and anionic centers attached to the same molecule. The cationic part is based on primary, secondary, or tertiary amines or quaternary ammonium cations. The anionic part can be more variable and include sulfonates, as in the sultaines CHAPS (3-[(3-Cholamidopropyl)dimethylammonio]-1-propanesulfonate) and cocamidopropyl hydroxysultaine. Betaines such as cocamidopropyl betaine have a carboxylate with the ammonium. The most common biological zwitterionic surfactants have a phosphate anion with an amine or ammonium, such as the phospholipids phosphatidylserine, phosphatidylethanolamine, phosphatidylcholine, and sphingomyelins.

According to some embodiments of the invention the surfactant is a non-ionic surfactant.

Many long chain alcohols exhibit some surfactant properties. Prominent among these are the fatty alcohols, cetyl alcohol, stearyl alcohol, and cetostearyl alcohol (consisting predominantly of cetyl and stearyl alcohols), and oleyl alcohol.

Examples of nonionic surfactants include, but are not limited to Polyoxyethylene glycol alkyl ethers (Brij): CH3-(CH2)10-16-(O—C2H4)1-25-OH; Octaethylene glycol monododecyl ether; Pentaethylene glycol monododecyl ether; Polyoxypropylene glycol alkyl ethers: CH3-(CH2)10-16-(O—C3H6)1-25-OH; Glucoside alkyl ethers: CH3-(CH2)10-16-(O-Glucoside)1-3-OH; Decyl glucoside; Lauryl glucoside; Octyl glucoside; Polyoxyethylene glycol octylphenol ethers: C8H17-(C6H4)-(O—C2H4)1-25-OH; Triton X-100; Polyoxyethylene glycol alkylphenol ethers: C9H19-(C6H4)-(O—C2H4)1-25-OH; Nonoxynol-9; Glycerol alkyl esters; Glyceryl laurate; Polyoxyethylene glycol sorbitan alkyl esters: Polysorbate; Sorbitan alkyl esters: Spans; Cocamide MEA, cocamide DEA; Dodecyldimethylamine oxide; Block copolymers of polyethylene glycol and polypropylene glycol: Poloxamers; Polyethoxylated tallow amine (POEA).

For topical administration of the active ingredient, the pharmaceutical composition can include an epidermal penetrant.

Epidermal Penetrants

In order to enhance the percutaneous absorption of the active ingredients (e.g., CD24), one or more of a number of agents can be added to the pharmaceutical composition including, but not limited to, dimethylsulfoxide, dimethylacetamide, dimethylformamide, surfactants, azone, alcohol, acetone, propylene glycol and polyethylene glycol.

In a preferable embodiment of the present invention, the pharmaceutical acceptable carrier is, but not limited to, water, alcohol, glycerol, chitosan, alginate, chondroitin, Vitamin E, Vitamin A, mineral oil, dimethyl sulfoxide (DMSO), or a combination thereof.

Carriers

In addition to the pharmaceutically effective amount of an agent disclosed herein, the pharmaceutical composition of some embodiments of the invention can include a dermatologically acceptable carrier.

The phrase "dermatologically acceptable carrier", refers to a carrier which is suitable for topical application onto the skin, i.e., keratinous tissue, has good aesthetic properties, is compatible with the active agents of the present invention and any other components, and is safe and non-toxic for use in mammals. An effective amount of carrier is selected from a range of about 50% to about 99.99%, preferably from about 80% to about 99.9%, more preferably from about 90% to about 98%, and most preferably from about 90% to about 95%, by weight, of the composition.

Emulsions

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

Useful topical compositions of the present invention comprise from about 30% to about 90%, more preferably from about 50% to about 85%, and most preferably from about 70% to about 80% of a dispersed aqueous phase. The term "dispersed phase" is well-known to one skilled in the art it implies that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner, D. J. et al., issued Dec. 17, 1991, and U.S. Pat. No. 5,073,372, to Turner, D. J. et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing rheological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See, McCutcheon's. Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al. issued to Dec. 20, 1983; and U.S. Pat. No. 3,755,560. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued to Sep. 29, 1992; U.S. Pat. No. 5,151,210 to Steuri et al., issued to Sep. 29, 1992; U.S. Pat. Nos. 5,120,532; 4,387,090; 3,155,591; 3,929,678; 3,959,461; McCutcheon's, Detergents & Emulsifiers (North American edition 1979) M.C. Publishing Co.; and Schwartz, et al., Surface Active Agents, Their chemistry and Technology, New York: Interscience Publishers, 1949.

Alternatively, other useful cationic emulsifiers include amino-amides. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

The preferred oil-in-water emulsion comprises from about 25% to about 98%, preferably from about 65% to about 95%, more preferably from about 70% to about 90% water by weight of the topical carrier.

Topical Compositions

The pharmaceutical composition can be formulated in any of a variety of forms for skin application including solutions, lotions, sprays, creams, ointments, salves, gels, etc., as described below.

Preferably, the pharmaceutical composition is formulated viscous enough to remain on the treated skin area, does not readily evaporate, and/or is not easily removed by rinsing with water, but rather is removable with the aid of soaps, cleansers and/or shampoos.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

Carriers

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, Cosmetics, Science and Technology, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

The topically applied pharmaceutical composition of some embodiments of the invention may also include additional components which are added, for example, in order to enrich the pharmaceutical compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention.

Examples of these ingredient classes include: abrasives, absorbents, aesthetic components such as fragrances, pigents, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof. According to an aspect of some embodiments of the invention, there is provided a pharmaceutical composition suitable for topical administration, comprising CD24 being in a formulation with a surfactant and a pharmaceutically acceptable carrier.

According to some embodiments of the invention, the surfactant is an ionic surfactant.

According to some embodiments of the invention, the surfactant is a non-ionic surfactant.

According to some embodiments of the invention, the CD24 is comprised in a lentiviral construct.

According to some embodiments of the invention, a concentration of the CD24 in the pharmaceutical composition is between 1% to 10% (volume/volume) of a purified CD24 solution. For example, the concentration of the CD24 in the pharmaceutical composition can be between about 2% to about 10%, e.g., between about 3% to about 9%, e.g., between about 4% to about 9%, e.g., between about 5% to about 8%, e.g., between about 6% to about 8%, e.g., between about 7% to about 8% of a purified CD24 solution.

According to some embodiments of the invention, the CD24 is glycosylated.

According to some embodiments of the invention, the CD24 comprises a native glycosylation pattern.

For example, a native glycosylation pattern can be O-linked glycans carrying alpha2,3-linked sialic acid (as 3-linked sialic acid, disialyl motifs, Le(X), sialyl-Le(X) or HNK-1 units) and N-linked glycans highly fucosylated.

According to some embodiments of the invention, the CD24 is non-glycosylated.

According to some embodiments of the invention, the CD24 is soluble.

According to some embodiments of the invention, the CD24 is non-soluble.

As used herein the term "non-soluble" refers to being anchored or linked to a membranous particle, such a lipid moiety.

According to some embodiments of the invention, the CD24 is conjugated to a lipid moiety.

According to some embodiments of the invention, the pharmaceutical composition is suitable for topical application.

According to some embodiments of the invention, the pharmaceutical composition is comprised in an emulsion carrier, a cream, an ointment, an aqueous solution, a lotion or an aerosol.

Analysis and Discussion

The present study shows that HSA in mice plays an important role in wound healing. Restoration of the protein restores impaired wound healing back to normal. Moreover, forced expression of HSA enhances the healing process.

CD24 expression has long been correlated with pathologies associated with tumor cell migration and invasion (19-21). The exact function and mechanism of action of CD24 is mostly unknown; however, it is thought to be involved in a variety of processes such as cell proliferation and it also changes the adhesive properties of tumor cells by promoting their adhesion to P-selectin, fibronectin, collagens I and IV, and laminin (20). Tumors have been previously described as wounds that do not heal. Wound healing and cancer have similar properties of cellular behavior. They are both characterized by increased cell proliferation, survival, invasion and migration (e.g. angiogenesis and metastasis), remodeling of extracellular matrix, new blood vessel formation, and modulation of blood coagulation. The molecular programs in normal wound healing and those in tumor progression and metastasis were found to be similar (22, 23), (24). Data from our laboratory suggest that overexpression of CD24 is associated with increased cell migration in wound healing assays in vitro (Naumov et al., 2014). Taking all of this together with the data presented here, and without being bound by any theory, the present inventors suggest that increased expression of CD24 promotes growth pathways and thus accelerates and improves the healing of wounded tissue. HSA-deficient mice have delayed healing. When the wounds were stitched, the stitches did not hold, suggesting that CD24 is required. In most cases, the healing process was not only delayed but it failed to progress through the normal stages of healing, and resulted in an inflamed scar. Most importantly, re-expression of HSA in HSA-deficient mice, by lentiviruses, restores the wound closure rate in WT mice.

Interestingly, preliminary data emerging from mouse models of bone (tibia fracture model) fracture and tooth extraction strengthen the importance of CD24 in fracture and tooth extraction healing (Arber et al., unpublished data).

Without being bound by any theory it is hypothesized that CD24 plays a key role in cell proliferation, migration and adhesion of healthy cells to the damaged area to restore normal tissue. Increased expression of the CD24 protein may represent a novel clinical intervention strategy to accelerate the healing of debilitating acute or chronic wounds in patients.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 22 is expressed in a DNA sequence format (e.g., reciting T for thymine), but it can refer to either a DNA sequence that corresponds to a CD24 variant (2) nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Animal housing and procedures—Heat stable antigens (HSA) knockout (KO) mice on a C57BL/6J background were kindly provided by Prof. Peter Altevogt (DKFZ Heidelberg, Germany). Wild-type (WT) HSA$^{+/+}$ mice were purchased from Harlan Laboratories (Rehovot, Israel). All mice were fed with a standard pellet diet and had access to tap water ad libitum. The animals were maintained at a constant temperature (22±2° C.) on a 12 hour light/dark cycle and all procedures were approved by the Institutional Committee for Animal Welfare at Tel-Aviv Sourasky Medical Center. Before the procedures, mice were anesthetized by intraperitoneal (i.p.) injection of ketamine [50 mg/kg (milligrams per kilograms)] and xylazine (5 mg/kg). The dorsal surface of the animal was cleaned, shaved, and sterilized with a betadine solution. Longitudinal incisions, 1.5-4 cm (centimeter), were made on the back of the mice. The excised wounds were left open, stitched, or dressed with gauze after virus administration. In HSA/mCherry expression experiments, the virus-containing medium was applied once post-wounding. Wound healing was examined by macroscopic observations and histological analysis every day after wound excision.

Virus production—Three HIV-based viral vectors (kindly provided by Prof. Eran Bacharach, Tel Aviv University, Israel) were used in each experiment: (i) pVSV-G (5 µg) (for generation of the virus envelope), (ii) pCMV.ΔR8.2 (15 µg) (for generation of the Gag and Pol proteins of HIV) and (iii) pHR'CMV-HSA (20 µg) (for generation of the full length HSA sequence set forth by SEQ ID NO:57, encoded by the nucleic acid sequence set forth by SEQ ID NO:56); or (i) pVSV-G (5 µg), (ii) pCMV.ΔR8.2 (15 µg) and (iii) the pHR'CMV-mCherry (for generation of the mCherry sequence set forth by SEQ ID NO: 47, encoded by the nucleic acid sequence set forth by SEQ ID NO:46, as a negative control) (20 µg). The three viral vectors were co-transfected to HEK293T helper cells using the standard calcium phosphate transfection method. Forty-eight hours after transfection, virions-containing supernatants were collected, the pH was adjusted with Hepes, filtered and stored at −80° C.

Infection—Before the infection, polybrene was added to the virions-containing supernatant to a final concentration of 8 µg/ml. The supernatant was added to NIH-3T3 cells, that were seeded in 6-cm plates the day before (5×10$^5$ cells), for 2 hours. Then, 3 ml of fresh medium was added to the plate and after two days the infected cells were analyzed for the expression of the relevant gene.

In vivo, under anesthesia, 300 µl of viruses-containing medium were injected into the cells on the wound border or dropped directly into the wounds area of the mice. Wound closure and mice's well-being were monitored every day.

Imaging of mCherry expression in mice—For all imaging, mice were anesthetized using a ketamine-xylazine mixture. For imaging of mCherry expression, mCherry-encoded viruses (300 µl of viruses-containing medium) were injected into the cells on the wound border or dropped directly into the wounds area of WT mice immediately after injury. The mCherry expression was monitored 96 hours later using the Maestro in vivo fluorescence imaging of whole small animals' device.

Histology—Wound beds surrounded by a margin of non-wounded skin were collected at days 0, 3 and 14 days post-wounding. Samples were fixed with 4% paraformaldehyde overnight at room temperature, embedded in paraffin blocks, and sectioned. After deparaffinization and rehydration, the sections were washed and stained with Hematoxylin and Eosin (H&E) or NovaUltra™ Picro-Sirius Red stain for collagen staining. Tissue sections were then washed, mounted, and visualized on an Olympus AH light microscope at 400× magnification.

Protein extraction and immunoblotting—For protein extraction, cells were washed with phosphate buffered saline (PBS), scraped and lysed in 1% Triton buffer (100 mM NaCl, 5 mM EDTA, 1% triton, 50 mM Tris-HCl pH 7.5, 50 mM NaF, and a protease inhibitor cocktail (Roche), added just before use). Following 30 minutes of incubation on ice, lysates were cleared by centrifugation at 14,000 rpm for 10 minutes at 4° C. For immunoblotting, protein samples were electrophoresed alongside a molecular weight marker on 10% SDS-Polyacrylamide gel electrophoresis (PAGE) and Western blot analysis was performed as described below.

Western Blot analysis—Proteins resolved by SDS-PAGE were electro-transferred onto the nitrocellulose membrane. The membrane was blocked for at least 1 hour with PBST (PBS buffer containing 0.05% Tween 20) containing 5% skim milk at room temperature (RT) with slow agitation. Proteins were detected using a specific primary antibody (M1.69, generous gift from Prof. Peter Altevogt; DKFZ Heidelberg, Germany) followed by horseradish peroxidase (HRP)-conjugated secondary antibody and enhanced chemiluminescence (ECL) detection using the EZ-ECL reagent as described by the vendor (Biological Industries, Beith HaEmek).

Flow cytometry analysis—Cellular CD24 binding by rat M1.69 was evaluated by flow cytometry (FACS). Approximately 1×10$^6$ cells were used in each experiment. After trypsinization, the cells were washed in fluorescence-activated cell sorting (FACS) buffer (10% FBS, 0.01% sodium azide in ice-cold PBS) and fixed with 2% formaldehyde for 15 minutes at RT. After washing with FACS buffer, 100 µl of 15 µg/ml anti-CD24 were added for 30 minutes at RT (room temperature). After washing X3 with FACS buffer, fluorescein isothiocyanate (FITC)—labeled goat anti-rat (1:100) was added for 30 minutes at RT. Detection of bound antibodies was performed on a FACSCalibur (Becton Dickinson, San Jose, Calif.) and results were analyzed with the CELLQuest program (Becton Dickinson).

Example 1

Delayed Wound Healing In HSA KO Mice

Experimental Results

Several independent experiments with 10-mm oblong full-thickness excision wounds, including the striated muscle layer, on the dorsal skin of WT (HSA$^{+/+}$) (n=5) and KO (HSA$^{−/−}$) (n=5) mice demonstrated that the absence of HSA hampered the healing of skin wounds (FIG. 1A-G). Moreover, the KO mice failed to keep the stitches in the stitched wounds. Healing of KO mice wounds remained incomplete. In the HSA KO mice, scabs were thicker and erythematous wound fields were shown. Similar results were seen with longer excision wounds (n=6) (FIG. 2A-E).

Histologic scoring [Discordant effects of a soluble VEGF receptor on wound healing and angiogenesis, Gene Therapy (2004) 11, 302-309. doi:10.1038/sj.gt.3302162] was based on the degree of cellular infiltration, granulation tissue formation, and re-epithelialization (Table 1 below). Wounds of WT mice had higher average histologic scores compared to the KO mice. There was a greater degree of cellular infiltration and capillary ingrowth in the $HSA^{+/+}$ mice (FIG. 3A-C).

Table 1

Histological Scoring of Wild Type and HSA KO Mice

TABLE 1

Provided are the histological scoring of the wild type (WT) and CD24 knockout (KO) mice. The scoring system is as follows: "1-3" = None to minimal cell accumulation. No granulation tissue or epithelial travel; "4-6" = Thin, immature granulation that is dominated by inflammatory cells but has few fibroblasts, capillaries or collagen deposition. Minimal epithelial migration; "7-9" = Moderately thick granulation tissue, can range from being dominated by inflammatory cells to more fibroblasts and collagen deposition. Extensive neovascularization. Epithelium can range from minimal to moderate migration; "10-12" = Thick, vascular granulation tissue dominated by fibroblasts and extensive collagen deposition. Epithelium partially to completely covering the wound.

| WT | | | KO | | |
|---|---|---|---|---|---|
| t = 0 hours | t = 72 hours | t = 14 days | t = 0 hours | t = 72 hours | t = 14 days |
| 12 | 4-6 | 11-12 | 12 | 1-3 | 4-6 |

In addition, the collagen scoring [Movin and Bonar Scores Assess the Same Characteristics of Tendon Histology, Clin Orthop Relat Res (2008) 466:1605-1611] confirmed the IHC staining (Table 2). The fibers were still separated with complete loss of architecture in the $HSA^{-/-}$ mice 72 hours after the wound was established (FIG. 4A-C).

Table 2

Collagen Scoring

TABLE 2

| | Grade 0 | Grade 1 | Grade 2 | Grade 3 |
|---|---|---|---|---|
| Collagen | Collagen arranged in tightly cohesive well demarcated bundles with a smooth dense bright homogeneous polarization pattern with normal crimping | Diminished fiber polarization: separation of individual fibers with maintenance of demarcated bundles | Bundle changes: separation of fibers with loss of demarcation of bundles giving rise to expansion of the tissue overall and clear loss of normal polarization pattern | Marked separation of fibers with complete loss of architecture |
| | WT, KO; t = 0 | | WT = 72 hours | KO = 72 hours |

Example 2

Production Of HSA-Encoding Viruses

Experimental Results

Three viral-based vectors were used to deliver and express the HSA gene in the wounded tissue. First, the expression of the transgene by the helper cells, in vitro, was confirmed by monitoring the mCherry fluorescence marker (FIG. 5A) and Western blot analysis (FIG. 5C). Next, the infectivity of the produced virions was tested in vitro on NIH-3T3 cells. Seventy two hours post-infection of NIH-3T3 cells, the expression of the HSA/mCherry proteins was examined and confirmed by fluorescence microscopy (FIG. 5B), Western blot (FIG. 5C) and FACS analysis (FIG. 5D).

Example 3

Re-Expression of HSA Restored the Healing Phenotype

Experimental Results

Next, the present inventors examined whether the expression of HSA in $HSA^{-/-}$ mice restores the WT healing capabilities. Firstly, the present inventors verified that the viruses infected the cells in vivo. To that end, in vivo imaging of the wounded tissue in the WT mice 96 hours after virus injection/dropping confirmed the expression of mCherry and HSA in the wounded tissue (FIG. 6A-C).

Then the importance of HSA in the healing process was evaluated by an additional experiment that was performed as described in Table 3 below. Briefly, mice from each genotype were randomly divided into groups of three mice. Longitudinal incisions of 1.5 cm were made on their back and the HIV-encoding viruses (encoding mCherry SEQ ID NO: 47 or HSA SEQ ID NO:57) were administrated by injection into the cells on the wound border or by dropping of the viruses into the wounded area. The healing was monitored every day for one week.

Table 3

Design of In Vivo Experiment

TABLE 3

|  | Number of mice | Mice genotype | Length of cut | Treatment |
|---|---|---|---|---|
| Group 1 | 3 | HSA$^{+/+}$ | 1.5 cm | Only wound |
| Group 2 | 3 | HSA$^{+/+}$ | 1.5 cm | HIV-mCherry injection |
| Group 3 | 3 | HSA$^{+/+}$ | 1.5 cm | HIV-mCherry dropping |
| Group 4 | 3 | HSA$^{+/+}$ | 1.5 cm | HIV-HAS injection |
| Group 5 | 3 | HSA$^{+/+}$ | 1.5 cm | HIV-HAS dropping |
| Group 6 | 3 | HSA$^{-/-}$ | 1.5 cm | Only wound |
| Group 7 | 3 | HSA$^{-/-}$ | 1.5 cm | HIV-mCherry injection |
| Group 8 | 3 | HSA$^{-/-}$ | 1.5 cm | HIV-mCherry dropping |
| Group 9 | 3 | HSA$^{-/-}$ | 1.5 cm | HIV-HAS injection |
| Group 10 | 3 | HSA$^{-/-}$ | 1.5 cm | HIV-HAS dropping |

As shown in FIG. 7A-G, re-expression of HSA restores the healing phenotype in the HSA$^{-/-}$ mice while the expression of the control mCherry vector had no effect (FIG. 7A-G). These results conclusively show that CD24 is capable of improving wound healing in subjects which are deficient in CD24 expression.

Example 4

Overexpression of HSA in Wt Mice Improves Wound Healing

Experimental Results

The present inventors have further evaluated the ability of HSA to improve the wound healing process in normal HSA$^{+/+}$ WT mice. For this purpose, the wound size was enlarged and the experiment was performed as described in Table 4. Briefly, HSA$^{+/+}$ mice were randomly divided into groups of four mice each. Longitudinal incisions of 4-cm were made on their back and the mCherry or HSA-encoding viruses were administered twice, 0 and 24 hours post-injury, by injection into the cells in the wound border or by dropping of the viruses into the wounded area and the healing rate was monitored.

Table 4

Design of Experiment

TABLE 4

|  | Wound size | Treatment | Administration |
|---|---|---|---|
| Group 1 | 4 cm | NO | |
| Group 2 | 4 cm | mCherry (T = 0, 24 hours) | dropping |
| Group 3 | 4 cm | mCherry (T = 0, 24 hours) | Injection |
| Group 4 | 4 cm | HSA (T = 0, 24 hours) | dropping |
| Group 5 | 4 cm | HSA (T = 0, 24 hours) | Injection |

As shown in FIG. 8A-D overexpression of HSA resulted in faster and improved healing even in HSA-expressing mice. Already after 24 hours it was shown that there were differences in the healing rate between mice that were administrated with mCherry and HSA. These results conclusively show that CD24 is capable of improving wound healing in normal subjects which express CD24.

The improvement of healing by HSA expression does not depend on the mice strain—In order to examine if the above phenotype depends on the mice strain, the present inventors compared between Balb/C and C57Bl/6J WT mice. Eight mice from each strain were randomly divided to two groups of four mice. One group of each strain was injected with HSA-encoding viruses, immediately after the injury, while the second group with the control vector. According to the observations shown in FIG. 9A-E, the wound healing was improved regardless of the mice strain.

Example 5

Pharmaceutical Compositions Comprising CD24 For Wound Healing

In order to find more applicable routes for clinical use the present inventors prepared pharmaceutical formulations that allow topical administration of HSA. Two different HSA-containing formulations are tested in vivo. The difference between the two formulations is the surfactants. The first contains a substance which is ionic and the second one does not. Both formulations are mixed with the purified protein (~10% of the volume is the HSA protein).

Experimental Design

Construction of HSA-Expressing Plasmid

Initially, a DNA fragment coding for a full-length murine CD24 fragment is amplified by PCR using the plasmid HSA-IRES-GFP (that was constructed by the present inventors) as a template using primers For-5'-ATATA-CATATGGGCAGAGCGATGGTGGCC-3' (SEQ ID NO:26) and Rev-5'-TATATGAATTCTTAGTGATGGT-GATGGTGATGCGGCGGTTGACAGTAGAGATGTA-GAAG-3' (SEQ ID NO:27). The PCR product is digested by NdeI and EcoRI and inserted into the pet22b plasmid. 6×HIS tag is inserted in the 3' in order to facilitate the purification.

Expression and Purification of Engineered Proteins from Bacteria

E. coli BL21 Rosetta (DE3) cells is transformed with the expression plasmid and grown in 1 liter of SB medium supplemented with 0.4 gr/L MgSO4, 0.5% (w/v) glucose, and 100 µg/ml ampicillin, at 37° C., 250 rpm shaking, to OD600 of 2.5. The cells are chilled down to 30° C. and induced with 1 mM isopropyl-beta-D-thiogalactopyranoside (IPTG) for 3 hours at 30° C., 250 rpm. The cells are collected by centrifugation at 4000 rpm, at 4° C. for 15 minutes. For preparation of periplasmic fractions, the cell pellet is gently re-suspended using glass beads in 200 ml of ice-cold 20% sucrose, 30 mM Tris-HCl (pH 7.4), 1 mM EDTA, and left on ice for 15 minutes. Next, cells are centrifuged (15 minutes, 6000 rpm at 4° C.), the supernatant is discarded and the culture is gently resuspended in 200 ml of ice-cold sterile DDW (double distilled water), incubated on ice for 15 minutes and centrifuged at 7000 rpm, 4° C. for 15 minutes. The periplasm extract is adjusted to 20 mM Tris-HCl (pH 8.0), 300 mM NaCl and 3 mM imidazole. The periplasmic fraction is incubated over-night, in continues rotation with 350 µl of Ni-NTA resin that is previously equilibrated with binding buffer (20 mM Tris-HCl pH 8.0, 300 mMNaCl). Ni-NTA resin is then separated from the periplasmic supernatant by 5 minutes centrifugation at 500 rpm, 4° C., loaded on a Poly Prep column (Bio-Rad, USA) and washed with 20 ml of binding buffer supplemented with 3 mM imidazole. Bound His-tagged protein is subsequently eluted with 700 μl PBS containing 500 mM imidazole, and dialyzed twice against 1 liter of PBS and filtered. Purified protein is stored at −80° C. For visualization of the purified protein, 1 μg of protein sample is electrophoresed alongside a molecular weight marker on 12% SDS-PAGE and is further stained with Coomassie Blue solution.

In Vivo Experiments

After mixing the purified HSA protein with the two formulations, the therapeutic potential of the ointment is evaluated.

Animal Housing and Procedures

Heat stable antigens knockout (KO) mice on a C57BL/6J background and Wild-type (WT) HSA$^{+/+}$ mice are fed with a standard pellet diet and are accessed to tap water ad libitum. The animals are maintained at a constant temperature (22±2° C.) on a 12 hours light/dark cycle and all procedures are approved by the Institutional Committee for Animal Welfare at Tel-Aviv Sourasky Medical Center. Before the procedures, mice are anesthetized by intraperitoneal (i.p.) injection of ketamine (50 mg/kg) and xylazine (5 mg/kg). The dorsal surface of the animal is cleaned, shaved, and sterilized with a betadine solution. Longitudinal incisions, 1.5-4 cm, are made on the back of the mice. The excised wounds will be either:

a. left open,
b. stitched,
c. dressed with gauze after CD24 protein administration.

The protein is topically applied every day post-wounding.

Wound healing is examined by macroscopic observations and histological analysis every day after wound excision.

Wound surface area is evaluated based on image j software.

Histology—Wound beds surrounded by a margin of non-wounded skin are collected at days 0, 3 and 14 days post-wounding. Samples are fixed with 4% paraformaldehyde overnight at room temperature, embedded in paraffin blocks, and sectioned. After deparaffinization and rehydration, the sections are washed and stained with Hematoxylin and Eosin (H&E) or NovaUltra™ Picro-Sirius Red stain for collagen staining. Tissue sections are then washed, mounted, and visualized on an Olympus AH light microscope at 400× magnification.

Example 6

Preparation of a GPI-Anchored Human CD24

This Example describes the preparation of a full length human CD24 protein which can be used for either gene therapy by viral infection or for transfection of mammalian cells, to thereby obtain a GPI-anchored CD24 protein with or without a glycosylation modification.

FIG. 10A depicts the sequence which is cloned in pcDNA4/TO for generation of full length human CD24 protein. The sequence of the full length human CD24 is set forth in SEQ ID NO: 1.

The full length CD24 sequence is encoded by a DNA sequence encoding a signal peptide (SEQ ID NO:2), a core protein (SEQ ID NO:3) and a C-terminus sequence (SEQ ID NO:4).

The DNA fragment encoding for a full-length human CD24 fragment was amplified by PCR using primers Kozak-HindIII-CD24-F [5'-CTGGAAGCTTGCCACCATG-GATGGGCAGAGCAATGGTGGC-3' (SEQ ID NO:5)] and XbaI-CD24-R [5'-TCATCTAGAGTATTAAGAGTAGA-GATGCAGAAG-3' (SEQ ID NO:6)]. The PCR product was digested by HindIII and XbaI and inserted into the pcDNA4/TO (pcDNA4 tetracycline operator) plasmid, downstream to two tetracycline operator sequences, TetO2, which was cleaved with the same enzymes. The resulting plasmid was named pcDNA4/TO-CD24.

pcDNA4/TO-CD24 was transfected into 293T-REx™ stable cells expressing the tetracycline repressor from the pcDNA6/TR vector (Invitrogen), using the calcium phosphate transfection method. The full length CD24 protein is isolated from these cells by affinity chromatography.

The resulting full length CD24 protein is depicted in SEQ ID NO: 29 and is illustrated in FIG. 12B.

The C-terminus of the human CD24 protein is cut (by GPI transamidase) and lipid modification occurs on the luminal side of the endoplasmic reticulum (ER) membrane, a GPI moiety is added. The CD24-GPI molecule is expected to reach the cell membrane.

Monitoring of the production of CD24-GPI protein can be done using labeled antibodies which specifically bind CD24, and detection of the binding by ELISA or FACS analyses.

Example 7

Preparation of Soluble Human CD24

This Example describes the preparation of a soluble human CD24 protein which can be used for transfection of either mammalian cells or any other cells (e.g., bacterial cells), to thereby obtain a soluble CD24 protein.

FIG. 10B depicts the sequence which is cloned in pcDNA3 plasmid for generation of soluble human CD24 protein. The DNA encoding the soluble CD24 protein is set forth by SEQ ID NO:7.

The soluble CD24 is encoded by a DNA that is composed of nucleic acid sequence encoding a signal peptide (SEQ ID NOs: 8 and 10) which is interrupted by an intron sequence (SEQ ID NO:9), followed by two restriction enzyme recognition sites (SEQ ID NOs: 15 and 16), a DNA encoding a flexible linker (SEQ ID NO:13) and a protease Tev cleavage cite (SEQ ID NO: 14), followed by a nucleic acid sequence encoding the human soluble CD24 core protein (SEQ ID NO:11), restriction enzyme binding site (SEQ ID NO:17) and a nucleic acid sequence encoding a 6×HIS tag (SEQ ID NO:12).

This sequence was cloned into pcDNA3 plasmid. The plasmid was transfected into 293 cells. The protein is to be secreted to the growth media and is to be purified on Ni$^{2+}$ column via the HIS-tag (encoded by SEQ ID NO:12) that is attached to the soluble CD24 protein. For better efficiency of expression and secretion, the present inventors added an intron sequence (SEQ ID NO:9).

The same sequences, full length human CD24 and only the core protein (soluble human CD24), is cloned into pet22b expression plasmid and transform into E. coli BL21 Rosetta (DE3) cells.

The soluble human CD24 which is produced within the cell (e.g., a bacterial or mammalian cell) will include only the core protein and the HIS tag, since after the translation the signal peptide is to be cut within the cell. The soluble CD24 can be isolated by the Ni$^{2+}$ column which binds to the HIS tag.

The resulting soluble CD24 protein is depicted in SEQ ID NO: 30, and illustrated in FIG. 12C.

The CD24 core protein is depicted in SEQ ID NO: 28 and is illustrated in FIG. 12A.

It should be noted that the non GPI (Soluble) CD24 may bind a co-receptor.

Example 8

Downregulation of CD24 Prevents Wound Healing

In order to confirm the importance of CD24/HSA in the healing process, a complementary experiment was performed. HSA+/+ mice were randomly divided into groups of three mice. Longitudinal incisions of 2 cm were made on their back and the anti-HSA M1/69 mAb (10 mg/kg) was administrated immediately post-injury by injection into incisions. As shown in FIG. 11A-D, the antibody-mediated reduction of HSA expression level resulted in slower and non-homogenous healing in HSA-expressing mice.

Example 9

Generation of Constructs Expressing CD24 (HSA)

Design of Constructs

The present inventors have designed several expression vectors for different CD24/HSA derivatives in bacteria, yeast, and mammalian expression systems.

Construct number 1: The construct is schematically depicted in FIG. 13A [Exemplary sequences are provided in SEQ ID NO: 58 (nucleic acid) and SEQ ID NO: 59 (amino acid)]. This construct was codon optimized for better expression in mammalian system. The gene was synthesized and cloned into an expression vector. This construct is designed to produce a secreted protein that contains only the core protein of HSA (without the signal peptide and the native C-terminus of the antigen).

Construct number 1 comprises the HSA core protein (mouse SEQ ID NO:31) upstream and in-frame with the HIS tag (SEQ ID NO:12). A corresponding construct suitable for use in wound healing in human subjects comprises the CD24 core protein (SEQ ID NO: 28) upstream and in frame with the HIS tag (SEQ ID NO:12). Exemplary sequences for human CD24 are provided in SEQ ID NO: 68 encoding SEQ ID NO: 69.

Construct number 2: The construct is schematically depicted in FIG. 13B [Exemplary sequences are provided in SEQ ID NO: 60 (nucleic acid) and SEQ ID NO: 61 (amino acid)]. This construct was codon optimized for better expression in bacteria, yeast and mammalian. The gene was synthesized according to the codon optimization and cloned into the respective expression vectors. This construct is designed to produce the whole antigen (before the post translation medication processing) with the addition of the TAT signal. TAT is a translocating peptide (cell penetrating peptide) which is derived from the HIV-1 Tat protein. This cell penetrating peptide (CPP) is able to cross the plasma membrane and leads to the internalization of the fused protein. The rationale behind this construct is that when this protein is given to the target cells the protein is internalized into the cells (due to the TAT signal) and is directed to the secreted pathway within the cells. Therefore it is assumed that the recombinant protein is processed in a similar way as the native one, which means that the signal peptide is cleaved and the C-terminus is replaced by a GPI anchor.

Construct number 2 comprises the coding sequence of the TAT peptide (SEQ ID NO: 32, encoded by SEQ ID NO:48), followed by the HSA signal peptide (SEQ ID NO: 33, encoded by SEQ ID NO:51), the HSA core protein (SEQ ID NO: 31, encoded by SEQ ID NO:52), the HSA C-terminus (SEQ ID NO:34, encoded by SEQ ID NO:53) and the HIS tag (SEQ ID NO:12). A corresponding construct suitable for use in wound healing in human subjects comprises the CD24 core protein (SEQ ID NO: 28) instead of the HSA core protein, with the same TAT peptide (SEQ ID NO:32), CD24 signal peptide (SEQ ID NO:40, encoded by SEQ ID NO:2) and a CD24 C-terminus (SEQ ID NO:41, encoded by SEQ ID NO:4). Exemplary sequences for human CD24 are provided in SEQ ID NO: 70 encoding SEQ ID NO: 71.

Construct number 3: The construct is schematically depicted in FIG. 13C [Exemplary sequences are provided in SEQ ID NO: 62 (nucleic acid) and SEQ ID NO: 63 (amino acid)]. This construct was codon optimized for better expression in mammalian system. The gene was synthesized and cloned into an expression vector. This construct is designed to produce the core protein that internalizes into the cells due to the TAT signal.

Construct number 3 comprises the coding sequence of the TAT peptide (SEQ ID NO:32, encoded by SEQ ID NO:48), followed by the HSA core protein (SEQ ID NO:31, encoded by SEQ ID NO:52) and the HIS tag (SEQ ID NO:12). A corresponding construct suitable for use in wound healing in human subjects comprises the CD24 core protein (SEQ ID NO: 28) instead of the HSA core protein with the same TAT (SEQ ID NO:32, encoded by SEQ ID NO:48) and HIS tag (SEQ ID NO:12). Exemplary sequences for human CD24 are provided in SEQ ID NO: 72 encoding SEQ ID NO: 73.

Construct number 4: The construct is schematically depicted in FIG. 13D [Exemplary sequences are provided in SEQ ID NO: 64 (nucleic acid) and SEQ ID NO: 65 (amino acid)]. This construct was codon optimized for better expression in bacteria and mammalian systems. The gene was synthesized and cloned into the respective expression vectors. This construct is designed to produce the whole antigen (before the post translation medication processing) with the addition of the TAT signal and transmembrane domain of the EGFR. The rationale behind this construct is that when this protein is given to the target cells the protein is internalized into the cells and is directed to the secreted pathway within the cells, undergoes post translation modification and is translocated to the membrane.

Construct number 4 comprises the coding sequence of the TAT peptide (SEQ ID NO:32, encoded by SEQ ID NO:48), followed by the HSA signal peptide (SEQ ID NO:33, encoded by SEQ ID NO:51), the HSA core protein (SEQ ID NO:31, encoded by SEQ ID NO:52), a linker peptide (SEQ ID NO: 35, encoded by SEQ ID NO:50), a transmembrane domain (TM; SEQ ID NO:36, encoded by SEQ ID NO:49) and the HIS tag (SEQ ID NO:12). A corresponding construct suitable for use in wound healing in human subjects comprises the CD24 core protein (SEQ ID NO: 28) instead of the HSA core protein, the same TAT (SEQ ID NO:32, encoded by SEQ ID NO:48), linker peptide (SEQ ID NO: 35, encoded by SEQ ID NO:50), and transmembrane domain (TM; SEQ ID NO:36, encoded by SEQ ID NO:49) and the CD24 signal peptide (SEQ ID NO:40, encoded by SEQ ID NO:2). Exemplary sequences for human CD24 are provided in SEQ ID NO: 74 encoding SEQ ID NO: 75.

Construct number 5: The construct is schematically depicted in FIG. 13E [Exemplary sequences are provided in SEQ ID NO: 66 (nucleic acid) and SEQ ID NO: 67 (amino acid)]. This construct was designed, optimized for better expression in mammalian system and synthesized. This construct is designed for expression of HSA in mammalian cells which can be further purified. The Fc sequence was added in order to improve production of the HSA protein, and this Fc sequence can be further removed if needed by enzymatic digestion. This target DNA sequence was designed, optimized for better expression in mammalian system and synthesized. The Fc tag is for higher expression yields and rapid purification.

Construct number 5 comprises the coding sequence of the HSA signal peptide (SEQ ID NO: 33, encoded by SEQ ID NO:51), followed by hIgG1Fc (SEQ ID NO:37, encoded by SEQ ID NO:54), a linker (SEQ ID NO:38, encoded by SEQ ID NO:50), FLAG (SEQ ID NO:39, encoded by SEQ ID NO:55), the HSA core protein (SEQ ID NO:31, encoded by SEQ ID NO:52) and a HIS tag (SEQ ID NO:12). A corresponding construct suitable for use in wound healing in human subjects comprises the CD24 core protein (SEQ ID NO: 28, encoded by SEQ ID NO:3) instead of the HSA core protein and a human CD24 signal peptide (SEQ ID NO:40; encoded by SEQ ID NO: 2) instead of the HSA (of mouse) signal peptide. Exemplary sequences for human CD24 are provided in SEQ ID NO: 76 encoding SEQ ID NO: 77.

Production of HSA Using the Designed Constructs

The complete sequence of construct number 5 was sub□cloned into pTT5 vector (FIG. 13E). Transfection grade plasmid was maxi□prepared for 29306E cell expression. 293□6E cells were grown in serum□free FreeStyle™ 293 Expression Medium (Thermo Fisher Scientific). The cells were maintained in Erlenmeyer Flasks (Corning Inc.) at 37° C. with 5% $CO_2$ on an orbital shaker. One day before transfection, the cells were seeded at an appropriate density. The recombinant plasmid encoding target protein was transiently transfected into suspension 293□6E cell cultures. The cell culture supernatants collected on day 6 were used for purification. Cell culture broth was centrifuged and followed by filtration. Filtered culture supernatant was loaded onto affinity purification column at an appropriate flow rate. After washing and elution, the eluted fractions were pooled and buffer exchanged to final formulation buffer (PBS). The purified protein was analyzed by SDS□PAGE, Western blotting for molecular weight and purity measurements. The concentration was determined by Bradford assay with BSA as a standard.

In addition, purified protein was also tested in antigen-based ELISA to be detected by specific anti-HSA M1.69 mAb. Briefly, ELISA plates were coated with 10 µg/ml HSA or BSA purified proteins diluted in PBS at 4° C. for 24 hours. All subsequent steps were done at room temperature. The plates were blocked with 3% skim-milk in PBS for 1 hour. 100 µl of M1.69 (0.1 and 1 µg/ml) diluted in PBS were applied onto the plates and incubated for 1 hour. Following incubation, the plates were washed X3 with PBST. HRP-conjugated goat anti-rat (1:5,000 dilution in PBST) was used to detect bound M1.69. Following incubation, the plates were washed X3 with PBST and the ELISA was developed using the chromogenic HRP substrate TMB. Color development was terminated with 1 M $H_2SO_4$ and the plates were read at 450 nm.

FIG. 14 shows the specific binding of the HSA protein on ELISA plates as compared to the negative control BSA (bovine serum albumin) protein.

Example 10

Establishment of Bioassays

Setup of Bioassays

The present inventors have setup bioassays for: (1) the in-vitro biological activity of mCD24 (HSA) and (2) model system for wound healing procedure in vitro. These bioassays should allow the determination of custom normalization of CD24 activity parameters, establishment of best expression systems, comparison of protein lots, which should be the basis for future product QA/QC (quality assurance and quality control). Briefly, mc38 cells are plated in 6-well culture plates and grown to 80-90% confluence. After aspirating the medium, the center of the cell monolayer is scraped with a sterile micropipette tip to create a denuded zone (gap) of constant width. The cellular debris are then washed with PBS. The cells are fixed with 10% of paraformaldehyde and stained with 0.2% crystal violet at defined time periods. Cell migration into the cell-free area over the next 24 hour is evaluated using photographs taken with an inverted microscope. Wound closure is monitored and photographed at 0, 4, 8, and 24 hours.

Experimental Results

Determining the level of endogenous CD24 in two cancerous cell lines—The colon cancer mouse cell line mc38 and the mouse colon carcinoma cell line CT26 were used in the following experiments.

First, the expression of the HSA protein was evaluated in these cells by FACS analysis (FIG. 15A-B) and confirmed by whole-cell ELISA (FIG. 15C-D) using an anti-mCD24 antibody (an antibody which binds mouse HSA). The results show low levels of HSA expression in these cell lines, as measured by both methods.

Since the expression of HSA is relatively low in both colon cancer cell lines they can be used as a model system for in vitro assays where the HSA is given as a purified protein.

Example 11

Bioassay for the Biological Activity of CD24 Treatment

Design of In Vitro Assay

The assay is based on a mechanical wounding of cell culture, which is the most common method for studying collective cell migration, as it's a simple and cost-effective, thus mimicking the wound healing at the cellular level.

The aim of this in vitro assay for wound healing is to examine the effect of CD24 protein on skin epithelial and fibroblast proliferation and migration during in vitro wound healing. Briefly, cells were plated in 30-mm (30 millimeter) culture plates and grown to 80-90% confluence. After aspirating the medium, cell monolayer was scraped with a sterile micropipette tip to create a denuded zone (gap) of constant width. The cellular debris was then washed with PBS. Then fresh medium with or without the purified protein was added to the cells. The cells were fixed and stained at defined time periods. Cell migration into the cell-free area was evaluated using inverted microscope and wound closure was monitored and photographed at 0, 4, 8 and 24 hours.

Experimental Results

The present inventors tested the protein that was expressed from construct number 5 (described in Example 9 hereinabove).

As shown in FIG. 16A-I, the cell migration into the cell-free area was faster in plates which contained the HSA protein. In addition, a rapid closure of the gap was demonstrated (FIG. 16A-I).

The repeatability of the assay and results were tested. An additional experiment was very similar and the results are shown in FIG. 17A-L. Cell migration into the cell-free area in plates that the HSA protein was added was faster. A rapid closure of the gap was demonstrated.

Example 12

CD24 Treatment Improves Wound Healing In Vivo

Then, the present inventors have tested the ability of the protein to improve and accelerate wound closure.

Design of the In Vivo Experiment

For that purpose, the dorsal surface of the animal was cleaned and shaved. 4-cm longitudinal full-thickness incisions wounds, including the striated muscle layer, were made on the back of HSA$^{-/-}$ knockout mice. The excised wounds were left open. 100, 250 and 500 µg of purified HSA protein (prepared using construct number 5) were applied once post-wounding (injected into the cells on the wound border). 24 hours and 48 hours later, the protein was dripped into the wounded area.

Experimental Results

As shown in FIGS. 18A-L and 19A-H the wounds in HSA-treated mice were closed faster and the wounded area looked better, aesthetically.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Additional References are Cited in Text

1. Zcharia E, Zilka R, Yaar A, Yacoby-Zeevi O, Zetser A, Metzger S, et al. Heparanase accelerates wound angiogenesis and wound healing in mouse and rat models. FASEB J. 2005; 19(2):211-21. Epub Jan. 29, 2005.
2. Tonnesen M G, Feng X, Clark R A. Angiogenesis in wound healing. J Investig Dermatol Symp Proc. 2000; 5(1):40-6. Epub Jan. 9, 2001.
3. Martin P. Wound healing—aiming for perfect skin regeneration. Science. 1997; 276(5309):75-81. Epub Apr. 4, 1997.
4. Singer A J, Clark R A. Cutaneous wound healing. N Engl J Med. 1999; 341(10):738-46. Epub Sep. 2, 1999.
5. Werner S, Grose R. Regulation of wound healing by growth factors and cytokines. Physiol Rev. 2003; 83(3): 835-70. Epub Jul. 7, 2003.
6. Devalaraja R M, Nanney L B, Du J, Qian Q, Yu Y, Devalaraja M N, et al. Delayed wound healing in CXCR2 knockout mice. J Invest Dermatol. 2000; 115(2):234-44. Epub Aug. 22, 2000.
7. Martin P, Leibovich S J. Inflammatory cells during wound repair: the good, the bad and the ugly. Trends Cell Biol. 2005; 15(11):599-607. Epub Oct. 6, 2005.
8. Jaakkola P, Kontusaari S, Kauppi T, Maata A, Jalkanen M. Wound reepithelialization activates a growth factor-responsive enhancer in migrating keratinocytes. FASEB J. 1998; 12(11):959-69. Epub Aug. 26, 1998.
9. Kristiansen G, Sammar M, Altevogt P. Tumour biological aspects of CD24, a mucin-like adhesion molecule. J Mol Histol. 2004; 35(3):255-62. Epub Sep. 2, 2004.
10. Suzuki T, Kiyokawa N, Taguchi T, Sekino T, Katagiri Y U, Fujimoto J. CD24 induces apoptosis in human B cells via the glycolipid-enriched membrane domains/rafts-mediated signaling system. J Immunol. 2001; 166(9):5567-77. Epub Apr. 21, 2001.
11. Kadmon G, von Bohlen and Halbach F, Schachner M, Altevogt P. Differential, LFA-1-sensitive effects of antibodies to nectadrin, the heat-stable antigen, on B lymphoblast aggregation and signal transduction. Biochem Biophys Res Commun. 1994; 198(3):1209-15. Epub Feb. 15, 1994.
12. Aigner S, Ruppert M, Hubbe M, Sammar M, Sthoeger Z, Butcher E C, et al. Heat stable antigen (mouse CD24) supports myeloid cell binding to endothelial and platelet P-selectin. Int Immunol. 1995; 7(10):1557-65. Epub Oct. 1, 1995.
3. Aigner S, Sthoeger Z M, Fogel M, Weber E, Zarn J, Ruppert M, et al. CD24, a mucin-type glycoprotein, is a ligand for P-selectin on human tumor cells. Blood. 1997; 89(9):3385-95. Epub May 1, 1997.
14. Aigner S, Ramos C L, Hafezi-Moghadam A, Lawrence M B, Friederichs J, Altevogt P, et al. CD24 mediates rolling of breast carcinoma cells on P-selectin. FASEB J. 1998; 12(12):1241-51. Epub Sep. 16, 1998.
15. Ahmed M A, Jackson D, Seth R, Robins A, Lobo D N, Tomlinson I P, et al. CD24 is upregulated in inflammatory bowel disease and stimulates cell motility and colony formation. Inflamm Bowel Dis. 16(5):795-803. Epub Dec. 10, 2009.
16. Shapira S, Kazanov D, Weisblatt S, Starr A, Arber N, Kraus S. The CD24 protein inducible expression system is an ideal tool to explore the potential of CD24 as an oncogene and a target for immunotherapy in vitro and in vivo. J Biol Chem. 286(47):40548-55. Epub Oct. 7, 2011.
17. Sagiv E, Memeo L, Karin A, Kazanov D, Jacob-Hirsch J, Mansukhani M, et al. CD24 is a new oncogene, early at the multistep process of colorectal cancer carcinogenesis. Gastroenterology. 2006; 131(2):630-9. Epub Aug. 8, 2006.
18. Wang W, Wang X, Peng L, Deng Q, Liang Y, Qing H, et al. CD24-dependent MAPK pathway activation is required for colorectal cancer cell proliferation. Cancer Sci. 101(1):112-9. Epub Oct. 29, 2009.
19. Bretz N, Noske A, Keller S, Erbe-Hofmann N, Schlange T, Salnikov A V, et al. CD24 promotes tumor cell invasion by suppressing tissue factor pathway inhibitor-2 (TFPI-2) in a c-Src-dependent fashion. Clin Exp Metastasis. 29(1): 27-38. Epub Oct. 11, 2011.
20. Baumann P, Cremers N, Kroese F, Orend G, Chiquet-Ehrismann R, Uede T, et al. CD24 expression causes the acquisition of multiple cellular properties associated with tumor growth and metastasis. Cancer Res. 2005; 65(23): 10783-93. Epub Dec. 3, 2005.
21. Lim S C, Oh S H. The role of CD24 in various human epithelial neoplasias. Pathol Res Pract. 2005; 201(7):479-86. Epub Sep. 17, 2005.

22. Hanahan D, Weinberg R A. The hallmarks of cancer. Cell. 2000; 100(1):57-70. Epub Jan. 27, 2000.

23. Dauer D J, Ferraro B, Song L, Yu B, Mora L, Buettner R, et al. Stat3 regulates genes common to both wound healing and cancer. Oncogene. 2005; 24(21):3397-408. Epub Mar. 1, 2005.

24. Dvorak H F. Tumors: wounds that do not heal. Similarities between tumor stroma generation and wound healing. N Engl J Med. 1986; 315(26):1650-9. Epub Dec. 25, 1986.

---

What is claimed is:

1. A method of improving wound healing in a subject in need thereof, the method comprising topically administering to a wounded area of the subject a therapeutically effective amount of a CD24 protein, thereby improving the wound healing in the subject.

2. A method of improving wound healing in a subject in need thereof, the method comprising administering to the subject a therapeutically effective amount of a CD24 protein, thereby improving wound healing in the subject.

3. The method of claim 2, wherein said CD24 protein is injected to the subject.

4. The method of claim 2, wherein said CD24 protein is applied directly on a wounded area of the subject.

5. The method of claim 4, wherein said CD24 protein is applied by dropping a pharmaceutical composition comprising said CD24 protein on said wounded area of the subject.

6. The method of claim 2, wherein said CD24 protein is comprised in a medical dressing.

7. The method of claim 6, wherein said CD24 protein is soaked or impregnated in said medical dressing.

8. The method of claim 2, wherein said CD24 protein is comprised in a pharmaceutical composition.

9. The method of claim 8, wherein said CD24 protein is formulated with a surfactant in said pharmaceutical composition.

10. The method of claim 9, wherein said surfactant is an ionic surfactant.

11. The method of claim 9, wherein said surfactant is a non-ionic surfactant.

12. The method of claim 8, wherein a concentration of said CD24 protein in said pharmaceutical composition is between 1% to 10% (volume/volume) of a purified CD24 protein solution.

13. The method of claim 8, wherein said pharmaceutical composition is suitable for topical application.

14. The method of claim 13, wherein said pharmaceutical composition is comprised in an emulsion carrier, a cream, an ointment, an aqueous solution, a lotion or an aerosol.

15. The method of claim 2, wherein said CD24 protein is glycosylated.

16. The method of claim 2, wherein said CD24 protein comprises a native glycosylation pattern.

17. The method of claim 2, wherein said CD24 protein is non-glycosylated.

18. The method of claim 2, wherein said CD24 protein is soluble.

19. The method of claim 2, wherein said CD24 protein is non-soluble.

20. The method of claim 2, wherein said CD24 protein is conjugated to a lipid moiety.

* * * * *

SEQUENCE LISTING

<160> NUMBER OF SEQ ID NOS: 77

<210> SEQ ID NO 1
<211> LENGTH: 243
<212> TYPE: DNA
<213> ORGANISM: homo sapiens

<400> SEQUENCE: 1

```
atgggcagag caatggtggc caggctcggg ctggggctgc tgctgctggc actgctccta      60
cccacgcaga tttattccag tgaaacaaca actggaactt caagtaactc ctcccagagt     120
acttccaact ctgggttggc cccaaatcca actaatgcca ccaccaaggc ggctggtggt     180
gccctgcagt caacagccag tctcttcgtg gtctcactct ctcttctgca tctctactct     240
taa                                                                  243
```

<210> SEQ ID NO 2
<211> LENGTH: 78
<212> TYPE: DNA
<213> ORGANISM: homo sapiens

<400> SEQUENCE: 2

```
atgggcagag caatggtggc caggctcggg ctggggctgc tgctgctggc actgctccta      60
cccacgcaga tttattcc                                                   78
```

<210> SEQ ID NO 3
<211> LENGTH: 93
<212> TYPE: DNA
<213> ORGANISM: Artificial sequence
<220> FEATURE:
<223> OTHER INFORMATION: partial sequence of human CD24

<400> SEQUENCE: 3

```
agtgaaacaa caactggaac ttcaagtaac tcctcccaga gtacttccaa ctctgggttg      60 gcccccaaatc caactaatgc caccaccaag gcg                                 93
```

<210> SEQ ID NO 4
<211> LENGTH: 72
<212> TYPE: DNA
<213> ORGANISM: Artificial sequence
<220> FEATURE:
<223> OTHER INFORMATION: partial sequence of human CD24

<400> SEQUENCE: 4

```
gctggtggtg ccctgcagtc aacagccagt ctcttcgtgg tctcactctc tcttctgcat      60
ctctactctt aa                                                         72
```

<210> SEQ ID NO 5
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 5

```
ctggaagctt gccaccatgg atgggcagag caatggtggc                           40
```

<210> SEQ ID NO 6
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 6
tcatctagag tattaagagt agagatgcag aag                                  33

<210> SEQ ID NO 7
<211> LENGTH: 308
<212> TYPE: DNA
<213> ORGANISM: Artificial sequence
<220> FEATURE:
<223> OTHER INFORMATION: DNA sequence encoding the recombinant soluble
      CD24

<400> SEQUENCE: 7
atggagctgt atcatcctct tcttggtagc aacagctaca ggtaaggggt taacagtagc     60
aggcttgagg tctggacata tatgggtg acaatgacat ccactttgcc tttctctcca     120
caggcgcgca ctccaccggt ggctcggtac cgggcagtgg cggatcagag aatctttatt   180
ttcagggtag tgaaacaaca actggaactt caagtaactc ctcccagagt acttccaact   240
ctgggttggc tccaaatcca actaatgcca ccaccaaggc gggatcccat catcatcatc   300
atcattga                                                            308

<210> SEQ ID NO 8
<211> LENGTH: 40
<212> TYPE: DNA
<213> ORGANISM: Artificial sequence
<220> FEATURE:
<223> OTHER INFORMATION: Soluble CD24 signal peptide coding sequence
      (partial, before intron)

<400> SEQUENCE: 8
atggagctgt atcatcctct tcttggtagc aacagctaca                           40

<210> SEQ ID NO 9
<211> LENGTH: 82
<212> TYPE: DNA
<213> ORGANISM: Artificial sequence
<220> FEATURE:
<223> OTHER INFORMATION: Intron for the soluble CD24 construct

<400> SEQUENCE: 9
ggtaaggggt taacagtagc aggcttgagg tctggacata tatgggtg acaatgacat       60 ccactttgcc tttctctcca ca                                              82

<210> SEQ ID NO 10
<211> LENGTH: 12
<212> TYPE: DNA
<213> ORGANISM: Artificial sequence
<220> FEATURE:
<223> OTHER INFORMATION: Intron for the soluble CD24 construct

<400> SEQUENCE: 10
ggcgcgcact cc                                                         12

<210> SEQ ID NO 11
<211> LENGTH: 93
<212> TYPE: DNA

```
<213> ORGANISM: Artificial sequence
<220> FEATURE:
<223> OTHER INFORMATION: Soluble CD24 core protein coding sequence

<400> SEQUENCE: 11
agtgaaacaa caactggaac ttcaagtaac tcctcccaga gtacttccaa ctctgggttg    60
gctccaaatc caactaatgc caccaccaag gcg                                 93

<210> SEQ ID NO 12
<211> LENGTH: 18
<212> TYPE: DNA
<213> ORGANISM: Artificial sequence
<220> FEATURE:
<223> OTHER INFORMATION: DNA encoding a 6XHIS tag

<400> SEQUENCE: 12
catcatcatc atcatcat                                                  18

<210> SEQ ID NO 13
<211> LENGTH: 15
<212> TYPE: DNA
<213> ORGANISM: Artificial sequence
<220> FEATURE:
<223> OTHER INFORMATION: DNA encoding a flexible linker

<400> SEQUENCE: 13
ggcagtggcg gatca                                                     15

<210> SEQ ID NO 14
<211> LENGTH: 21
<212> TYPE: DNA
<213> ORGANISM: Artificial sequence
<220> FEATURE:
<223> OTHER INFORMATION: DNA encoding Tev protease cleavage site

<400> SEQUENCE: 14
gagaatcttt attttcaggg t                                              21

<210> SEQ ID NO 15
<211> LENGTH: 6
<212> TYPE: DNA
<213> ORGANISM: Artificial sequence
<220> FEATURE:
<223> OTHER INFORMATION: restriction enzyme binding site in construct
      of soluble human CD24

<400> SEQUENCE: 15 accggt                                                                6

<210> SEQ ID NO 16
<211> LENGTH: 6
<212> TYPE: DNA
<213> ORGANISM: Artificial sequence
<220> FEATURE:
<223> OTHER INFORMATION: restriction enzyme binding site in construct of
      soluble human CD24

<400> SEQUENCE: 16 ggtacc                                                                6

<210> SEQ ID NO 17
<211> LENGTH: 6
<212> TYPE: DNA
<213> ORGANISM: Artificial sequence
<220> FEATURE:
<223> OTHER INFORMATION: restriction enzyme binding site in construct of
``` soluble human CD24

<400> SEQUENCE: 17 ggatcc                                                                      6

<210> SEQ ID NO 18
<211> LENGTH: 80
<212> TYPE: PRT
<213> ORGANISM: homo sapiens

<400> SEQUENCE: 18

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80

<210> SEQ ID NO 19
<211> LENGTH: 80
<212> TYPE: PRT
<213> ORGANISM: homo sapiens

<400> SEQUENCE: 19

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80

<210> SEQ ID NO 20
<211> LENGTH: 129
<212> TYPE: PRT
<213> ORGANISM: homo sapiens

<400> SEQUENCE: 20

Met Val Gly Arg Phe Cys Pro Glu Ser Pro Gly Phe Val Arg Val
1               5                   10                  15

Ala Ala Thr Ser Ala Val Ser Leu Asp Pro Ser Gly Glu Pro Arg
            20                  25                  30

Pro Gly Cys Gly Tyr Pro Gly Pro Arg Ser Ala Ala Ser Arg Val Tyr
        35                  40                  45

Gly Cys Thr Ala Pro Ala Arg Glu Thr Gly Gly Trp Ala Trp Glu Thr
    50                  55                  60

Leu Ala Gly Ala Gly Ala Lys Lys Ile Tyr Ser Ser Glu Thr Thr Thr
65                  70                  75                  80

Gly Thr Ser Ser Asn Ser Ser Gln Ser Thr Ser Asn Ser Gly Leu Ala
            85                  90                  95

Pro Asn Pro Thr Asn Ala Thr Thr Lys Ala Ala Gly Gly Ala Leu Gln

```
            100                 105                 110
Ser Thr Ala Ser Leu Phe Val Val Ser Leu Ser Leu Leu His Leu Tyr
        115                 120                 125

Ser

<210> SEQ ID NO 21
<211> LENGTH: 80
<212> TYPE: PRT
<213> ORGANISM: homo sapiens

<400> SEQUENCE: 21

Met Gly Arg Ala Met Val Ala Arg Leu Gly Leu Gly Leu Leu Leu
1               5                   10                  15

Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
            35                  40                  45

Asn Pro Thr Asn Ala Thr Thr Lys Ala Ala Gly Gly Ala Leu Gln Ser
        50                  55                  60

Thr Ala Ser Leu Phe Val Val Ser Leu Ser Leu Leu His Leu Tyr Ser
65                  70                  75                  80

<210> SEQ ID NO 22
<211> LENGTH: 2440
<212> TYPE: DNA
<213> ORGANISM: homo sapiens

<400> SEQUENCE: 22
agtttgcagc gtcaggcagc gggtctgcgc ccagcgagcg gctccccagc tcctgggaag      60
atgcggaccc gggacgcccc cgtgagctca ctgcgcctgg ctgacacgag gcgctcacag     120
aacaaagcaa gggcttcggg gagggcgcgg ccgcggggcc gagcgcgcag atcgctccgg     180
acccggacac cgcctgcgag gagcgccgac cagccgggaa gggttcgcgc taggcggcgc     240
ccgggtcccg tcggccaggg tctcgccggc tcgccgcgct ccccaccttg cctgcgcccg     300
cccggagcca gcggttctcc aagcacccag catcctgcta gacgcgccgc gcaccgacgg     360
aggggacatg ggcagagcaa tggtggccag gctcgggctg gggctgctgc tgctggcact     420
gctcctaccc acgcagattt attccagtga acaacaact ggaacttcaa gtaactcctc      480
ccagagtact tccaactctg ggttggcccc aaatccaact aatgccacca ccaaggcggc     540
tggtggtgcc ctgcagtcaa cagccagtct cttcgtggtc tcactctctc ttctgcatct     600
ctactcttaa gagactcagg ccaagaaacg tcttctaaat ttccccatct tctaaaccca     660
atccaaatgg cgtctggaag tccaatgtgg caaggaaaaa caggtcttca tcgaatctac     720
taattccaca cctttttattg acacagaaaa tgttgagaat cccaaatttg attgatttga     780
agaacatgtg agaggtttga ctagatgatg atgccaata ttaaatctgc tggagtttca     840
tgtacaagat gaaggagagg caacatccaa aatagttaag acatgatttc cttgaatgtg     900
gcttgagaaa tatggacact taatactacc ttgaaaataa gaatagaaat aaaggatggg     960
attgtggaat ggagattcag ttttcatttg gttcattaat tctataaggc cataaaacag    1020
gtaatataaa aagcttccat gattctattt atatgtacat gagaaggaac ttccaggtgt    1080
tactgtaatt cctcaacgta ttgtttcgac agcactaatt taatgccgat atactctaga    1140
tgaagtttta cattgttgag ctattgctgt tctcttggga actgaactca ctttcctcct    1200
gaggctttgg atttgacatt gcatttgacc ttttatgtag taattgacat gtgccagggc    1260
```

```
aatgatgaat gagaatctac ccccagatcc aagcatcctg agcaactctt gattatccat    1320
attgagtcaa atggtaggca tttcctatca cctgttccca ttcaacaaga gcactacatt    1380
catttagcta aacggattcc aaagagtaga attgcattga ccacgactaa tttcaaaatg    1440
ctttttatta ttattatttt ttagacagtc tcactttgtc gcccaggccg gagtgcagtg    1500
gtgcgatctc agatcagtgt accatttgcc tcccgggctc aagcgattct cctgcctcag    1560
cctcccaagt agctgggatt acaggcacct gccaccatgc ccggctaatt tttgtaattt    1620
tagtagagac agggtttcac catgttgccc aggctggttt cgaactcctg acctcaggtg    1680
atccacccgc ctcggcctcc caaagtgctg ggattacagg cttgagcccc gcgcccagc     1740 catcaaaatg cttttatttt ctgcatatgt tgaatacttt ttacaattta aaaaaatgat    1800
ctgttttgaa ggcaaaattg caaatcttga aattaagaag gcaaaatgt aaaggagtca     1860 aaactataaa tcaagtattt gggaagtgaa gactggaagc taatttgcat taaattcaca    1920
aacttttata ctctttctgt atatacattt tttttcttta aaaacaact atggatcaga     1980 atagccacat ttagaacact ttttgttatc agtcaatatt tttagatagt tagaacctgg    2040
tcctaagcct aaaagtgggc ttgattctgc agtaaatctt ttacaactgc ctcgacacac    2100
ataaaccttt ttaaaaatag acactccccg aagtcttttg ttcgcatggt cacacactga    2160
tgcttagatg ttccagtaat ctaatatggc cacagtagtc ttgatgacca aagtcctttt    2220
tttccatctt tagaaaacta catgggaaca acagatcga acagttttga agctactgtg      2280
tgtgtgaatg aacactcttg ctttattcca gaatgctgta catctatttt ggattgtata    2340
ttgtgtttgt gtatttacgc tttgattcat agtaacttct tatggaattg atttgcattg    2400
aacacaaact gtaaataaaa agaaatggct gaaagagcaa                          2440

<210> SEQ ID NO 23
<211> LENGTH: 2295
<212> TYPE: DNA
<213> ORGANISM: homo sapiens

<400> SEQUENCE: 23
tgctcttgtt gcccaggctg gaatgcaatg gcctgatctc tgctcactgc aacctccacc      60
tctcaggttc aagctattct cctgcctcag cctcccaagt agctgggatt acaggtctcg     120
ccggctcgcc gcgctcccca ccttgcctgc gcccgcccgg agccagcggt tctccaagca     180
cccagcatcc tgctagacgc gccgcgcacc gacggagggg acatgggcag agcaatggtg     240
gccaggctcg ggctggggct gctgctgctg cactgctcc tacccacgca gatttattcc       300
agtgaaacaa caactggaac ttcaagtaac tcctcccaga gtacttccaa ctctgggttg     360
gccccaaatc caactaatgc caccaccaag gcggctggtg gtgccctgca gtcaacagcc     420
agtctcttcg tggtctcact ctctcttctg catctctact cttaagagac tcaggccaag     480
aaacgtcttc taaatttccc catcttctaa acccaatcca aatggcgtct ggaagtccaa     540
tgtggcaagg aaaaacaggt cttcatcgaa tctactaatt ccacacccttt tattgacaca    600 gaaaatgttg agaatcccaa atttgattga tttgaagaac atgtgagagg tttgactaga    660
tgatggatgc caatattaaa tctgctggag tttcatgtac aagatgaagg agaggcaaca     720
tccaaaatag ttaagacatg atttccttga atgtggcttg agaaatatgg acacttaata    780
ctaccttgaa aataagaata gaaataaagg atgggattgt ggaatggaga ttcagttttc     840
atttggttca ttaattctat aaggccataa aacaggtaat ataaaaagct tccatgattc      900
```

```
tatttatatg tacatgagaa ggaacttcca ggtgttactg taattcctca acgtattgtt      960
tcgacagcac taatttaatg ccgatatact ctagatgaag ttttacattg ttgagctatt     1020
gctgttctct tgggaactga actcactttc ctcctgaggc tttggatttg acattgcatt     1080
tgacctttta tgtagtaatt gacatgtgcc agggcaatga tgaatgagaa tctaccccca     1140
gatccaagca tcctgagcaa ctcttgatta tccatattga gtcaaatggt aggcatttcc     1200
tatcacctgt ttccattcaa caagagcact acattcattt agctaaacgg attccaaaga     1260
gtagaattgc attgaccacg actaatttca aaatgctttt tattattatt attttttaga     1320
cagtctcact ttgtcgccca ggccggagtg cagtggtgcg atctcagatc agtgtaccat     1380
ttgcctcccg ggctcaagcg attctcctgc ctcagcctcc caagtagctg ggattacagg     1440
cacctgccac catgcccggc taattttttgt aatttttagta gagacagggt ttcaccatgt     1500
tgcccaggct ggtttcgaac tcctgacctc aggtgatcca cccgcctcgg cctcccaaag     1560
tgctgggatt acaggcttga gcccccgcgc ccagccatca aaatgctttt tatttctgca     1620
tatgttgaat acttttttaca atttaaaaaa atgatctgtt ttgaaggcaa aattgcaaat     1680
cttgaaatta agaaggcaaa aatgtaaagg agtcaaaact ataaatcaag tatttgggaa     1740
gtgaagactg gaagctaatt tgcattaaat tcacaaactt ttatactctt tctgtatata     1800
cattttttttt ctttaaaaaa caactatgga tcagaatagc cacatttaga acacttttttg    1860
ttatcagtca atatttttag atagttagaa cctggtccta agcctaaaag tgggcttgat     1920
tctgcagtaa atcttttaca actgcctcga cacacataaa cctttttaaa aatagacact     1980
ccccgaagtc ttttgttcgc atggtcacac actgatgctt agatgttcca gtaatctaat     2040
atggccacag tagtcttgat gaccaaagtc ctttttttcc atctttagaa aactacatgg     2100
gaacaaacag atcgaacagt tttgaagcta ctgtgtgtgt gaatgaacac tcttgcttta     2160
ttccagaatg ctgtacatct attttggatt gtatattgtg tttgtgtatt tacgctttga     2220
ttcatagtaa cttcttatgg aattgatttg cattgaacac aaactgtaaa taaaagaaa      2280
tggctgaaag agcaa                                                      2295

<210> SEQ ID NO 24
<211> LENGTH: 2374
<212> TYPE: DNA
<213> ORGANISM: homo sapiens

<400> SEQUENCE: 24 cttttttaaac aaaccccggt tccgggctga agccgaggcg gggaccctct cctgacgctg      60
cgctctctgc gaggcaacct ttcacgtcca tcgcttgtca tcttaggatc cccatgttat     120
tttagcccag attggctagt tctggggagg cagcatggtg ggacgattct gtcccgagtc     180
cccgccaggc tttgttcggg tcgccgctac cagcgcggtc tccctagatc ctccatccgg     240
ggaacctcgc cccgggtgcg ggtacccggg gccgcgcagc gctgcctcga gggtgtatgg     300
atgcaccgcg ccgcgagag agaccggggg ctgggcctgg gagaccctag cggggggcggg     360
ggcgaagaag atttattcca gtgaaacaac aactggaact tcaagtaact cctcccagag     420
tacttccaac tctgggttgg ccccaaatcc aactaatgcc accaccaagg cggctggtgg     480
tgccctgcag tcaacagcca gtctcttcgt ggtctcactc tctcttctgc atctctactc     540
ttaagagact caggccaaga aacgtcttct aaatttcccc atcttctaaa cccaatccaa     600
atggcgtctg gaagtccaat gtggcaagga aaaacaggtc ttcatcgaat ctactaattc     660
cacaccttt attgacacag aaaatgttga gaatcccaaa tttgattgat ttgaagaaca     720
```

| | |
|---|---|
| tgtgagaggt tgactagat gatggatgcc aatattaaat ctgctggagt tcatgtaca | 780 |
| agatgaagga gaggcaacat ccaaaatagt taagacatga tttccttgaa tgtggcttga | 840 |
| gaaatatgga cacttaatac taccttgaaa ataagaatag aaataaagga tgggattgtg | 900 |
| gaatggagat tcagttttca tttggttcat taattctata aggccataaa acaggtaata | 960 |
| taaaaagctt ccatgattct atttatatgt acatgagaag gaacttccag gtgttactgt | 1020 |
| aattcctcaa cgtattgttt cgacagcact aatttaatgc cgatatactc tagatgaagt | 1080 |
| tttacattgt tgagctattg ctgttctctt gggaactgaa ctcactttcc tcctgaggct | 1140 |
| ttggatttga cattgcattt gaccttttat gtagtaattg acatgtgcca gggcaatgat | 1200 |
| gaatgagaat ctaccccag atccaagcat cctgagcaac tcttgattat ccatattgag | 1260 |
| tcaaatggta ggcatttcct atcacctgtt tccattcaac aagagcacta cattcattta | 1320 |
| gctaaacgga ttccaaagag tagaattgca ttgaccacga ctaatttcaa aatgcttttt | 1380 |
| attattatta tttttagac agtctcactt tgtcgcccag gccggagtgc agtggtgcga | 1440 |
| tctcagatca gtgtaccatt tgcctcccgg gctcaagcga ttctcctgcc tcagcctccc | 1500 |
| aagtagctgg gattacaggc acctgccacc atgcccggct aattttttgta attttagtag | 1560 |
| agacagggtt tcaccatgtt gcccaggctg gtttcgaact cctgacctca ggtgatccac | 1620 |
| ccgcctcggc ctcccaaagt gctgggatta caggcttgag ccccgcgcc cagccatcaa | 1680 |
| aatgcttttt atttctgcat atgttgaata cttttacaa tttaaaaaa tgatctgttt | 1740 |
| tgaaggcaaa attgcaaatc ttgaaattaa gaaggcaaaa atgtaaagga gtcaaaacta | 1800 |
| taaatcaagt atttgggaag tgaagactgg aagctaattt gcattaaatt cacaaacttt | 1860 |
| tatactcttt ctgtatatac attttttttc tttaaaaaac aactatggat cagaatagcc | 1920 |
| acatttagaa cacttttttgt tatcagtcaa tattttttaga tagttagaac ctggtcctaa | 1980 |
| gcctaaaagt gggcttgatt ctgcagtaaa tcttttacaa ctgcctcgac acacataaac | 2040 |
| cttttttaaaa atagacactc cccgaagtct tttgttcgca tggtcacaca ctgatgctta | 2100 |
| gatgttccag taatctaata tggccacagt agtcttgatg accaaagtcc ttttttttcca | 2160 |
| tctttagaaa actacatggg aacaaacaga tcgaacagtt ttgaagctac tgtgtgtgtg | 2220 |
| aatgaacact cttgctttat tccagaatgc tgtacatcta ttttggattg tatattgtgt | 2280 |
| ttgtgtattt acgctttgat tcatagtaac ttcttatgga attgatttgc attgaacaca | 2340 |
| aactgtaaat aaaagaaat ggctgaaaga gcaa | 2374 |

<210> SEQ ID NO 25
<211> LENGTH: 2513
<212> TYPE: DNA
<213> ORGANISM: homo sapiens

<400> SEQUENCE: 25

| | |
|---|---|
| gcgcgcagat cgctccggac ccggacaccg cctgcgagga gcgccgacca gccgggaagg | 60 |
| gttcgcgcta ggcggcgccc gggtcccgtc ggccagggtg agcgtccggc ccgcgtccgc | 120 |
| gccacgcccg ccgcgttccc ctttcctctg cggcgggccg agagataacc ctgcccgagg | 180 |
| ggtcccggcg cccgcccccc acgcggtcgc actggaattc gcagcccctc tcgggtcccc | 240 |
| ggggcgcatt ttgcagtctg agtggcaatg cacttgctcc aggacaggcg gctaccccgc | 300 |
| cgcagcggag gcgcggactt ttcttttggg ggtctcgcc ggctcgccgc gctccccacc | 360 |
| ttgcctgcgc ccgccggag ccagcggttc tccaagcacc cagcatcctg ctagacgcgc | 420 |

```
cgcgcaccga cggaggggac atgggcagag caatggtggc caggctcggg ctggggctgc    480
tgctgctggc actgctccta cccacgcaga tttattccag tgaaacaaca actggaactt    540
caagtaactc ctcccagagt acttccaact ctgggttggc cccaaatcca actaatgcca    600
ccaccaaggc ggctggtggt gccctgcagt caacagccag tctcttcgtg gtctcactct    660
ctcttctgca tctctactct taagagactc aggccaagaa acgtcttcta aatttcccca    720
tcttctaaac ccaatccaaa tggcgtctgg aagtccaatg tggcaaggaa aaacaggtct    780
tcatcgaatc tactaattcc acacctttta ttgacacaga aaatgttgag aatcccaaat    840
ttgattgatt tgaagaacat gtgagaggtt tgactagatg atggatgcca atattaaatc    900
tgctggagtt tcatgtacaa gatgaaggag aggcaacatc caaaatagtt aagacatgat    960
ttccttgaat gtggcttgag aaatatggac acttaatact accttgaaaa taagaataga    1020
aataaaggat gggattgtgg aatggagatt cagttttcat ttggttcatt aattctataa    1080
ggccataaaa caggtaatat aaaaagcttc catgattcta tttatatgta catgagaagg    1140
aacttccagg tgttactgta attcctcaac gtattgtttc gacagcacta atttaatgcc    1200
gatatactct agatgaagtt ttacattgtt gagctattgc tgttctcttg ggaactgaac    1260
tcactttcct cctgaggctt tggatttgac attgcatttg accttttatg tagtaattga    1320
catgtgccag ggcaatgatg aatgagaatc tacccccaga tccaagcatc ctgagcaact    1380
cttgattatc catattgagt caaatggtag gcatttccta tcacctgttt ccattcaaca    1440
agagcactac attcatttag ctaaacggat tccaaagagt agaattgcat tgaccacgac    1500
taatttcaaa atgcttttta ttattattat tttttagaca gtctcacttt gtcgcccagg    1560
ccggagtgca gtggtgcgat ctcagatcag tgtaccattt gcctcccggg ctcaagcgat    1620
tctcctgcct cagcctccca gtagctggga attacaggca cctgccacca tgcccggcta    1680 attttгtgtaa ttttagtaga cagggtttt caccatgttg cccaggctgg tttcgaactc    1740
ctgacctcag gtgatccacc cgcctcggcc tcccaaagtg ctgggattac aggcttgagc    1800
ccccgcgccc agccatcaaa atgcttttta tttctgcata tgttgaatac ttttacaat    1860 ttaaaaaaat gatctgtttt gaaggcaaaa ttgcaaatct tgaaattaag aaggcaaaaa    1920
tgtaaaggag tcaaaactat aaatcaagta tttgggaagt gaagactgga agctaatttg    1980
cattaaattc acaacttttt atactctttc tgtatataca ttttttttct ttaaaaaaca    2040
actatggatc agaatagcca catttagaac acttttgtt atcagtcaat attttагtаgat    2100 agttagaacc tggtcctaag cctaaaaagtg ggcttgattc tgcagtaaat cttttacaac    2160
tgcctcgaca cacataaacc ttttaaaaa tagacactcc ccgaagtctt tgttcgcat    2220 ggtcacacac tgatgcttag atgttccagt aatctaatat ggccacagta gtcttgatga    2280
ccaaagtcct ttttttccat ctttagaaaa ctacatggga acaaacagat cgaacagttt    2340
tgaagctact gtgtgtgtga atgaacactc ttgctttatt ccagaatgct gtacatctat    2400
tttggattgt atattgtgtt tgtgtattta cgctttgatt catagtaact tcttatggaa    2460
ttgatttgca ttgaacacaa actgtaaata aaagaaatg gctgaaagag caa           2513
```

<210> SEQ ID NO 26
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 26
atatacatat gggcagagcg atggtggcc                                29

<210> SEQ ID NO 27
<211> LENGTH: 59
<212> TYPE: DNA
<213> ORGANISM: Artificial sequence
<220> FEATURE:
<223> OTHER INFORMATION: Single strand DNA oligonucleotide

<400> SEQUENCE: 27
tatatgaatt cttagtgatg gtgatggtga tgcggcggtt gacagtagag atgtagaag      59

<210> SEQ ID NO 28
<211> LENGTH: 31
<212> TYPE: PRT
<213> ORGANISM: Artificial sequence
<220> FEATURE:
<223> OTHER INFORMATION: CD24 core protein

<400> SEQUENCE: 28

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Ala
            20                  25                  30

<210> SEQ ID NO 29
<211> LENGTH: 80
<212> TYPE: PRT
<213> ORGANISM: Artificial sequence
<220> FEATURE:
<223> OTHER INFORMATION: CD24 full length protein

<400> SEQUENCE: 29

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80

<210> SEQ ID NO 30
<211> LENGTH: 76
<212> TYPE: PRT
<213> ORGANISM: Artificial sequence
<220> FEATURE:
<223> OTHER INFORMATION: CD24 soluble protein

<400> SEQUENCE: 30

Met Gly Trp Ser Cys Ile Ile Leu Phe Leu Val Ala Thr Ala Thr Gly
1               5                   10                  15

Ala His Ser Thr Gly Gly Ser Val Pro Gly Ser Gly Gly Ser Glu Asn
            20                  25                  30

Leu Tyr Phe Gln Gly Ser Glu Thr Thr Thr Gly Thr Ser Ser Asn Ser
            35                  40                  45

Ser Gln Ser Thr Ser Asn Ser Gly Leu Ala Pro Asn Pro Thr Asn Ala
    50                  55                  60

Thr Thr Lys Ala Gly Ser His His His His His His

<210> SEQ ID NO 31
<211> LENGTH: 27
<212> TYPE: PRT
<213> ORGANISM: Artificial sequence
<220> FEATURE:
<223> OTHER INFORMATION: CD24 soluble protein

<400> SEQUENCE: 31

Asn Gln Thr Ser Val Ala Pro Phe Pro Gly Asn Gln Asn Ile Ser Ala
1               5                   10                  15

Ser Pro Asn Pro Ser Asn Ala Thr Thr Arg Gly
            20                  25

<210> SEQ ID NO 32
<211> LENGTH: 11
<212> TYPE: PRT
<213> ORGANISM: Artificial sequence
<220> FEATURE:
<223> OTHER INFORMATION: TAT peptide sequence

<400> SEQUENCE: 32

Tyr Gly Arg Lys Lys Arg Arg Gln Arg Arg Arg
1               5                   10

<210> SEQ ID NO 33
<211> LENGTH: 25
<212> TYPE: PRT
<213> ORGANISM: Artificial sequence
<220> FEATURE:
<223> OTHER INFORMATION: Signal peptide (HSA)

<400> SEQUENCE: 33

Gly Arg Ala Met Val Ala Arg Leu Gly Leu Gly Leu Leu Leu Leu Ala
1               5                   10                  15

Leu Leu Leu Pro Thr Gln Ile Tyr Cys
            20                  25

<210> SEQ ID NO 34
<211> LENGTH: 23
<212> TYPE: PRT
<213> ORGANISM: Artificial sequence
<220> FEATURE:
<223> OTHER INFORMATION: C-terminus HSA

<400> SEQUENCE: 34

Gly Gly Ser Ser Leu Gln Ser Thr Ala Gly Leu Leu Ala Leu Ser Leu
1               5                   10                  15

Ser Leu Leu His Leu Tyr Cys
            20

<210> SEQ ID NO 35
<211> LENGTH: 6
<212> TYPE: PRT
<213> ORGANISM: Artificial sequence
<220> FEATURE:
<223> OTHER INFORMATION: Linker

<400> SEQUENCE: 35

Gly Gly Ser Gly Gly Ser
1               5

<210> SEQ ID NO 36
<211> LENGTH: 22

```
<212> TYPE: PRT
<213> ORGANISM: Artificial sequence
<220> FEATURE:
<223> OTHER INFORMATION: TM domain

<400> SEQUENCE: 36

Ala Thr Gly Met Val Gly Ala Leu Leu Leu Leu Val Val Ala Leu
1               5                   10                  15

Gly Ile Gly Leu Phe Met
            20

<210> SEQ ID NO 37
<211> LENGTH: 222
<212> TYPE: PRT
<213> ORGANISM: Artificial sequence
<220> FEATURE:
<223> OTHER INFORMATION: Fc region

<400> SEQUENCE: 37

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Asn
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 38
<211> LENGTH: 34
<212> TYPE: PRT
<213> ORGANISM: Artificial sequence
<220> FEATURE:
<223> OTHER INFORMATION: linker

<400> SEQUENCE: 38

Ala Ala Ala Asn Ser Ser Ile Asp Leu Ile Ser Val Pro Val Asp Ser
1               5                   10                  15

Arg Arg Pro Ala Cys Lys Ile Pro Asn Asp Leu Lys Gln Lys Val Met
```

```
                    20                  25                  30
Asn His

<210> SEQ ID NO 39
<211> LENGTH: 8
<212> TYPE: PRT
<213> ORGANISM: Artificial sequence
<220> FEATURE:
<223> OTHER INFORMATION: FLAG/EK

<400> SEQUENCE: 39

Asp Tyr Lys Asp Asp Asp Asp Lys
1               5

<210> SEQ ID NO 40
<211> LENGTH: 26
<212> TYPE: PRT
<213> ORGANISM: Artificial sequence
<220> FEATURE:
<223> OTHER INFORMATION: CD24 signal peptide protein sequence

<400> SEQUENCE: 40

Met Gly Arg Ala Met Val Ala Arg Leu Gly Leu Gly Leu Leu Leu Leu
1               5                   10                  15

Ala Leu Leu Leu Pro Thr Gln Ile Tyr Ser
            20                  25

<210> SEQ ID NO 41
<211> LENGTH: 23
<212> TYPE: PRT
<213> ORGANISM: Artificial sequence
<220> FEATURE:
<223> OTHER INFORMATION: CD24 C-terminus protein sequence

<400> SEQUENCE: 41

Ala Gly Gly Ala Leu Gln Ser Thr Ala Ser Leu Phe Val Val Ser Leu
1               5                   10                  15

Ser Leu Leu His Leu Tyr Ser
            20

<210> SEQ ID NO 42
<211> LENGTH: 13
<212> TYPE: PRT
<213> ORGANISM: Artificial sequence
<220> FEATURE:
<223> OTHER INFORMATION: Soluble CD24 signal peptide protein sequence
      (partial, before intron)

<400> SEQUENCE: 42

Met Glu Leu Tyr His Pro Leu Leu Gly Ser Asn Ser Tyr
1               5                   10

<210> SEQ ID NO 43
<211> LENGTH: 4
<212> TYPE: PRT
<213> ORGANISM: Artificial sequence
<220> FEATURE:
<223> OTHER INFORMATION: Soluble CD24 signal peptide protein sequence
      (partial, after intron)

<400> SEQUENCE: 43

Gly Ala His Ser
1

<210> SEQ ID NO 44
```

<211> LENGTH: 6
<212> TYPE: PRT
<213> ORGANISM: Artificial sequence
<220> FEATURE:
<223> OTHER INFORMATION: His tag

<400> SEQUENCE: 44

His His His His His His
1               5

<210> SEQ ID NO 45
<211> LENGTH: 7
<212> TYPE: PRT
<213> ORGANISM: Artificial sequence
<220> FEATURE:
<223> OTHER INFORMATION: Tev protease cleavage site

<400> SEQUENCE: 45

Glu Asn Leu Tyr Phe Gln Gly
1               5

<210> SEQ ID NO 46
<211> LENGTH: 711
<212> TYPE: DNA
<213> ORGANISM: Artificial sequence
<220> FEATURE:
<223> OTHER INFORMATION: mCherry DNA coding sequence

<400> SEQUENCE: 46

```
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact cccctccga cggccccgta      420
atgcagaaga gaccatgggc tgggaggcc tcctccgagc ggatgtaccc cgaggacggc      480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaagta a              711
```

<210> SEQ ID NO 47
<211> LENGTH: 236
<212> TYPE: PRT
<213> ORGANISM: Artificial sequence
<220> FEATURE:
<223> OTHER INFORMATION: mCherry protein sequence

<400> SEQUENCE: 47

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 48
<211> LENGTH: 31
<212> TYPE: DNA
<213> ORGANISM: Artificial sequence
<220> FEATURE:
<223> OTHER INFORMATION: TAT DNA coding sequence

<400> SEQUENCE: 48
tatggccgta aaaaacgccg ccagcgtcgt c                                    31

<210> SEQ ID NO 49
<211> LENGTH: 66
<212> TYPE: DNA
<213> ORGANISM: Artificial sequence
<220> FEATURE:
<223> OTHER INFORMATION: TM DNA coding sequence

<400> SEQUENCE: 49
gccacaggta tggtgggtgc cctgctgctg ctgctggttg tggccctggg catcggtctg     60
ttcatg                                                                66

<210> SEQ ID NO 50
<211> LENGTH: 18
<212> TYPE: DNA
<213> ORGANISM: Artificial sequence
<220> FEATURE:
<223> OTHER INFORMATION: linker DNA coding sequence

<400> SEQUENCE: 50
ggtggtagcg gtggtagc                                                   18

<210> SEQ ID NO 51
<211> LENGTH: 26
<212> TYPE: PRT
<213> ORGANISM: Artificial sequence
<220> FEATURE:
<223> OTHER INFORMATION: HSA signal peptide coding seuquence -continued

<400> SEQUENCE: 51

Met Gly Arg Ala Met Val Ala Arg Leu Gly Leu Gly Leu Leu Leu Leu
1               5                   10                  15

Ala Leu Leu Leu Pro Thr Gln Ile Tyr Cys
            20                  25

<210> SEQ ID NO 52
<211> LENGTH: 27
<212> TYPE: PRT
<213> ORGANISM: Artificial sequence
<220> FEATURE:
<223> OTHER INFORMATION: HSA core protein coding sequence

<400> SEQUENCE: 52

Asn Gln Thr Ser Val Ala Pro Phe Pro Gly Asn Gln Asn Ile Ser Ala
1               5                   10                  15

Ser Pro Asn Pro Ser Asn Ala Thr Thr Arg Gly
            20                  25

<210> SEQ ID NO 53
<211> LENGTH: 23
<212> TYPE: PRT
<213> ORGANISM: Artificial sequence
<220> FEATURE:
<223> OTHER INFORMATION: C-terminus HSA coding sequence

<400> SEQUENCE: 53

Gly Gly Ser Ser Leu Gln Ser Thr Ala Gly Leu Leu Ala Leu Ser Leu
1               5                   10                  15

Ser Leu Leu His Leu Tyr Cys
            20

<210> SEQ ID NO 54
<211> LENGTH: 681
<212> TYPE: DNA
<213> ORGANISM: Artificial sequence
<220> FEATURE:
<223> OTHER INFORMATION: Fc region coding sequence

<400> SEQUENCE: 54
gacaagaccc acacctgtcc tccatgtccc gcccctgaac tgctgggcgg acctagcgtg      60
ttcctgttcc cccaaagcc caaggacacc ctgatgatca gccggacccc cgaagtgacc      120
tgcgtggtgg tggatgtgtc ccacgaggac cctgaagtga agttcaattg gtacgtggac     180
ggcgtggaag tgcacaacgc caagaccaag cccagagagg aacagtacaa cagcacctac     240
cgggtggtgt ccgtgctgac cgtgctgcac caggactggc tgaacggcaa agagtacaag     300
tgcaaggtgt ccaacaaggc cctgcctgcc cccatcgaga aaaccatcag caaggccaag     360
ggccagcccc gcgaacccca ggtgtacaca ctgcccccta gccgggaaga tgaccaag      420 aaccaggtgt ccctgacctg tctcgtgaag ggcttctacc cctccgatat cgccgtggaa     480
tgggagagca acggccagcc cgagaacaac tacaagacca ccccccctgt gctggacagc     540
gacggctcat tcttcctgta cagcaagctg acagtggaca gagccggtg gcagcagggc      600 aacgtgttca gctgcagcgt gatgcacgag gccctgcaca accactacac ccagaagtcc     660
ctgagcctga gccctggaaa g                                              681

<210> SEQ ID NO 55
<211> LENGTH: 24
<212> TYPE: DNA

```
<213> ORGANISM: Artificial sequence
<220> FEATURE:
<223> OTHER INFORMATION: FLAG/EK coding sequence

<400> SEQUENCE: 55
gactacaagg acgacgacga caag                                          24

<210> SEQ ID NO 56
<211> LENGTH: 231
<212> TYPE: DNA
<213> ORGANISM: Artificial sequence
<220> FEATURE:
<223> OTHER INFORMATION: Full length HSA coding sequence

<400> SEQUENCE: 56
atgggcagag cgatggtggc caggctaggg ctggggttgc tgcttctggc actgctccta   60
cccacgcaga tttactgcaa ccaaacatct gttgcaccgt tcccggtaa ccagaatatt   120 tctgcttccc caaatccaag taacgctacc accagagggg gtggcagctc cctgcagtcc  180
acagctggtc tcctggctct ctctctctct cttctacatc tctactgtta g           231

<210> SEQ ID NO 57
<211> LENGTH: 76
<212> TYPE: PRT
<213> ORGANISM: Artificial sequence
<220> FEATURE:
<223> OTHER INFORMATION: Full length HSA Protein sequence

<400> SEQUENCE: 57

Met Gly Arg Ala Met Val Ala Arg Leu Gly Leu Gly Leu Leu Leu Leu
1               5                   10                  15

Ala Leu Leu Leu Pro Thr Gln Ile Tyr Cys Asn Gln Thr Ser Val Ala
            20                  25                  30

Pro Phe Pro Gly Asn Gln Asn Ile Ser Ala Ser Pro Asn Pro Ser Asn
        35                  40                  45

Ala Thr Thr Arg Gly Gly Gly Ser Ser Leu Gln Ser Thr Ala Gly Leu
    50                  55                  60

Leu Ala Leu Ser Leu Ser Leu Leu His Leu Tyr Cys
65                  70                  75

<210> SEQ ID NO 58
<211> LENGTH: 111
<212> TYPE: DNA
<213> ORGANISM: Artificial sequence
<220> FEATURE:
<223> OTHER INFORMATION: construct 1 (Fig. 13A) coding seq

<400> SEQUENCE: 58
atgaaccaaa caagcgtggc acccttccct ggaaaccaaa atatatccgc gtcccctaac   60
ccgtccaatg cgaccacccg aggcggatcc catcatcacc atcatcacta g            111

<210> SEQ ID NO 59
<211> LENGTH: 36
<212> TYPE: PRT
<213> ORGANISM: Artificial sequence
<220> FEATURE:
<223> OTHER INFORMATION: construct 1 (Fig. 13A) protein seq

<400> SEQUENCE: 59

Met Asn Gln Thr Ser Val Ala Pro Phe Pro Gly Asn Gln Asn Ile Ser
1               5                   10                  15

Ala Ser Pro Asn Pro Ser Asn Ala Thr Thr Arg Gly Gly Ser His His
```

His His His His
        35

<210> SEQ ID NO 60
<211> LENGTH: 282
<212> TYPE: DNA
<213> ORGANISM: Artificial sequence
<220> FEATURE:
<223> OTHER INFORMATION: construct 2 (Fig. 13B) coding seq

<400> SEQUENCE: 60

```
atgtatggcc gtaaaaaacg ccgccagcgt cgtcgtggtc gtgcaatggt ggcccgtctg      60
ggtctgggtc tgctgctgct ggccctgctg ctgccgacac agatctactg caatcagacc     120
agcgtggccc cgtttccggg caatcagaat attagcgcca gcccgaatcc gagcaatgcc     180
accacccgtg gtggtggtag cagcctgcag agcacagccg gtctgctggc actgagcctg     240
agcctgctgc atctgtattg ccaccatcat caccatcatt aa                        282
```

<210> SEQ ID NO 61
<211> LENGTH: 93
<212> TYPE: PRT
<213> ORGANISM: Artificial sequence
<220> FEATURE:
<223> OTHER INFORMATION: construct 2 (Fig. 13B) coding seq

<400> SEQUENCE: 61

Met Tyr Gly Arg Lys Lys Arg Arg Gln Arg Arg Gly Arg Ala Met
1               5                   10                  15

Val Ala Arg Leu Gly Leu Gly Leu Leu Leu Ala Leu Leu Leu Pro
                20                  25                  30

Thr Gln Ile Tyr Cys Asn Gln Thr Ser Val Ala Pro Phe Pro Gly Asn
            35                  40                  45

Gln Asn Ile Ser Ala Ser Pro Asn Pro Ser Asn Ala Thr Thr Arg Gly
        50                  55                  60

Gly Gly Ser Ser Leu Gln Ser Thr Ala Gly Leu Leu Ala Leu Ser Leu
65                  70                  75                  80

Ser Leu Leu His Leu Tyr Cys His His His His His
                85                  90

<210> SEQ ID NO 62
<211> LENGTH: 147
<212> TYPE: DNA
<213> ORGANISM: Artificial sequence
<220> FEATURE:
<223> OTHER INFORMATION: construct 3 (Fig. 13C) coding seq

<400> SEQUENCE: 62

```
atggggtatg gcagaaagaa gcgacgccaa cggcgaagga atcaaaccag cgtcgcgccg      60
ttccctggca atcagaacat tagtgcgagt cctaatccga gtaacgccac gacacgcggg     120
ggaagccatc accatcatca tcactag                                         147
```

<210> SEQ ID NO 63
<211> LENGTH: 47
<212> TYPE: PRT
<213> ORGANISM: Artificial sequence
<220> FEATURE:
<223> OTHER INFORMATION: construct 3 (Fig. 13C) protein seq

<400> SEQUENCE: 63

Met Tyr Gly Arg Lys Lys Arg Arg Gln Arg Arg Asn Gln Thr Ser
1               5                   10                  15

Val Ala Pro Phe Pro Gly Asn Gln Asn Ile Ser Ala Ser Pro Asn Pro
                20                  25                  30

Ser Asn Ala Thr Thr Arg Gly Gly Ser His His His His His His
            35                  40                  45

<210> SEQ ID NO 64
<211> LENGTH: 294
<212> TYPE: DNA
<213> ORGANISM: Artificial sequence
<220> FEATURE:
<223> OTHER INFORMATION: construct 4 (Fig. 13D) coding seq

<400> SEQUENCE: 64
atgtacggcc gcaaaaaacg ccgtcagcgt cgtcgtggtc gtgccatggt tgcccgctta     60
ggtctgggcc tgctgctgct ggcactgctg ctgccgaccc agatttactg caatcagacc    120
agcgtggccc cgtttccggg taatcagaac attagcgcca gcccgaatcc gagcaatgcc    180 accaccgtg gtggtagcgg tggtagcgcc acaggtatgg tgggtgccct gctgctgctg     240
ctggttgtgg ccctgggcat cggtctgttc atgcatcacc atcatcatca ttaa           294

<210> SEQ ID NO 65
<211> LENGTH: 97
<212> TYPE: PRT
<213> ORGANISM: Artificial sequence
<220> FEATURE:
<223> OTHER INFORMATION: construct 4 (Fig. 13D) protein seq

<400> SEQUENCE: 65

Met Tyr Gly Arg Lys Lys Arg Arg Gln Arg Arg Gly Arg Ala Met
1               5                   10                  15

Val Ala Arg Leu Gly Leu Gly Leu Leu Leu Ala Leu Leu Leu Pro
                20                  25                  30

Thr Gln Ile Tyr Cys Asn Gln Thr Ser Val Ala Pro Phe Pro Gly Asn
            35                  40                  45

Gln Asn Ile Ser Ala Ser Pro Asn Pro Ser Asn Ala Thr Thr Arg Gly
        50                  55                  60

Gly Ser Gly Gly Ser Ala Thr Gly Met Val Gly Ala Leu Leu Leu Leu
65                  70                  75                  80

Leu Val Val Ala Leu Gly Ile Gly Leu Phe Met His His His His His
                85                  90                  95

His

<210> SEQ ID NO 66
<211> LENGTH: 1045
<212> TYPE: DNA
<213> ORGANISM: Artificial sequence
<220> FEATURE:
<223> OTHER INFORMATION: construct 5 (Fig. 13E) coding seq

<400> SEQUENCE: 66
atgggatgga gctgtatcat cctcttcttg gtagcaacag ctacaggtaa ggggttaaca     60
gtagcaggct tgaggtctgg acatatatat gggtgacaat gacatccact ttgcctttct    120
ctccacaggc gtgcactccg acaagaccca cacctgtcct ccatgtcccg ccctgaact     180 gctgggcgga cctagcgtgt tcctgttccc cccaaagccc aaggacaccc tgatgatcag    240
ccggaccccc gaagtgacct gcgtggtggt ggatgtgtcc cacgaggacc ctgaagtgaa    300

```
gttcaattgg tacgtggacg gcgtggaagt gcacaacgcc aagaccaagc ccagagagga    360
acagtacaac agcacctacc gggtggtgtc cgtgctgacc gtgctgcacc aggactggct    420
gaacggcaaa gagtacaagt gcaaggtgtc caacaaggcc ctgcctgccc ccatcgagaa    480
aaccatcagc aaggccaagg gccagccccg cgaaccccag gtgtacacac tgcccccctag  540 ccgggaagag atgaccaaga accaggtgtc cctgacctgt ctcgtgaagg gcttctaccc    600
ctccgatatc gccgtggaat gggagagcaa cggccagccc gagaacaact acaagaccac    660 ccccccctgtg ctggacagcg acggctcatt cttcctgtac agcaagctga cagtggacaa   720
gagccggtgg cagcagggca acgtgttcag ctgcagcgtg atgcacgagg ccctgcacaa    780
ccactacacc cagaagtccc tgagcctgag ccctggaaag gccgctgcca acagcagcat    840
cgacctgatc agcgtgcccg tggacagcag aaggccagcc tgcaagatcc ccaacgacct    900
gaagcagaaa gtgatgaacc acgactacaa ggacgacgac gacaagaatc agaccagcgt    960 ggcccccattc cccggcaacc agaatatcag cgccagcccc aacccagca acgccacaac     1020 aagaggccac caccatcacc accac                                          1045
```

<210> SEQ ID NO 67
<211> LENGTH: 321
<212> TYPE: PRT
<213> ORGANISM: Artificial sequence
<220> FEATURE:
<223> OTHER INFORMATION: construct 5 (Fig. 13E) protein seq

<400> SEQUENCE: 67

```
Met Gly Trp Ser Cys Ile Ile Leu Phe Leu Val Ala Thr Ala Thr Gly
1               5                   10                  15

Val His Ser Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
```

```
                225                 230                 235                 240
Ser Leu Ser Pro Gly Lys Ala Ala Ala Asn Ser Ser Ile Asp Leu Asp
                245                 250                 255

Ser Arg Arg Pro Ala Cys Lys Ile Pro Asn Asp Leu Lys Gln Lys Val
                260                 265                 270

Met Asn His Ile Ser Val Pro Val Asp Tyr Lys Asp Asp Asp Lys
                275                 280                 285

Asn Gln Thr Ser Val Ala Pro Phe Pro Gly Asn Gln Asn Ile Ser Ala
                290                 295                 300

Ser Pro Asn Pro Ser Asn Ala Thr Thr Arg Gly His His His His
305                 310                 315                 320

His

<210> SEQ ID NO 68
<211> LENGTH: 117
<212> TYPE: DNA
<213> ORGANISM: Artificial sequence
<220> FEATURE:
<223> OTHER INFORMATION: construct 1 (Fig. 13A) coding seq-Human

<400> SEQUENCE: 68
atgagtgaaa caacaactgg aacttcaagt aactcctccc agagtacttc caactctggg     60
ttggccccaa atccaactaa tgccaccacc aaggcgcatc atcaccatca tcactag      117

<210> SEQ ID NO 69
<211> LENGTH: 38
<212> TYPE: PRT
<213> ORGANISM: Artificial sequence
<220> FEATURE:
<223> OTHER INFORMATION: construct 1 (Fig. 13A) protein seq-Human

<400> SEQUENCE: 69

Met Ser Glu Thr Thr Thr Gly Thr Ser Ser Asn Ser Ser Gln Ser Thr
1               5                  10                  15

Ser Asn Ser Gly Leu Ala Pro Asn Pro Thr Asn Ala Thr Thr Lys Ala
                20                  25                  30

His His His His His His
        35

<210> SEQ ID NO 70
<211> LENGTH: 294
<212> TYPE: DNA
<213> ORGANISM: Artificial sequence
<220> FEATURE:
<223> OTHER INFORMATION: construct 2 (Fig. 13B) coding seq-Human

<400> SEQUENCE: 70
atggggtatg gcagaaagaa gcgacgccaa cggcgaagga gtggcagagc aatggtggcc     60
aggctcgggc tggggctgct gctgctggca ctgctcctac ccacgcagat ttattccgaa    120
acaacaactg gaacttcaag taactcctcc cagagtactt ccaactctgg gttggcccca    180
aatccaacta tgccaccac caaggcggct ggtggtgccc tgcagtcaac agccagtctc    240
ttcgtggtct cactctctct tctgcatctc tactctcatc atcaccatca tcac          294

<210> SEQ ID NO 71
<211> LENGTH: 98
<212> TYPE: PRT
<213> ORGANISM: Artificial sequence
<220> FEATURE:
<223> OTHER INFORMATION: construct 2 (Fig. 13B) protein seq-Human
```

<400> SEQUENCE: 71

Met Gly Tyr Gly Arg Lys Lys Arg Arg Gln Arg Arg Ser Gly Arg
1               5                   10                  15

Ala Met Val Ala Arg Leu Gly Leu Gly Leu Leu Leu Leu Ala Leu Leu
            20                  25                  30

Leu Pro Thr Gln Ile Tyr Ser Glu Thr Thr Thr Gly Thr Ser Ser Asn
        35                  40                  45

Ser Ser Gln Ser Thr Ser Asn Ser Gly Leu Ala Pro Asn Pro Thr Asn
    50                  55                  60

Ala Thr Thr Lys Ala Ala Gly Gly Ala Leu Gln Ser Thr Ala Ser Leu
65                  70                  75                  80

Phe Val Val Ser Leu Ser Leu Leu His Leu Tyr Ser His His His His
                85                  90                  95

His His

<210> SEQ ID NO 72
<211> LENGTH: 153
<212> TYPE: DNA
<213> ORGANISM: Artificial sequence
<220> FEATURE:
<223> OTHER INFORMATION: construct 3 (Fig. 13C) coding seq-Human

<400> SEQUENCE: 72
atggggtatg gcagaaagaa gcgacgccaa cggcgaagga gtgaaacaac aactggaact     60
tcaagtaact cctcccagag tacttccaac tctgggttgg ccccaaatcc aactaatgcc    120
accaccaagg cgcatcacca tcatcatcac tag                                 153

<210> SEQ ID NO 73
<211> LENGTH: 49
<212> TYPE: PRT
<213> ORGANISM: Artificial sequence
<220> FEATURE:
<223> OTHER INFORMATION: construct 3 (Fig. 13C) protein seq-Human

<400> SEQUENCE: 73

Met Tyr Gly Arg Lys Lys Arg Arg Gln Arg Arg Ser Glu Thr Thr
1               5                   10                  15

Thr Gly Thr Ser Ser Asn Ser Ser Gln Ser Thr Ser Asn Ser Gly Leu
            20                  25                  30

Ala Pro Asn Pro Thr Asn Ala Thr Thr Lys Ala His His His His His
        35                  40                  45

His

<210> SEQ ID NO 74
<211> LENGTH: 312
<212> TYPE: DNA
<213> ORGANISM: Artificial sequence
<220> FEATURE:
<223> OTHER INFORMATION: construct 4 (Fig. 13D) coding seq-Human

<400> SEQUENCE: 74
atggggtatg gcagaaagaa gcgacgccaa cggcgaagga gtggcagagc aatggtggcc     60
aggctcgggc tggggctgct gctgctggca ctgctcctac ccacgcagat ttattccgaa    120
acaacaactg gaacttcaag taactcctcc cagagtactt ccaactctgg gttggcccca    180
aatccaacta tgccaccacc aaggcgggt ggtagcggtg gtagcgccac aggtatggtg     240
ggtgccctgc tgctgctgct ggttgtggcc ctgggcatcg gtctgttcat gcatcaccat    300
catcatcact ag                                                        312

<210> SEQ ID NO 75
<211> LENGTH: 104
<212> TYPE: PRT
<213> ORGANISM: Artificial sequence
<220> FEATURE:
<223> OTHER INFORMATION: construct 4 (Fig. 13D) protein seq-Human

<400> SEQUENCE: 75

Met Gly Tyr Gly Arg Lys Lys Arg Gln Arg Arg Ser Gly Arg
1               5                   10                  15

Ala Met Val Ala Arg Leu Gly Leu Gly Leu Leu Leu Ala Leu Leu
            20                  25                  30

Leu Pro Thr Gln Ile Tyr Ser Ser Glu Thr Thr Thr Gly Thr Ser Ser
                35                  40                  45

Asn Ser Ser Gln Ser Thr Ser Asn Ser Gly Leu Ala Pro Asn Pro Thr
        50                  55                  60

Asn Ala Thr Thr Lys Ala Gly Gly Ser Gly Gly Ser Ala Thr Gly Met
65                  70                  75                  80

Val Gly Ala Leu Leu Leu Leu Leu Val Val Ala Leu Gly Ile Gly Leu
                85                  90                  95

Phe Met His His His His His His
            100

<210> SEQ ID NO 76
<211> LENGTH: 999
<212> TYPE: DNA
<213> ORGANISM: Artificial sequence
<220> FEATURE:
<223> OTHER INFORMATION: construct 5 (Fig. 13E) coding seq-Human

<400> SEQUENCE: 76
atgagtggca gagcaatggt ggccaggctc gggctggggc tgctgctgct ggcactgctc      60
ctacccacgc agatttattc cgacaagacc cacacctgtc ctccatgtcc cgccctgaa     120 ctgctgggcg gacctagcgt gttcctgttc cccccaaagc caaggacac cctgatgatc     180 agccggaccc ccgaagtgac ctgcgtggtg gtggatgtgt cccacgagga ccctgaagtg    240
aagttcaatt ggtacgtgga cggcgtggaa gtgcacaacg ccaagaccaa gcccagagag    300
gaacagtaca acagcaccta ccgggtggtg tccgtgctga ccgtgctgca ccaggactgg    360
ctgaacggca agagtacaa gtgcaaggtg tccaacaagg ccctgcctgc ccccatcgag    420
aaaaccatca gcaaggccaa gggccagccc cgcgaacccc aggtgtacac actgccccct    480
agccgggaag atgaccaa gaaccaggtg tccctgacct gtctcgtgaa gggcttctac     540
ccctccgata tcgccgtgga atgggagagc aacggccagc ccgagaacaa ctacaagacc    600
accccccctg tgctggacag cgacggctca ttcttcctgt acagcaagct gacagtggac    660
aagagccggt ggcagcaggg caacgtgttc agctgcagcg tgatgcacga ggccctgcac    720
aaccactaca cccagaagtc cctgagcctg agccctggaa aggccgctgc caacagcagc    780
atcgacctga tcagcgtgcc cgtggacagc agaaggccag cctgcaagat ccccaacgac    840
ctgaagcaga aagtgatgaa ccacgactac aaggacgacg acgacaagag tgaaacaaca    900
actggaactt caagtaactc ctcccagagt acttccaact ctgggttggc cccaaatcca    960
actaatgcca ccaccaaggc gcatcatcac catcatcac                            999

```
<210> SEQ ID NO 77
<211> LENGTH: 333
<212> TYPE: PRT
<213> ORGANISM: Artificial sequence
<220> FEATURE:
<223> OTHER INFORMATION: construct 5 (Fig. 13E) coding seq-Human

<400> SEQUENCE: 77

Met Ser Gly Arg Ala Met Val Ala Arg Leu Gly Leu Gly Leu Leu Leu
1               5                   10                  15

Leu Ala Leu Leu Leu Pro Thr Gln Ile Tyr Ser Asp Lys Thr His Thr
                20                  25                  30

Cys Pro Pro Cys Pro Ala Pro Glu Leu Leu Gly Gly Pro Ser Val Phe
            35                  40                  45

Leu Phe Pro Pro Lys Pro Lys Asp Thr Leu Met Ile Ser Arg Thr Pro
    50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Glu Glu Met Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys Ala Ala
                245                 250                 255

Ala Asn Ser Ser Ile Asp Leu Ile Ser Val Pro Val Asp Ser Arg Arg
            260                 265                 270

Pro Ala Cys Lys Ile Pro Asn Asp Leu Lys Gln Lys Val Met Asn His
        275                 280                 285

Asp Tyr Lys Asp Asp Asp Lys Ser Glu Thr Thr Thr Gly Thr Ser
    290                 295                 300

Ser Asn Ser Ser Gln Ser Thr Ser Asn Ser Gly Leu Ala Pro Asn Pro
305                 310                 315                 320

Thr Asn Ala Thr Thr Lys Ala His His His His His His
                325                 330
```